United States Patent
Kang et al.

(10) Patent No.: US 10,786,545 B2
(45) Date of Patent: Sep. 29, 2020

(54) USE OF PEPTIDES THAT BLOCK METADHERIN-SND1 INTERACTION AS TREATMENT FOR CANCER

(71) Applicants: The Trustees of Princeton University, Princeton, NJ (US); Wisconsin Alumni Research Foundation, Madison, WI (US)

(72) Inventors: Yibin Kang, Princeton, NJ (US); Yongna Xing, Middleton, WI (US); Liling Wan, Princeton, NJ (US); Feng Guo, Sunnyvale, CA (US)

(73) Assignees: The Trustees of Princeton University, Princeton, NJ (US); Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 16/406,837

(22) Filed: May 8, 2019

(65) Prior Publication Data

US 2019/0336574 A1  Nov. 7, 2019

Related U.S. Application Data

(62) Division of application No. 15/321,337, filed as application No. PCT/US2015/037708 on Jun. 25, 2015, now Pat. No. 10,357,539.

(60) Provisional application No. 62/016,914, filed on Jun. 25, 2014.

(51) Int. Cl.
| | |
|---|---|
| C07K 14/82 | (2006.01) |
| A61K 38/17 | (2006.01) |
| A61K 38/08 | (2019.01) |
| C07K 14/47 | (2006.01) |
| A61K 38/10 | (2006.01) |
| A61P 35/00 | (2006.01) |

(52) U.S. Cl.
CPC .......... *A61K 38/1709* (2013.01); *A61K 38/08* (2013.01); *A61K 38/10* (2013.01); *A61P 35/00* (2018.01); *C07K 14/4748* (2013.01); *C07K 14/82* (2013.01)

(58) Field of Classification Search
None
See application file for complete search history.

(56) References Cited

U.S. PATENT DOCUMENTS 10,357,539 B2 * 7/2019 Kang et al. ........ A61K 38/1709
2006/0205934 A1  9/2006 Macina et al.

FOREIGN PATENT DOCUMENTS

| JP | 2006-335659 A | 12/2006 |
| WO | WO 2005/050198 | * 6/2005 |
| WO | WO-2005/050198 A2 | 6/2005 |

OTHER PUBLICATIONS

Adams et al., PHENIX: a comprehensive Python-based system for macromolecular structure solution, Acta Crystallogr D Biol Crystallogr., 66(Pt. 2):213-21 (2010).
Ash et al., LYRIC/AEG-1 overexpression modulates BCCIPalpha protein levels in prostate tumor cells, Biochem. Biophys. Res. Commun., 371(2):333-8 (2008).
Asselin-Labat et al., Gata-3 is an essential regulator of mammary-gland morphogenesis and luminal-cell differentiation, Nat. Cell Biol., 9(2):201-9 (2007).
Bernards et al., A progression puzzle, Nature, 418(6900):823 (2002).
Blanco et al., Identification of *staphylococcal* nuclease domain-containing 1 (SND1) as a Metadherin-interacting protein with metastasis-promoting functions, J. Biol. Chem., 286(22):19982-92 (2011).
Britt et al., Identification of a novel protein, LYRIC, localized to tight junctions of polarized epithelial cells, Exp. Cell Res., 300(1):134-48 (2004).
Brown et al., Metadherin, a cell surface protein in breast tumors that mediates lung metastasis, Cancer Cell, 5(4):365-74 (2004).
Buchwalter et al., PDEF promotes luminal differentiation and acts as a survival factor for ER-positive breast cancer cells, Cancer Cell, 23(6):753-67 (2013).
Chiaverotti et al., Dissociation of epithelial and neuroendocrine carcinoma lineages in the transgenic adenocarcinoma of mouse prostate model of prostate cancer, Am. J. Pathol., 172(1):236-46 (2008).
DeRose et al., Tumor grafts derived from women with breast cancer authentically reflect tumor pathology, growth, metastasis and disease outcomes, Nat. Med., 17(11):1514-20 (2011).
Ding et al., Telomerase reactivation following telomere dysfunction yields murine prostate tumors with bone metastases, Cell, 148(5):896-907 (2012).
Emdad et al., Activation of the nuclear factor kappaB pathway by astrocyte elevated gene-1: implications for tumor progression and metastasis, Cancer Res., 66(3):1509-16 (2006).
Emdad et al., AEG-1/MTDH/LYRIC: signaling pathways, downstream genes, interacting proteins, and regulation of tumor angiogenesis, Adv. Cancer Res., 120:75-111 (2013).
Emsley et al., Coot: model-building tools for molecular graphics, Acta. Crystallogr. D Biol. Crystallogr., 60 (Pt. 12 Pt 1):2126-32 (2004).
Foster et al., Characterization of prostatic epithelial cell lines derived from transgenic adenocarcinoma of the mouse prostate (TRAMP) model, Cancer Res., 57(16):3325-30 (1997).
Gao et al., Tudor-SN interacts with and co-localizes with G3BP in stress granules under stress conditions, FEBS Lett., 584(16):3525-32 (2010).

(Continued)

*Primary Examiner* — Sergio Coffa
(74) *Attorney, Agent, or Firm* — Marshall, Gerstein & Borun LLP

(57) ABSTRACT

The present disclosure related in general to methods of treating cancer by interfering with the interaction of metadherin with Staphylococcal nuclease domain-containing 1 (SND1) using peptides or other compounds that inhibit the binding of SND1 with metadherin and inhibit the activity of the MTDH-SND1 complex in tumor cells.

19 Claims, 36 Drawing Sheets

Specification includes a Sequence Listing.

(56) References Cited

OTHER PUBLICATIONS

Gelman, Suppression of tumor and metastasis progression through the scaffolding functions of SSeCKS/Gravin/AKAP12, Cancer Metastasis Rev., 31(3-4):493-500 (2012).
Ginestier et al., ALDH1 is a marker of normal and malignant human mammary stem cells and a predictor of poor clinical outcome, Cell Stem Cell, 1(5):555-67 (2007).
Gingrich et al., Metastatic prostate cancer in a transgenic mouse, Cancer Res., 56918):4096-102 (1996).
Gingrich et al., Pathologic progression of autochthonous prostate cancer in the TRAMP model, Prostate Cancer Prostatic Dis., 2(2):70-5 (1999).
Greenberg et al., Prostate cancer in a transgenic mouse, Proc. Natl. Acad. Sci. USA, 92(8):343943 (1995).
Guo et al., Slug and Sox9 cooperatively determine the mammary stem cell state, Cell, 148(5):1015-28 (2012).
Guo et al., Structural insights into the tumor-promoting function of the MTDH-SND1 complex, Cell Rep., 8(6):1704-13 (2014).
Halazonetis et al., An oncogene-induced DNA damage model for cancer development, Science, 319(5868):1352-5 (2008).
Herschkowitz et al., Identification of conserved gene expression features between murine mammary carcinoma models and human breast tumors, Genome Biol., 8(5):R76 (2007).
Hu et al., MTDH activation by 8q22 genomic gain promotes chemoresistance and metastasis of poor-prognosis breast cancer, Cancer Cell, 15(1):9-20 (2009).
Hurwitz et al., The TRAMP mouse as a model for prostate cancer, Curr. Protoc. Immunol., Chapter 20: Unit 20.5 (2001).
International Preliminary Report on Patentability, International Application No. PCT/US2015/037708, dated Dec. 27, 2016.
International Search Report and Written Opinion, International Application No. PCT/US2015/037708, dated Oct. 14, 2015.
Kaplan-Lefko et al., Pathobiology of autochthonous prostate cancer in a pre-clinical transgenic mouse model, Prostate, 55(3):219-37 (2003).
Kikuno et al., Knockdown of astrocyte-elevated gene-1 inhibits prostate cancer progression through upregulation of FOXO3a activity, Oncogene, 26(55):7647-55 (2007).
Kouros-Mehr et al., GATA-3 links tumor differentiation and dissemination in a luminal breast cancer model, Cancer Cell, 13(2):141-52 (2008).
Lento et al., Wnt signaling in normal and malignant hematopoiesis, Cold Spring Harb Perspect Biol., 5(2): a008011 (2013).
Li et al., Evidence that transgenes encoding components of the Wnt signaling pathway preferentially induce mammary cancers from progenitor cells, Proc. Natl. Acad. Sci. USA, 100(26):15853-8 (2003).
Li et al., Structural and functional insights into human Tudor-SN, a key component linking RNA interference and editing, Nucleic Acids Res., 36(11):3579-89 (2008).
Liu et al., Increased expression of metadherin protein predicts worse disease-free and overall survival in laryngeal squamous cell carcinoma, Int. J. Cancer, 133(3):671-9 (2013).
Mani et al., The epithelial-mesenchymal transition generates cells with properties of stem cells, Cell, 133(4):704-15 (2008).
McCoy et al., Phaser crystallographic software, J. Appl. Cryst., 40:658-74 (2007).
Meng et al., Cytoplasmic Metadherin (MTDH) provides survival advantage under conditions of stress by acting as RNA-binding protein, J. Biol. Chem., 287(7):4485-91 (2012).
Otwinowski et al., Processing of X-ray diffraction data collected in oscillation mode, Methods Enzymol., 276:307-26 (1997).
Perou et al., Molecular portraits of human breast tumours, Nature, 406(6797):747-52 (2000).
Sarkar et al., Molecular basis of nuclear factor-kappaB activation by astrocyte elevated gene-1, Cancer Res., 68(5):1478-84 (2008).
Shackleton et al., Generation of a functional mammary gland from a single stem cell, Nature, 439(7072):84-8 (2006).
Stryke et al., BayGenomics: a resource of insertional mutations in mouse embryonic stem cells, Nucleic Acids Res., 31(1):278-81 (2003).
Su et al., Identification and cloning of human astrocyte genes displaying elevated expression after infection with HIV-1 or exposure to HIV-1 envelope glycoprotein by rapid subtraction hybridization, RaSH, Oncogene, 21(22):3592-602 (2002).
Sundström et al., Tudor *staphylococcal* nuclease is an evolutionarily conserved component of the programmed cell death degradome, Nat. Cell Biol., 11(11):1347-54 (2009).
Sutherland et al., 3D3/lyric: a novel transmembrane protein of the endoplasmic reticulum and nuclear envelope, which is also present in the nucleolus, Exp. Cell Res., 294(1):94-105 (2004).
Taylor et al., Integrative genomic profiling of human prostate cancer, Cancer Cell, 18(1):11-22 (2010).
Thirkettle et al., LYRIC/AEG-1 is targeted to different subcellular compartments by ubiquitinylation and intrinsic nuclear localization signals, Clin. Cancer Res., 15(9):3003-13 (2009).
Vaillant et al., The mammary progenitor marker CD61/beta3 integrin identifies cancer stem cells in mouse models of mammary tumorigenesis, Cancer Res., 68(19):7711-7 (2008).
Van de Vijver et al., A gene-expression signature as a predictor of survival in breast cancer, N. Engl. J. Med., 347(25):1999-2009 (2002).
Vanharanta et al., Origins of metastatic traits, Cancer Cell, 24(4):410-21 (2013).
Wan et al., Genetic ablation of metadherin inhibits autochthonous prostate cancer progression and metastasis, Cancer Res., 74(18):5336-47 (2014).
Wan et al., MTDH-SND1 interaction is crucial for expansion and activity of tumor-initiating cells in diverse oncogene- and carcinogen-induced mammary tumors, Cancer Cell, 26(1):92-105 (2014).
Wan et al., Pleiotropic roles of AEG-1/MTDH/LYRIC in breast cancer, Adv. Cancer Res., 120:113-34 (2013).
Wan et al., Tumor metastasis: moving new biological insights into the clinic, Nat. Med., 19(11):1450-64 (2013).
Wang et al., Prognostic impact of Metadherin-SND1 interaction in colon cancer, Mol. Biol. Rep., 39(12):10497-504 (2012).
Weissbach et al., Tudor-SN and ADAR1 are components of cytoplasmic stress granules, RNA, 18(3):462-71 (2012).
Winn et al., Overview of the CCP4 suite and current developments, Acta Crystallogr. D Biol. Crystallogr., 67(Pt. 4):235-42 (2011).
Xing et al., Inhibiting metadherin/SND1 interaction to treat cancer, Wisconsin Alumni Research Foundation, downloaded from the Internet at: <www.warf.org/documents/technology-summary/P140424US01.pdf> (admitted prior art).
Yin et al., Characterization of medroxyprogesterone and DMBA-induced multilineage mammary tumors by gene expression profiling, Mol. Carcinog., 44(1):42-50 (2005).
Yoo et al., Astrocyte elevated gene-1 regulates hepatocellular carcinoma development and progression, J. Clin. Invest., 119(3):465-77 (2009).
Yoo et al., Increased RNA-induced silencing complex (RISC) activity contributes to hepatocellular carcinoma, Hepatology, 53(5):1538-48 (2011).
Yu et al., Metadherin regulates metastasis of squamous cell carcinoma of the head and neck via AKT signalling pathway-mediated epithelial-mesenchymal transition, Cancer Lett., 343(2):258-67 (2014).
Zhang et al., A NIK-IKKa module expands ErbB2-induced tumor-initiating cells by stimulating nuclear export of p27/Kip1, Cancer Cell, 23(5):647-59 (2013).
Zhang et al., A renewable tissue resource of phenotypically stable, biologically and ethnically diverse, patient-derived human breast cancer xenograft models, Cancer Res., 73(15):4885-97 (2013).
Zhu et al., Metadherin promotes hepatocellular carcinoma metastasis through induction of epithelial-mesenchymal transition, Clin. Cancer Res., 17(23):7294-302 (2011).

\* cited by examiner

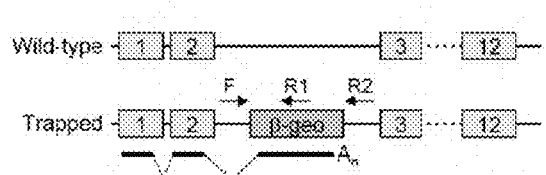
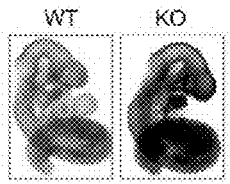
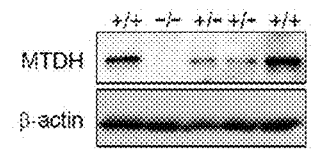
FIG. 1A  FIG. 1B  FIG. 1C
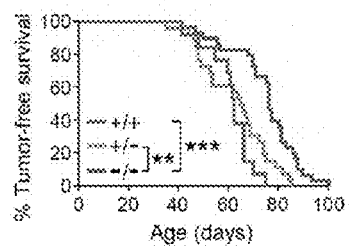 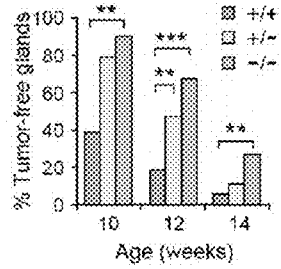 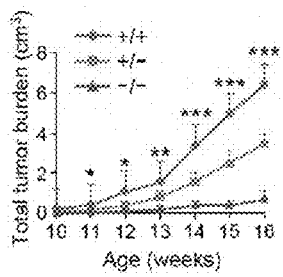 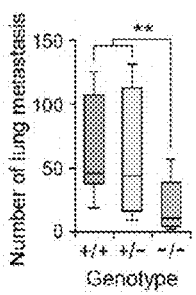
FIG. 1D  FIG. 1E  FIG. 1F  FIG. 1G
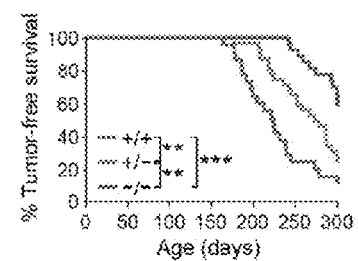 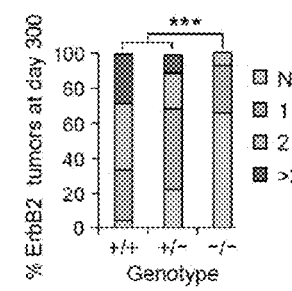 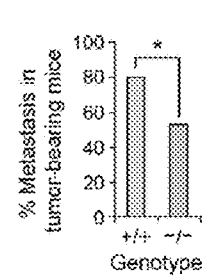 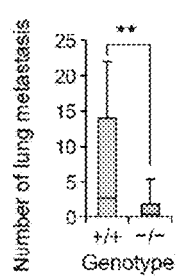
FIG. 1H  FIG. 1I  FIG. 1J  FIG. 1K
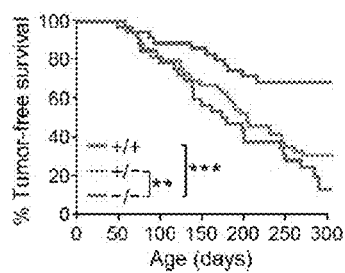 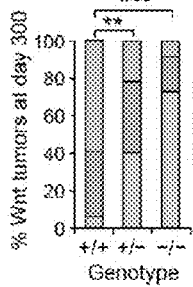 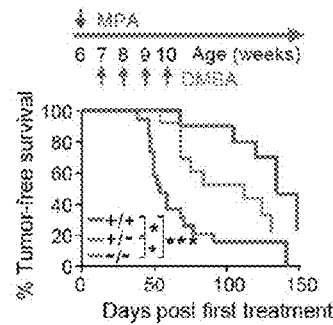 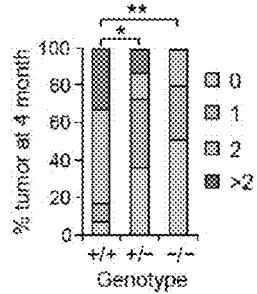
FIG. 1L  FIG. 1M  FIG. 1N  FIG. 1O

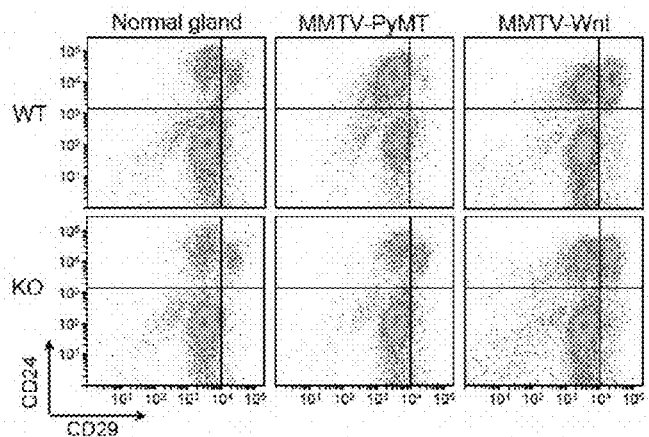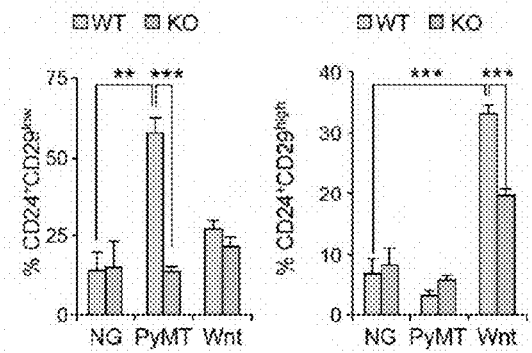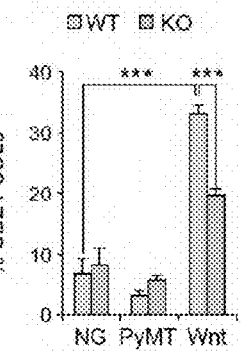
FIG. 2A  FIG. 2B  FIG. 2C
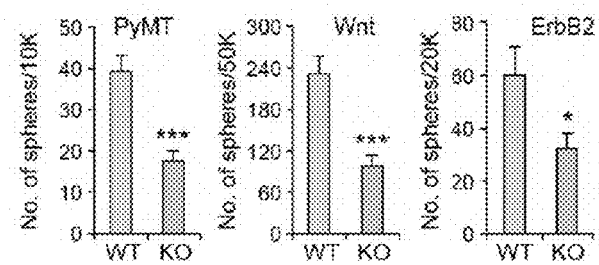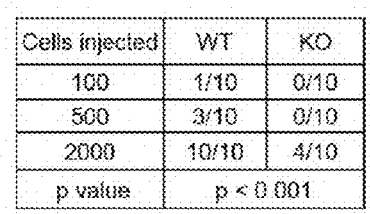
FIG. 2D  FIG. 2E
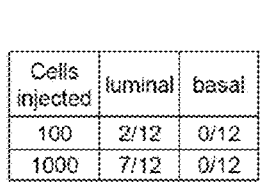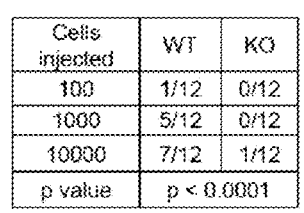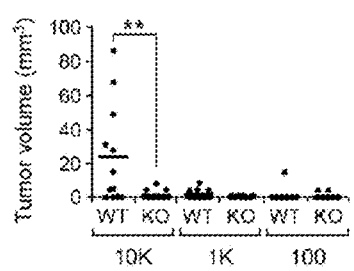
FIG. 2F  FIG. 2G  FIG. 2H

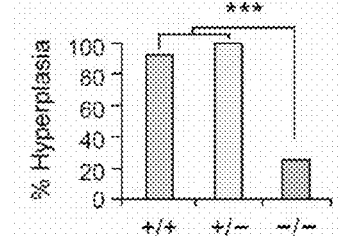
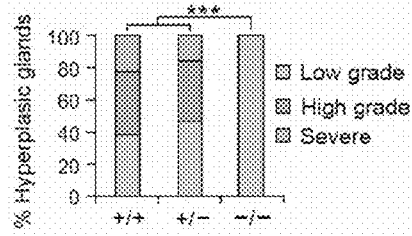
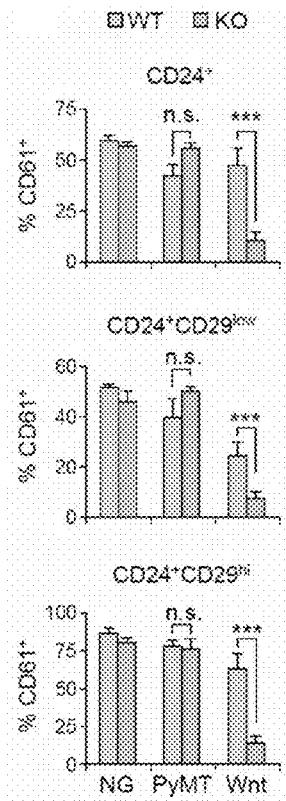
FIG. 3A
FIG. 3B
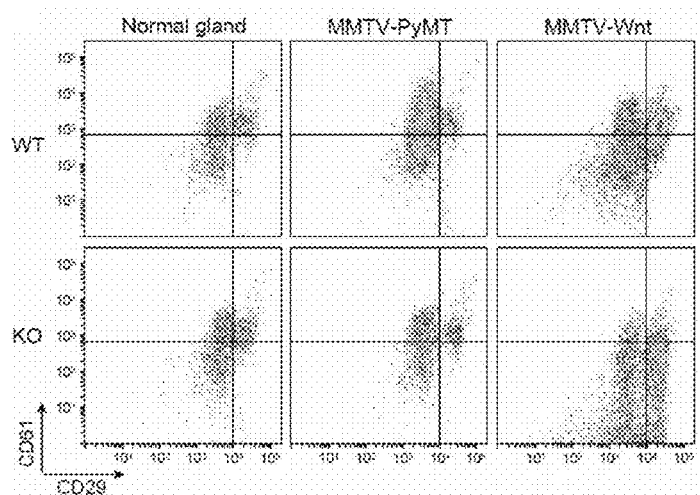
FIG. 3C
FIG. 3D
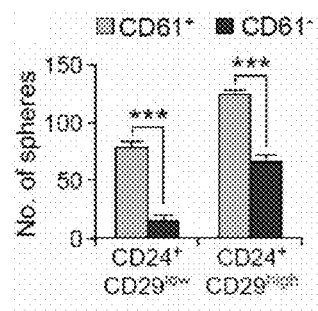
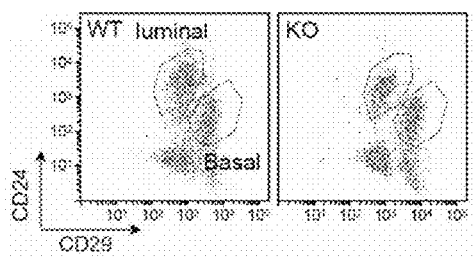
FIG. 3E
FIG. 3F

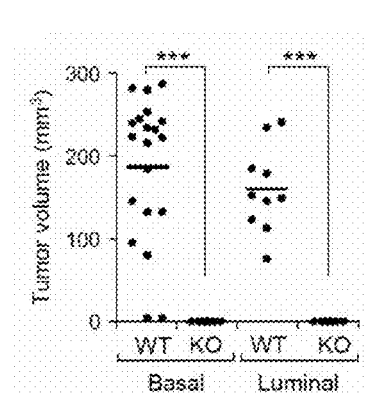
FIG. 3G
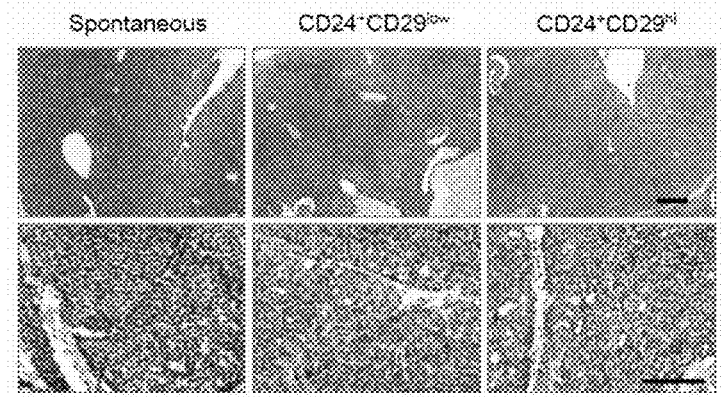
FIG. 3H
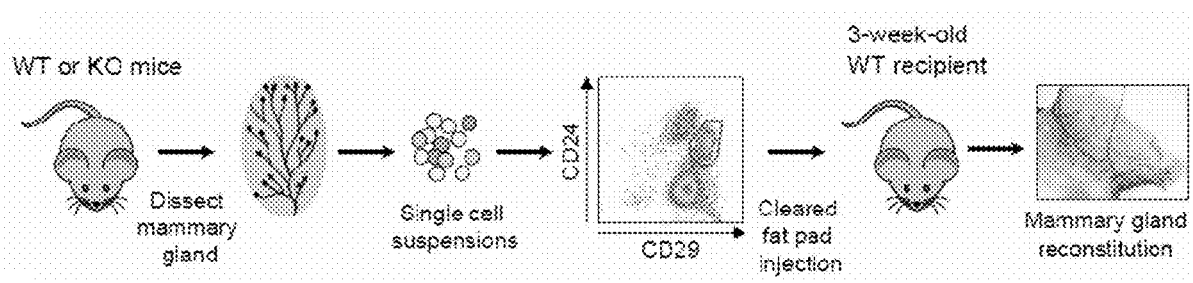
FIG. 3I
| Lin⁻ MECs | Take rate (p = 0.369) | |
|---|---|---|
| No. of cells injected | WT | KO |
| 10000 | 62.5%(10/16) | 52.9%(9/17) |
| 5000 | 64%(16/25) | 60%(15/25) |
| 2000 | 31.2%(5/16) | 18.7%(3/16) |
| 400 | 0 (0/8) | 0 (0/8) |
| Repopulating frequency (95% interval) | 1/6711 (1/4616-1/9757) | 1/8609 (1/5809-1/12759) |
FIG. 3J

| CD24$^+$CD29$^{hi}$ | Take rate (p = 0.376) | |
| --- | --- | --- |
| No. of cells injected | WT | KO |
| 1000 | 85%(17/20) | 90%(18/20) |
| 500 | 72.7%(16/22) | 77.37%(17/22) |
| 100 | 41.7%(10/24) | 52.2%(12/23) |
| Repopulating frequency (95% interval) | 1/375 (1/262-1/535) | 1/298 (1/207-1/429) |

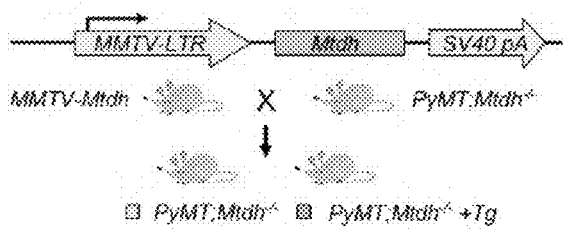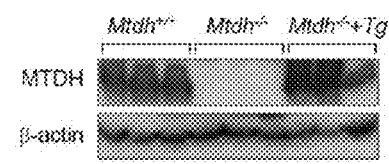
FIG. 4A                FIG. 4B
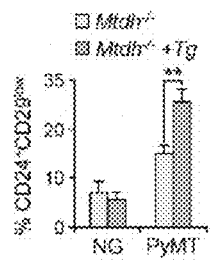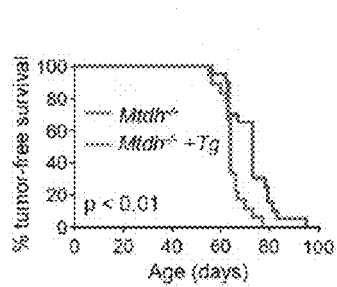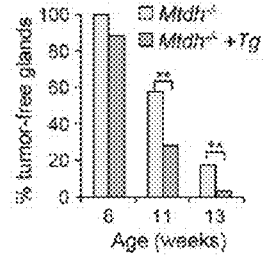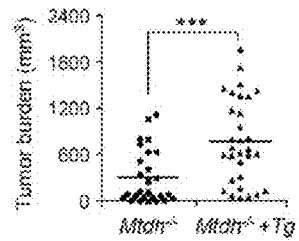
FIG. 4C     FIG. 4D     FIG. 4E     FIG. 4F
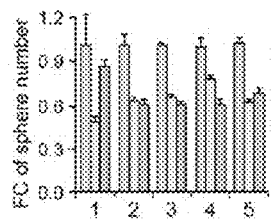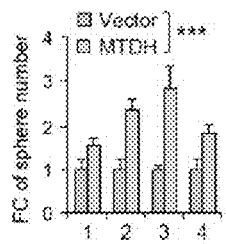
FIG. 4G     FIG. 4H     FIG. 4I     FIG. 4J
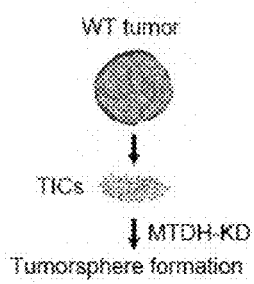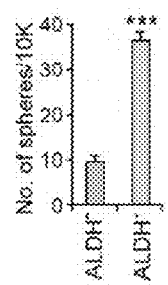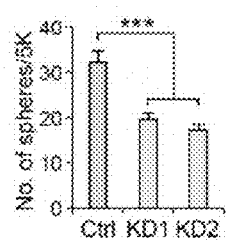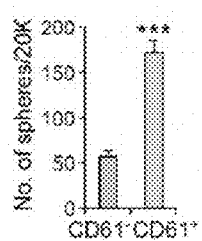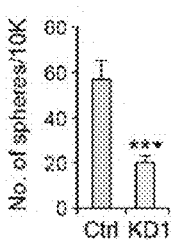
FIG. 4K     FIG. 4L     FIG. 4M     FIG. 4N     FIG. 4O

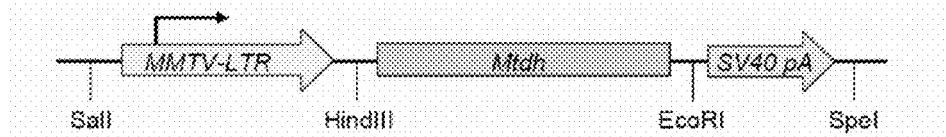
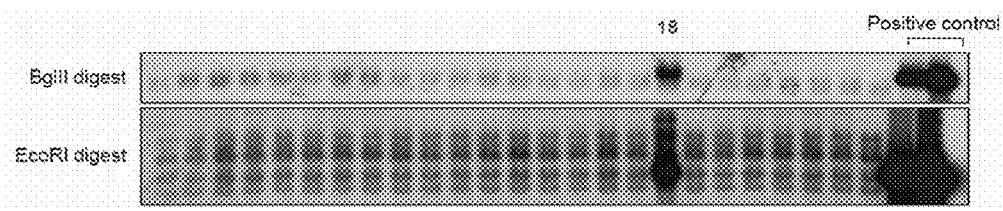
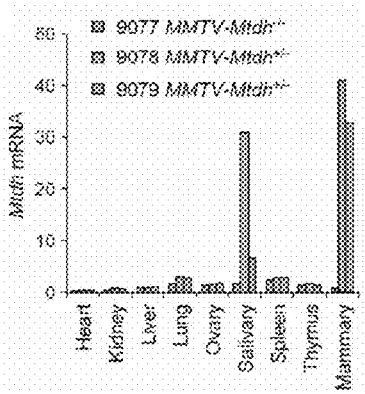
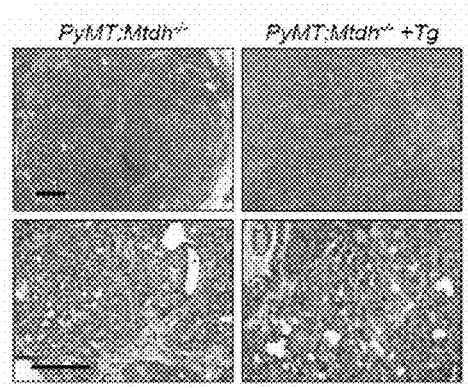
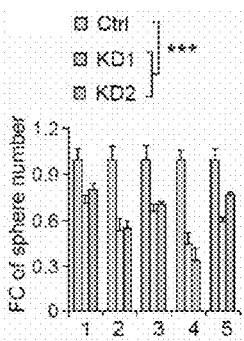
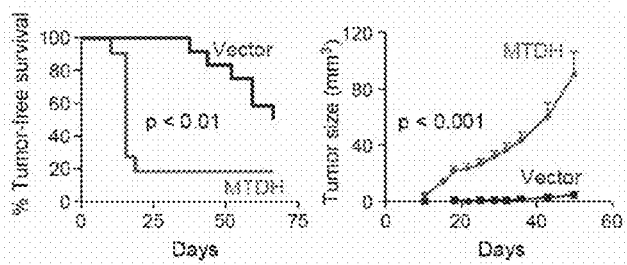
FIG. 5A
FIG. 5B
FIG. 5C
FIG. 5D
FIG. 5E
FIG. 5F
FIG. 5G
FIG. 5H

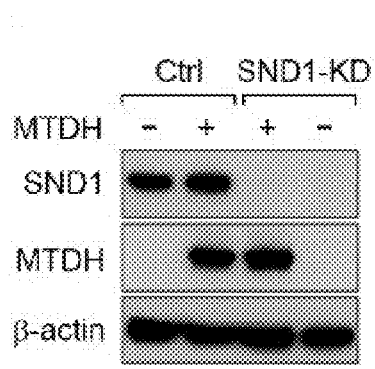
FIG. 6A
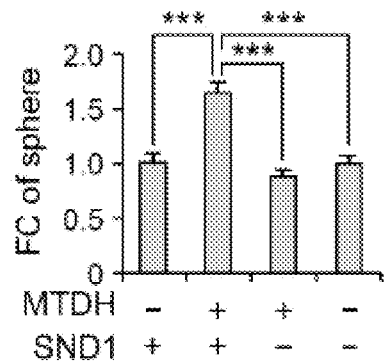
FIG. 6B
| Cells injected | MTDH⁻ SND1⁺ | MTDH⁺ SND1⁺ | MTDH⁺ SND1⁻ | MTDH⁻ SND1⁻ |
|---|---|---|---|---|
| 125 | 1/10 | 5/10 | 0/10 | 0/10 |
| 500 | 3/10 | 8/10 | 2/10 | 1/10 |
| p value (vs.MTDH⁺ SND1⁺) | 0.0049 | / | 0.0017 | 0.0025 |
FIG. 6C
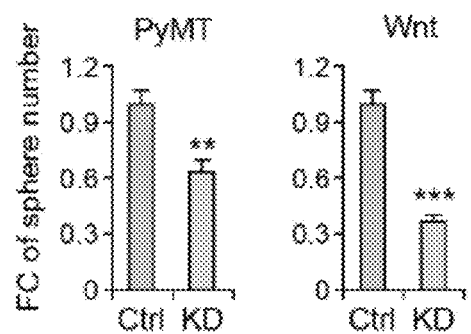
FIG. 6D
| Cells injected | Control | SND1 KD |
|---|---|---|
| 1000 | 10/10 | 10/10 |
| 250 | 10/10 | 4/10 |
| 50 | 3/10 | 1/10 |
| p value | 0.0001 | |
FIG. 6E
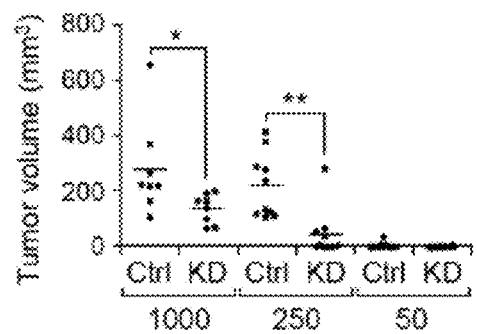
FIG. 6F

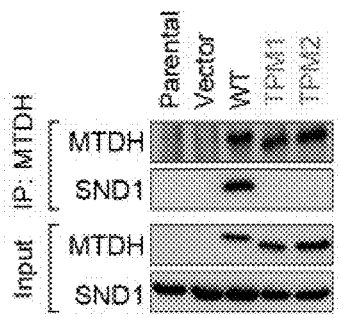
FIG. 8A
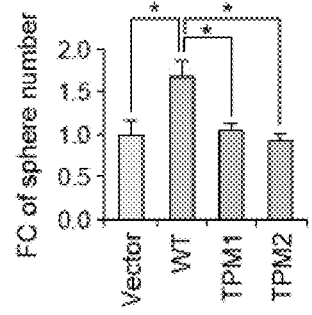
FIG. 8B
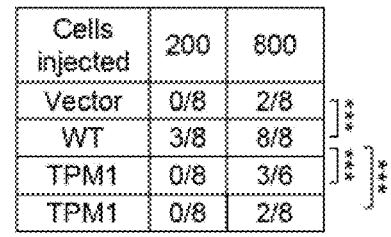
FIG. 8C
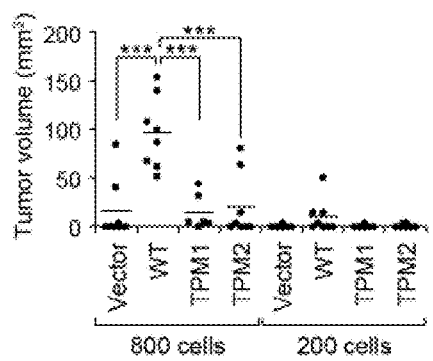
FIG. 8D
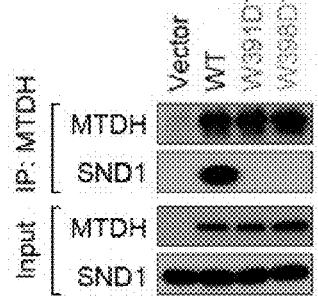
FIG. 8E
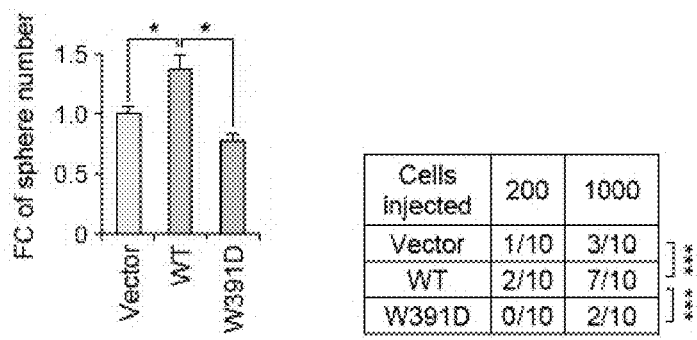
FIG. 8F
FIG. 8G
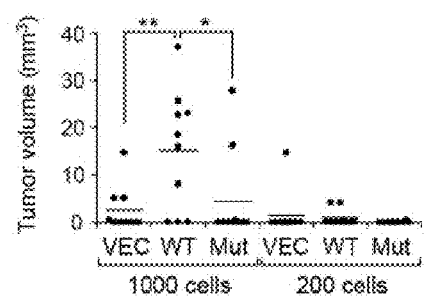
FIG. 8H

| Molecular and cellular functions | p value | # of molecules |
|---|---|---|
| Cell death and survival | 6.77E-08 – 1.27E-02 | 137 |
| Cell cycle | 9.59E-23 – 1.25E-02 | 111 |
| Cellular assembly and organization | 9.59E-23 – 1.25E-02 | 94 |
| DNA replication, recombination, and repair | 9.59E-23 – 1.29E-02 | 89 |
| Cellular movement | 2.28E-09 – 1.29E-02 | 33 |

FIG. 9G

| Functional annotation | p value | Predicted activation state | Activation z-score |
|---|---|---|---|
| Cell survival | 6.51E-04 | Increased | 5.253 |
| Cell viability | 2.62E-03 | Increased | 4.834 |
| Cell viability of tumor cell lines | 3.79E-03 | Increased | 2.664 |
| Cell viability of myeloma cell lines | 2.87E-05 | Increased | 2.345 |
| Cell viability of cancer cells | 6.49E-03 | Increased | 2.238 |
| Cell viability of embryonic cell lines | 1.95E-05 | Increased | 2.138 |
| Apoptosis | 6.77E-08 | | -1.496 |
| Cell death | 9.97E-07 | | -1.59 |

FIG. 9H

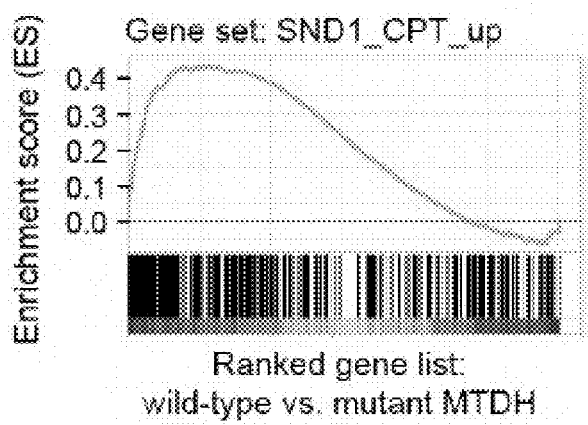

FIG. 9I

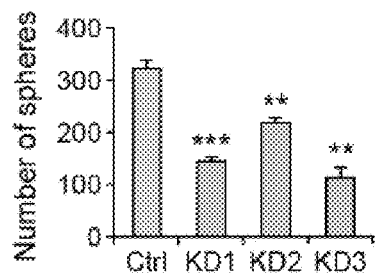 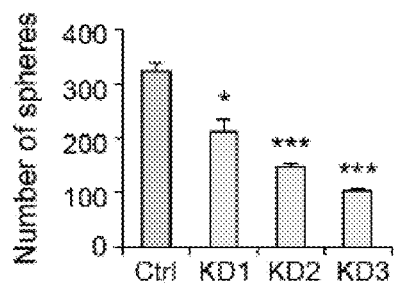 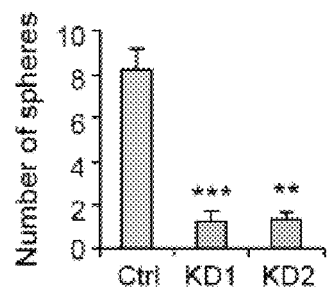
FIG. 10A      FIG. 10B      FIG. 10C
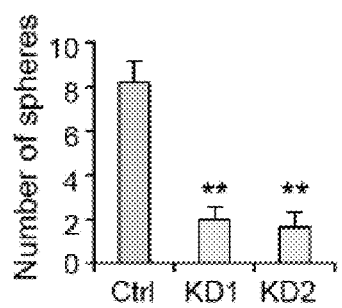 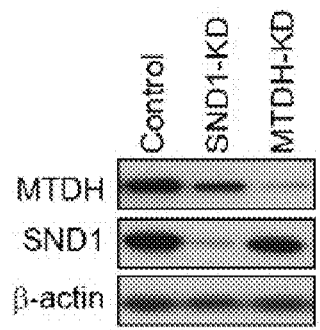 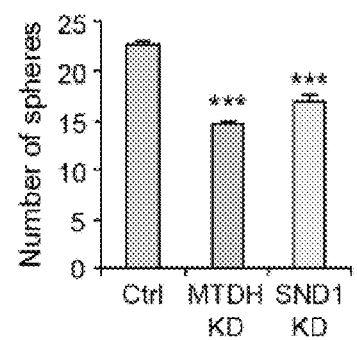
FIG. 10D      FIG. 10E      FIG. 10F
| Cells injected | 10K | 100K |
|---|---|---|
| Control | 3/10 | 10/10 |
| MTDH-KD | 0/10 | 6/10 |
| SND1-KD | 0/10 | 7/10 |
FIG. 10G
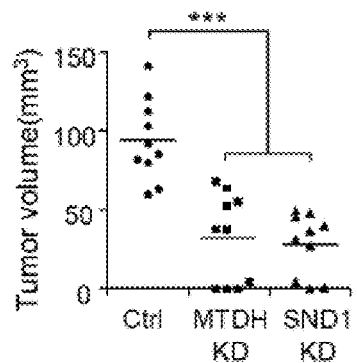
FIG. 10H

| MTDH \ SND1 | Neg | Weak | Moderate | Strong |
|---|---|---|---|---|
| Neg | 2 | 6 | 0 | 0 |
| Weak | 0 | 15 | 30 | 7 |
| Moderate | 0 | 6 | 35 | 16 |
| Strong | 0 | 0 | 11 | 26 |
| | p < 0.0001 | | | |
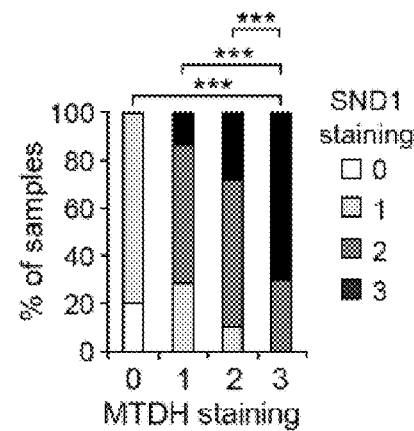
FIG. 10I
FIG. 10J
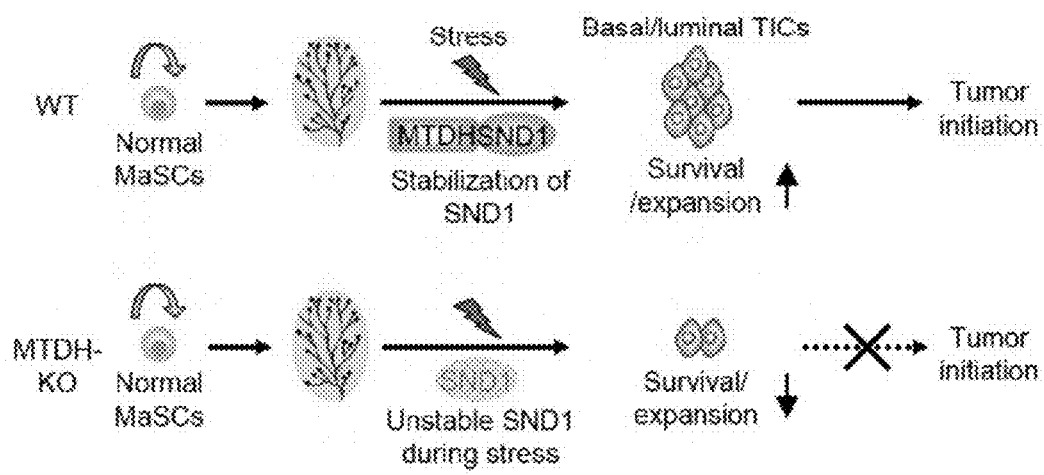
FIG. 10K

| MTDH \ SND1 | Neg | Weak | Moderate | Strong |
|---|---|---|---|---|
| Neg | 20 | 4 | 0 | 2 |
| Weak | 13 | 16 | 5 | 5 |
| Moderate | 20 | 11 | 12 | 7 |
| Strong | 19 | 30 | 46 | 60 |
| | \multicolumn{4}{c}{$p < 0.0001$} | | | |
FIG. 11G
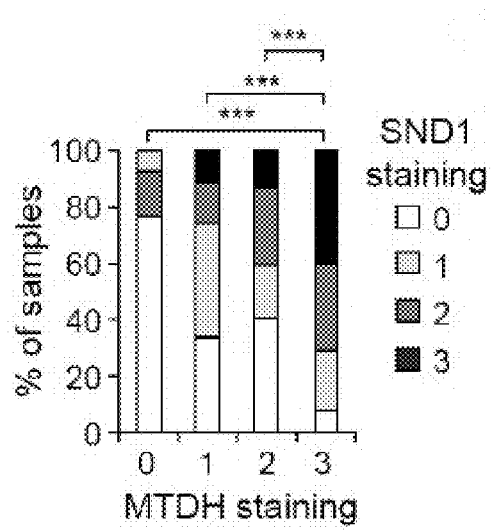
FIG. 11H
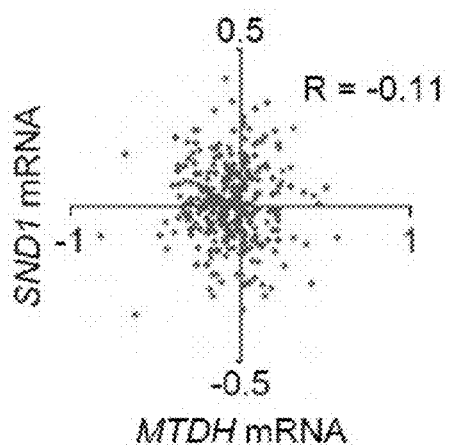
FIG. 11I

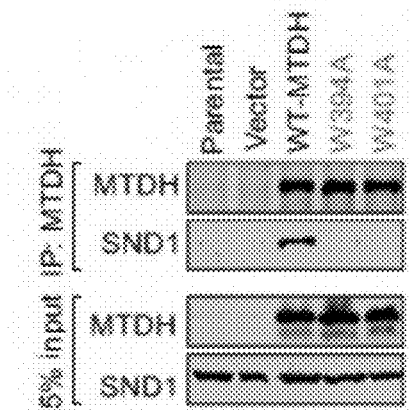
FIG. 23A
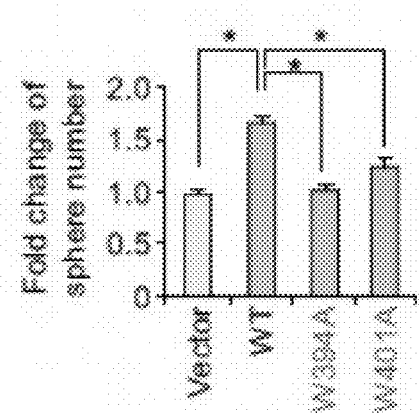
FIG. 23B
| Tumor incidence | | | | |
|---|---|---|---|---|
| Cells injected | Control | WT-MTDH | W394A | W401A |
| 100 cells | 4/10 | 9/10 | 3/10 | 5/10 |
| 1000 cells | 10/10 | 10/10 | 9/10 | 8/10 |
| TIC frequency | 1/284 | 1/66 | 1/546 | 1/576 |
| p values (vs. WT-MTDH) | p =0.0153 | N.A. | p < 0.001 | p < 0.001 |
FIG. 23C
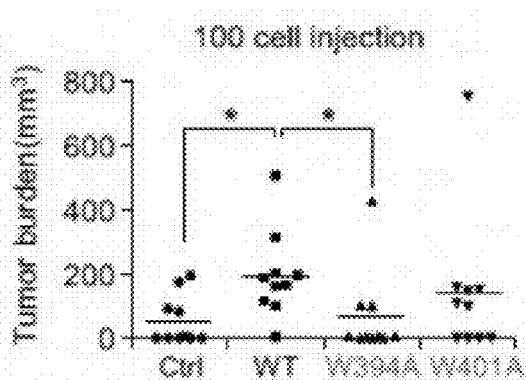
FIG. 23D
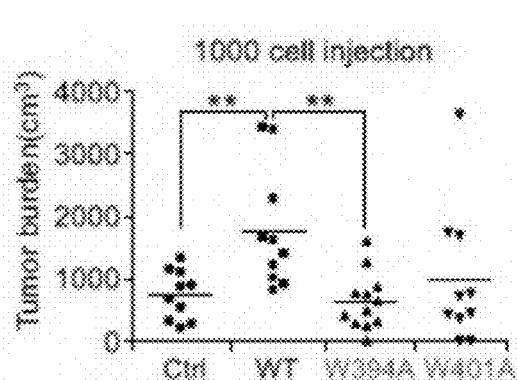
FIG. 23E

USE OF PEPTIDES THAT BLOCK METADHERIN-SND1 INTERACTION AS TREATMENT FOR CANCER

RELATED PATENT APPLICATIONS

This application is a divisional of U.S. patent application Ser. No. 15/321,337, filed Dec. 22, 2016, now U.S. Pat. No. 10,357,539, issued Jul. 23, 2019, which is a National Phase Application of PCT/US2015/037708, filed Jun. 25, 2015, which claims the benefit of priority to U.S. Provisional Patent application No. 62/016,947, filed Jun. 25, 2014, the disclosure of which is incorporated herein by reference in its entirety.

GOVERNMENT GRANT

This invention was made with government support under Grant Number R01CA134519 and R01GM096060 awarded by the National Institutes of Health. The government has certain rights in the invention.

FIELD OF THE INVENTION

The present disclosure relates to methods of treating cancer and reducing tumor growth, recurrence and metastasis comprising administering an inhibitor that blocks the interaction of metadherin (MTDH) and Staphylococcal nuclease domain-containing 1 (SND1) and inhibits the function of the MTDH-SND1 complex. It is contemplated that the inhibitors include peptides or fragments of MTDH that bind SND1 or peptides or fragments derived from SND1 that bind metadherin.

INCORPORATION BY REFERENCE

Incorporated by reference in its entirety is a computer-readable nucleotide/amino acid sequence listing submitted concurrently herewith and identified as follows: ASCII text file named "48166_SeqListing.txt"; 17,037 bytes; created Jun. 24, 2015.

BACKGROUND OF THE INVENTION

Cancer is characterized by rampant genetic and epigenetic alterations. Recurrent DNA copy number alterations often indicate the presence of key drivers of cancer in the affected loci. Metadherin (MTDH; also called AEG1, LYRIC) has previously been identified as a pro-metastasis gene that resides in 8q22, a frequently amplified genomic locus linked to poor relapse-free survival of breast cancer (Hu et al., 2009). Overexpression of MTDH is observed in more than 40% of primary tumors and is an independent poor-prognosis factor (Hu et al., 2009). What drives the strong selection of MTDH in primary breast tumors is unclear and the functional significance of MTDH in normal development and tumorigenesis remains poorly understood.

Recent studies using cell culture or xenograft models have implicated MTDH in several cancer-related processes, including proliferation, cell death, invasion, and angiogenesis (Emdad et al., 2013), although the underlying mechanistic understanding of MTDH in these processes remains limited to date. In breast cancer, MTDH was postulated to be a transmembrane protein that mediates the adhesion of cancer cells to the lung endothelium (Brown and Ruoslahti, 2004). In certain cancer types, MTDH has been linked to multiple oncogenic pathways such as PI3K/AKT and NF-κB (Emdad et al., 2013). How MTDH regulates these pathways remains elusive. Although evolutionarily conserved in higher vertebrates, MTDH contains no recognizable functional domain, rendering the understanding of its biological function challenging. Multiple groups have identified several MTDH-binding partners, including PLZF, BCCIPα and Staphylococcal nuclease domain-containing 1 (SND1) (Wan and Kang, 2013). However, whether and how the interactions with these proteins mediate the function of MTDH is largely unknown.

Breast cancer is a heterogeneous disease that can be broadly classified into luminal and basal-like subtypes based on gene expression profiles (Perou et al., 2000). It has been speculated that different oncogenic signaling may target different cells of origin, thus leading to the formation of different subtypes of breast cancer. However, the origin, identity and regulation of tumor-initiating cells (TICs) in different oncogene-induced mammary tumors remain poorly characterized. Autochthonous tumorigenesis in mice offers great models for tracking the early changes during tumor initiation and for investigating the role of a gene of interest in mediating the transformation and expansion of TICs.

SUMMARY

The present disclosure has shown that metadherin (MTDH) is important for the expansion and function of both luminal and basal breast tumor initiating cells (TICs) and prostate tumors, and underscores the selection pressure to overexpress MTDH in diverse tumor subtypes. The functional dependency of MTDH on its conserved interaction with SND1 suggests that targeting the MTDH-SND1 complex may offer an opportunity to control tumor initiation, recurrence and metastasis by preventing the expansion of TICs, with minimal impact on normal tissues.

The disclosure provides a method for preventing or reducing the recurrence or expansion of tumor initiating cells in a subject comprising administering an agent that interferes with the interaction of MTDH and SND1. The disclosure also provides a method for treating cancer in a subject having cancer comprising administering to the subject an inhibitor that disrupts the interaction between MTDH and SND1.

In various embodiments, the inhibitor binds to a region of human MTDH within residues 364-582 of MTDH (such as amino acids 364-407 of MTDH) set forth in SEQ ID NO: 1. In some embodiments, the inhibitor binds SND1 SN1/2 domains. In some embodiments, the inhibitor binds to a region of human SND1 within residues 16-339 of SND1 (such as amino acids 39-43 of SND1) set forth in SEQ ID NO: 2. In various embodiments, the disclosure provides a method for reducing or decreasing the expansion of tumor initiating cells in a subject comprising administering an inhibitor of the interaction between metadherin (MTDH) and Staphylococcal nuclease domain-containing 1 (SND1) wherein the inhibitor inhibits SND1 protein interaction within residues 364 to 407 of metadherin (SEQ ID NO: 1).

In various embodiments, the subject has cancer. Exemplary cancers contemplated herein include, but are not limited to breast cancer, prostate cancer, liver cancer, lung cancer, colon cancer, colorectal cancer, non-small cell lung carcinoma, squamous cell carcinoma, cervical cancer, bladder cancer, as well those listed in the Detailed Description. In various embodiments, the cancer is selected from the group consisting of breast cancer and prostate cancer. In some embodiments, the cancer is liver cancer.

It is contemplated that the MTDH/SND1 inhibitor is a peptide of MTDH, a peptide of SND1, a peptide mimetic having similar structure as a peptide comprising residues 393-403 of MTDH, a small molecule compound that has similar structure or part of the structure as a peptide comprising residues 393-403 of MTDH, or a nanoparticle conjugate containing a peptide or peptide mimetic described herein.

In various embodiments, the inhibitor is a peptide. For example, in various embodiments, the peptide comprises the consensus sequence XWXXXXXXWXX (SEQ ID NO: 3), where X is any amino acid. In various embodiments, the peptide comprises the consensus sequence XWXXXXXX-WXX (SEQ ID NO: 3) from residues 393-403 of MTDH (SEQ ID NO: 2), where X is any amino acid. In various embodiments, the inhibitor is a peptide comprising the consensus sequence XWXXXXXXWXX (SEQ ID NO: 4), where X is any amino acid. In various embodiments, the inhibitor is a peptide of MTDH selected from i) a peptide within residues 364-582 of MTDH, ii) a peptide within residues 364-407 of MTDH, iii) a peptide comprising residues 386-407 of MTDH, or iv) a peptide comprising residues 393-403 of MTDH. In various embodiments, the inhibitor is a peptide of MTDH selected from i) a peptide consisting essentially of residues 364-582 of SEQ ID NO: 1, ii) a peptide having residues 364-407 of MTDH, iii) a peptide consisting essentially of residues 386-407 of SEQ ID NO: 1, or iv) a peptide consisting essentially of residues 393-403 of SEQ ID NO: 1. In some embodiments, the peptide is a variant of any of the wild type MTDH peptides described herein, wherein the variant peptide retains W394 and W401, wherein the position is based on the amino acid sequence of wild type MTDH (i.e., SEQ ID NO: 1).

In various embodiments, the peptide comprises the sequence of DWNAPAEEWGN (SEQ ID NO: 5), or a variant thereof, wherein the variant peptide comprises at least one (such as any of 2, 3, 4, 5, 6, 7, 8, or 9) mutations at any position except for the W residues. In some embodiments, the peptide is about 11 to about 22 amino acids long (such as about 15 to about 22 amino acids long). In some embodiments, the peptide comprises about any of 1, 2, 3, 4, 5, 6, or 7 amino acids N-terminal to the sequence of DWNAPAEEWGN (SEQ ID NO: 5), or a variant thereof. In some embodiments, the peptide comprises about any of 1, 2, 3, or 4 amino acids C-terminal to the sequence of DWNA-PAEEWGN (SEQ ID NO: 5), or a variant thereof. In some embodiments, the peptide comprises the sequence of DWNAPEEWGN (SEQ ID NO: 20), or a variant thereof, wherein the variant peptide comprises at least one (such as any of 2, 3, 4, 5, 6, 7, 8, or 9) mutations at any position except for the W residues. In some embodiments, the peptide is about 10 to about 21 amino acids long (such as about 14 to about 21 amino acids long). In some embodiments, the peptide comprises about any of 1, 2, 3, 4, 5, 6, or 7 amino acids N-terminal to the sequence of DWNAPEEWGN (SEQ ID NO: 20), or a variant thereof. In some embodiments, the peptide comprises about any of 1, 2, 3, or 4 amino acids C-terminal to the sequence of DWNAPEEWGN (SEQ ID NO: 20), or a variant thereof.

In various embodiments, the peptide comprises a mutation in MTDH at one or more amino acid residues selected from the group consisting of D389, A392, D393, N395, E399, E400, W404, D406 and E407, wherein the amino acid position is based on the wild type MTDH sequence (i.e., SEQ ID NO: 1). In various embodiments, the peptide comprises a mutation in MTDH at one or more residues selected from the group consisting of D389R, D393R, E399R, E400R, W404D, D406R and E407R, wherein the position is based on the wild type MTDH sequence (i.e., SEQ ID NO: 1). In various embodiments, the mutation is selected from the group consisting of D389R, D393R, E399R, E400R, W404D, D406R and E407R of SEQ ID NO: 1.

In various embodiments, the inhibitor is a peptide of SND1 within residues 16 to 339 of SND1 (i.e., SEQ ID NO: 2). In one embodiment, the SND1 peptide comprises a mutation at one or more residues selected from the group consisting of F250, R324, R255, R327, R324, P39, P43, E247, L256, H279, I284, L287, R259 and N281, wherein the position is based on the wild type SND1 sequence (i.e., SEQ ID NO: 2). In various embodiments, the mutation in SND1 is selected from the group consisting of F250A R324E and R255E of SEQ ID NO: 2.

It is contemplated herein that the inhibitor peptide is part of a fusion protein. In certain embodiments, the peptide is fused to an FC domain.

The disclosure also provides compositions (such as pharmaceutical compositions) comprising an MTDH/SND1 inhibitor described herein and a pharmaceutically acceptable carrier. Also provided are isolated peptides inhibitors (such as any one of the peptides described herein). The present application further provides methods of making and using any one of the peptide inhibitors (as well as compositions comprising such peptide inhibitors) described herein.

Thus, for example, in some embodiments, there is provided a method of disrupting the interaction between MTDH and SND1 in a subject, comprising administering to the subject any one of the peptide inhibitors (or pharmaceutical compositions comprising such peptide inhibitors) described above. In some embodiments, there is provided a method of inhibiting SND1-dependent expression of prosurvival genes in a subject, comprising administering to the subject any one of the peptide inhibitors (or pharmaceutical compositions comprising such peptide inhibitors) described above.

Also contemplated are animals useful for studying the inhibitors of MTDH and SND1, including MTDH knockout and knockdown models described herein as well as SND1 knockdown models described herein.

Also contemplated is the crystal structure of the binding between MTDH and SND1 which is useful for identifying inhibitors of the interaction between MTDH and SND1.

BRIEF DESCRIPTION OF THE DRAWINGS

FIGS. 1A-O shows systemic deletion of Mtdh inhibits mammary tumor formation and metastasis. (FIG. 1A) Schematic representation of WT and mutant Mtdh allele. Green boxes represent exons 1-12. Primers (F, forward; R, reverse) used for genotyping are indicated above the corresponding genomic sequences. (FIG. 1B) LacZ expression in WT and KO embryo at day 10.5, visualized by X-gal staining. (FIG. 1C) MTDH protein immunobloting in MECs freshly dissociated from 8-week-old female mice with indicated Mtdh genotype. (FIG. 1D) Kinetics of mammary tumor onset in MMTV-PyMT females of indicated Mtdh genotypes. Mtdh+/+ (n=13), Mtdh+/− (n=26) and Mtdh−/− (n=30). (FIG. 1E) Percentage of tumor-free mammary glands at indicated ages in the same cohort of mice as in (FIG. 1D). (FIG. 1F) Total tumor burden of PyMT;Mtdh+/+, PyMT; Mtdh+/− and PyMT;Mtdh−/− cohorts evaluated at indicated age. Statistical comparison was done between Mtdh+/+ and Mtdh−/− groups. Data represent mean±SEM (n>20). (FIG. 1G) Number of lung metastatic nodules in PyMT;Mtdh+/+ (n=15), PyMT;Mtdh+/− (n=11) and PyMT;Mtdh−/− (n=14)

animals. Error bars represent 5-95 percentiles. (H) Kinetics of mammary tumor onset in MMTV-ErbB2 mice of the indicated genotypes. Mtdh+/+ (n=22), Mtdh+/− (n=31) and Mtdh−/− (n=27). (FIG. 1I) Percentage of mice from same cohorts as in (FIG. 1H) bearing indicated number of tumors at 300 days of age. (FIG. 1J) Incidence of lung metastasis in tumor-bearing MMTV-ErbB2 mice from Mtdh+/+ (n=30) and Mtdh−/− (n=23) groups. (FIG. 1K) Number of metastatic lesions per lung section in the same cohorts of mice from (FIG. 1J). Error bars represent 5-95 percentiles. (FIG. 1L) Kinetics of mammary tumor onset in MMTV-Wnt mice of the indicated genotypes. Mtdh+/+ (n=31), Mtdh+/− (n=48) and Mtdh−/− (n=31). (FIG. 1M) Percentage of mice from same cohorts as in (L) bearing indicated number of tumors at 300 days of age. (FIG. 1N) Kinetics of mammary tumor onset in mice with indicated Mtdh genotype treated with MPA and DMBA as indicated (top). Tumor latency was recorded as days after first DMBA treatment. Mtdh+/+ (n=19), Mtdh+/− (n=13) and Mtdh−/− (n=10). (FIG. 1O) Percentage of mice from same cohorts as in (FIG. 1N) bearing indicated number of tumors at 4 months of age. Statistics: (FIG. 1D, FIG. 1H, FIG. 1L, FIG. 1N) log rank test. (FIG. 1E, FIG. 1I, FIG. 1J, FIG. 1M, FIG. 1O) Chi-square test. (FIG. 1G, FIG. 1K) Mann-Whitney test. (FIG. 1F) Student's t-test. *$p<0.001$, $p<0.01$, *$p<0.05$.

FIGS. 2A-H shows that mammary glands from Mtdh−/− mice exhibit defects in oncogene-induced expansion and tumorigenic potential. (FIG. 2A) Flow cytometry of CD45−CD31−TER119− (Lin−) MECs from mammary glands of 6-week-old females of the indicated genotypes. (FIG. 2B, FIG. 2C) Quantification of luminal (FIG. 2B) and basal (FIG. 2C) cells analyzed in (FIG. 2A) (n=4). (FIG. 2D) Mammosphere formation assays with WT or KO MECs dissociated from preoeplastic glands of MMTV-PyMT (n=6), MMTV-Wnt (n=4), MMTV-ErbB2 (n=6) mice. Assays performed in triplicates for each mammary gland. (FIG. 2E) Mammary tumor incidence (left) and size (right) 3 months after orthotopic transplantations of unsorted MECs dissociated from preneoplastic glands of PyMT;Mtdh+/+ and PyMT;Mtdh−/− mice. (FIG. 2F) Mammary tumor incidence (left) and size (right) 8 weeks after orthotopic transplantations of indicated sorted CD24+CD29low luminal or CD24+CD29high basal MECs from preneoplastic glands of PyMT;Mtdh+/+ mice. (FIG. 2G, FIG. 2H) Mammary tumor incidence (FIG. 2G) and volumes (FIG. 2H) 8 weeks after orthotopic transplantations of Lin−CD24+CD29low luminal cells from preneoplastic glands of PyMT;Mtdh+/+ and PyMT;Mtdh−/− mice. Statistics: (FIG. 2B-D) Student's t-test. (FIG. 2E-H), tumor incidence based on limiting dilution analysis and tumor volume based on Mann-Whitney test. *$p<0.001$, $p<0.01$, *$p<0.05$. Data represent mean±SEM.

FIGS. 3A-L also shows that MTDH is required for the activities of oncogene-induced luminal and basal TICs but not MaSCs. (FIG. 3A, FIG. 3B) Incidence (FIG. 3A) and severity (B) of hyperplasia in tumor-free mammary glands from 6-month-old ErbB2;Mtdh+/+ (n=14), ErbB2;Mtdh+/− (n=26), and ErbB2;Mtdh−/− (n=16) mice. (FIG. 3C) Flow cytometry of CD45−CD31−TER119−CD24+MECs from mammary glands of 6-week-old females of the indicated genotypes using CD29 and CD61 markers. Note, this was the same batch experiment as shown in FIG. 3B. (FIG. 3D) Percentage of CD61+ cells in CD24+(upper panel), CD24+CD29low luminal cells (middle panel) and CD24+CD29hi basal cell (lower panel) analyzed in (FIG. 3A) (n=4). Data represent mean±SEM. (FIG. 3E) Mammosphere forming assays of CD61+ or CD61− cells from indicated cell populations dissociated from Wnt hyperplastic glands. Data represent mean±SEM. (FIG. 3F, FIG. 3G) Mammary tumor incidence (FIG. 3F) and tumor volumes (FIG. 3G) 2 months after orthotopic transplantation of 10000 cells of the indicated sorted luminal and basal populations from 7-month tumor-free mammary glands into NSG mice. (FIG. 3H) H&E staining of spontaneous ErbB2-induced tumors and tumors generated by indicated transplanted cells. Scale bars: 200 µm (top) and 100 µm (bottom). (FIG. 3I) Schematic of mammary gland reconstitution assays used in (FIG. 3J-K). (FIG. 3J, FIG. 3K) Tables showing transplantation of limiting numbers of Lin− MECs (FIG. 3J) or Lin− CD24+CD29hi MECs (FIG. 3K) dissociated from mammary glands of WT or KO female virgin mice into cleared mammary fat pads of WT recipients. Three independent batches of experiments were combined and showed. (FIG. 3L) Quantification (% of fat pad area filled with outgrowth) of reconstituted mammary outgrowths in (FIG. 3K). None of the experimental groups was significant by Mann-Whitney test. Statistics: (FIG. 3D, FIG. 3E) Student's t-test. (FIG. 3G) Mann-Whitney test. (FIG. 3A, FIG. 3F) Fisher's exact test. (FIG. 3B) Chi-square test. (FIG. 3J, FIG. 3K) Limiting dilution analysis. *$p<0.001$, $p<0.01$, *$p<0.05$.

FIGS. 4A-O shows that MTDH is intrinsically required for oncogene-induced TICs functionality. (FIG. 4A) Schematic diagram of MMTV-Mtdh transgene construct and breeding scheme used to generate PyMT;Mtdh−/− mice with (Mtdh−/−+Tg) or without the MMTV-Mtdh transgene. (FIG. 4B) MTDH protein levels in PyMT-induced tumors from Mtdh+/+, Mtdh−/−, or Mtdh−/−+Tg mice. (FIG. 4C) Quantification of CD24+CD29low luminal population in Lin− MECs (n=4) from preneoplastic mammary glands of 6-week-old females of the indicated genotypes (left column: Mtdh−/− mice; right column: Mtdh−/−+Tg mice). (FIG. 4D) Kinetics of mammary tumor onset in MMTV-PyMT females of the indicated genotypes. Mtdh−/− (n=21), Mtdh−/−+Tg (n=20). FIG. 4 (E) Average number of tumor-free mammary glands at indicated ages (left column: Mtdh−/− mice; right column: Mtdh−/−+Tg mice) in the same cohort of mice as in (FIG. 4D). (FIG. 4F) Tumor burden of same cohorts of mice as in (FIG. 4D). (FIG. 4G, FIG. 4H) MTDH was knocked down by two independent shRNA (KD1 and KD2) in freshly dissociated PyMT;Mtdh+/+ pMECs and in vitro mammosphere (FIG. 4G, n=5, each in triplicates; left column: Control; middle column: KD1; right column: KD2) and in vivo tumor formation assays were performed (FIG. 4H, incidence at 3 months). FC, fold changes. (FIG. 4I, FIG. 4J) Mouse MTDH was expressed in freshly dissociated PyMT; Mtdh−/− pMECs via lentivirus transduction and in vitro mammosphere (FIG. 4I, n=4, each in triplicates; left column: vector; right column: MTDH) and in vivo tumor formation (FIG. 4J) assays were performed. (FIG. 4K) Schematic diagram of experiments in L-0. (FIG. 4L) Mammosphere formation of ALDH-positive or ALDH-negative tumor cells from PyMT;Mtdh+/+ tumors. (FIG. 4M) MTDH was knocked down in sorted ALDH+ cells from PyMT; Mtdh+/+ tumors and mammosphere assays were performed. (FIG. 4N) Mammosphere formation of Lin−CD24+CD61+ or Lin−CD24+CD61− tumor cells from Wnt;Mtdh+/+ tumors. (FIG. 4O) MTDH was knocked down in sorted Lin−CD24+CD61+ cells from Wnt;Mtdh+/+ tumors and mammosphere assays were performed. Statistics: (FIG. 4C, FIG. 4G, FIG. 4I, FIG. 4L-O) Student's t-test. (FIG. 4D) Log rank test. (FIG. 4E) Chi-square test. (FIG. 4F) Mann-Whitney test. (FIG. 4H, FIG. 4J) Limiting dilution analysis. *$p<0.001$, $p<0.01$, *$p<0.05$. Data represent mean±SEM.

FIGS. 5A-H shows that MTDH is intrinsically required for tumor-initiating activities of mammary epithelial cells. (FIG. 5A) Schematic diagram of MMTV-Mtdh transgene construct including the MMTV-LTR (mouse mammary tumor virus long terminal repeat) promoter, mouse Mtdh coding sequence and the SV40 polyadenylation sequences. HindIII and EcoRI restriction sites were used to clone Mtdh; SalI and SpeI restriction sites were used to linearize the fragment for microinjection into mouse zygotes. (FIG. 5B) Genomic DNA purified from transgenic mice tail snips were subjected to southern blot. Shown are one positive founder line 18 and two positive controls after digestions by two independent restriction enzymes. (FIG. 5C) Mtdh mRNA levels in organs from 8-week-old transgene-positive or negative female littermates (left column: 9077 MMTV-Mtdh–/–; middle column: 9078 MMTV-Mtdh–/–; right column 9079 MMTV-Mtdh–/–). All mice harbor wild-type endogenous Mtdh allele. (FIG. 5D) H&E staining of spontaneous PyMT-induced tumors from PyMT;Mtdh–/– mice with or without MMTV-Mtdh transgene. Scale bars: 200 μm (top) and 100 μm (bottom). (FIG. 5E) MTDH was knocked down by two shRNAs (KD1 and KD2) in ErbB2;Mtdh+/+ pMECs (n=5) and mammosphere formation assays were performed in triplicate for each independent sample (left column: Control; middle column: KD1; right column: KD2). Data represent mean±SEM, ***p<0.001 by Student's t-test. (FIG. 5F) Kinetics of mammary tumor onset (left) and growth (right) in FVB mice injected with PyMT;Mtdh–/– tumor cells transduced with either vector control or Mtdh-expressing lentiviruses (n=10). p values were based on log-rank test (left) and Student's t-test (right). (FIG. 5G, FIG. 5H) Mammary tumor incidence after orthotopic transplantation of pMECs (from two independent PyMT; Mtdh–/– mice) transduced with either vector control or Mtdh-expressing lentiviruses.

FIGS. 6A-F shows that SND1 is necessary for MTDH-mediated tumor initiation. (FIG. 6A) Combination of MTDH re-expression and SND1 knockdown in PyMT; Mtdh–/– tumor cells. The efficiency of SND1 KD and MTDH re-expression was assessed by western blotting. (FIG. 6B, FIG. 6C) In vitro mammosphere (FIG. 6B) and in vivo tumor formation (FIG. 6C, 6 weeks) assays were performed with cells generated in (FIG. 6A). +/– indicate whether the denoted protein is present (+) or absent (–) based on western blotting in (FIG. 6A). (FIG. 6D) SND1 was knocked down in PyMT;Mtdh+/+ or Wnt;Mtdh+/+ pMECs cells and mammosphere assays were performed in triplicates. (FIG. 6E, FIG. 6F) Tumor incidence (FIG. 6E) and volume (FIG. 6F) after orthotopic transplantations of control or SND1-KD PyMT;Mtdh+/+ pMECs. Statistics: (FIG. 6B, FIG. 6D) Student's t-test. (FIG. 6C, FIG. 6E) Limiting dilution analysis. (FIG. 6F) Mann-Whitney test. *p<0.001, p<0.01, *p<0.05. Data represent mean±SEM.

(FIG. 7A) Schematics of MTDH fragments and mutants with indicated SND1-binding capability. + indicates binding and – indicates no binding based on results shown below. Two putative nuclear localization signals are residues 432-451 for NLS2 and residues 561-580 for NLS3. In the enlarged view of the minimal binding region 386-407, 9 residues were targeted for mutagenesis in the current study. W394D and W401D either completely or strongly reduced the binding, respectively. (FIG. 7B) Pulldown of His6-SND1ΔC by GST-tagged MTDH fragments with indicated boundaries. The bound proteins were examined by SDS-PAGE and visualized by Coomassie blue staining. (FIG. 7C) Pulldown of His6-SND1ΔC by GST-tagged WT or triple mutant MTDH fragments (364-582). For (FIG. 7B) and (FIG. 7C), 1/10 of the His6-SND1ΔC input was shown, and GST alone was used as a negative control. Representative results of 3 independent experiments are shown. (FIG. 7D, FIG. 7E) Lysates from HEK293T cells expressing the indicated ectopic human SND1, AGO2 or MTDH were immunoprecipitated with anti-Myc and immunoblotted with the indicated antibodies.

FIGS. 8A-H shows that SND1-binding deficient MTDH fails to promote tumor-initiating potential of MECs. (FIG. 8A, FIG. 8E) Lysates from PyMT;Mtdh–/– MECs reconstituted with vector control, WT or mutant murine MTDH were immunoprecipitated with anti-MTDH antibody and immunoblotted for indicated proteins. (FIG. 8B, FIG. 8F) Mammosphere assays were performed with PyMT;Mtdh–/– pMECs reconstituted with indicated Mtdh constructs. (FIG. 8C, FIG. 8D, FIG. 8G, FIG. 8H) In vivo tumor formation (FIG. 8C, FIG. 8G for tumor incidence; FIG. 8D, FIG. 8H for tumor volumes) were performed at limiting numbers using PyMT;Mtdh–/– pMECs reconstituted with indicated WT or mutant MTDH. *Note: mouse W391D MTDH corresponds to human W394D MTDH; and mouse W398D MTDH corresponds to human W401D MTDH. Statistics: (FIG. 8B, FIG. 3F) Student's t-test. (FIG. 8C, FIG. 8G) Limiting dilution analysis. (FIG. 8D, FIG. 8H) Mann-Whitney test. Data represent mean±SEM. *p<0.001, p<0.01, *p<0.05.

FIGS. 9A-I illustrates that MTDH confers survival advantage by interacting with and stabilizing pro-survival protein SND1 under stress. (FIG. 9A) Quantification of cleaved caspase 3-positive MECs from normal or MMTV-PyMT preneoplastic glands (n>3) of WT (left column) or KO females (right column). (FIG. 9B) The effect of CPT on the apoptosis of PyMT;Mtdh–/– pMECs reconstituted with indicated Mtdh constructs (left column: VEC; middle column: WT; right column: W391D) was determined by PI and Hoechst staining. (FIG. 9C) The effect of CPT on the apoptosis of control (left column) or SND1-KD (right column) PyMT;Mtdh+/+ pMECs. (FIG. 9D) Protein levels of SND1 and β-actin (loading control) in control or MTDH-KD PyMT;Mtdh+/+ pMECs treated with CPT at indicated concentrations for 36 hours. Degradation curve (right) represents the average of 3 independent experiments. (FIG. 9E) Western blotting of SND1, MTDH and β-actin (loading control) in PyMT;Mtdh–/– MECs reconstituted with indicated constructs after CPT treatment for 48 hours. Degradation curves (right) represent average of 3 independent experiments. (FIG. 9F) Heat map representation of microarray data displaying the expression of SND1-upregualted genes (n=504, fold change>2, p<0.05) in control versus SND1-KD PyMT;Mtdh+/+ pMECs under CPT (50 μM) treatment for 36 h. Color key indicates log 2 values. (FIG. 9G) Ingenuity Pathway Analysis shows the top 5 molecular and cellular functions of SND1-upregulated genes shown in (FIG. 9F) and the number of molecules/genes implicated in each category. (FIG. 9H) Effects of SND1-upregulated genes in cell survival and cell death functions. Z scores were calculated based on gene expression changes and gene functions as specified by the ingenuity knowledge base. A given function is predicted to be significantly increased when z>2 or decreased when z<–2. (FIG. 9I) GSEA plot showing the enrichment of SND1-upregulated gene signature in PyMT;Mtdh–/– MECs rescued with mouse WT MTDH as compared to those rescued with W391D mutant MTDH. All cells were treated with CPT (50 μM). NES:

normalized enrichment score. Statistics: (FIG. 9A-C) Student's t-test. Data represent mean±SEM. *p<0.001, p<0.01, *p<0.05.

FIGS. 10A-K shows MTDH and SND1 are important for in vitro sphere-forming and in vivo tumor-initiating activities of human breast cancer cells. (FIG. 10A, FIG. 10B) MTDH (FIG. 10A) or SND1 (FIG. 10B) was knocked down in HMLE-Neu cells and tumorsphere assays were performed in triplicates. (FIG. 10C, FIG. 10D) MTDH (FIG. 10C) or SND1 (FIG. 10D) was knocked down in the BCM-4013 patient-derived xenografted (PDX) tumor cells and tumorsphere assays were performed in triplicates. (FIG. 10E) MTDH or SND1 was knocked down in MDA-MB-231 cells, and the KD efficiency was measured by immunoblotting. (FIG. 10F) Tumorsphere assays of MDA-MB-231 cells were performed in triplicates. (FIG. 10G, FIG. 10H) Tumor incidence (FIG. 10G) and volumes (FIG. 10H) 5 weeks after injection of limiting numbers of MDA-MB-231 cells. (FIG. 10I) The protein levels of MTDH and SND1 in human invasive mammary carcinomas (n=154) were determined by IHC staining of a breast cancer tissue microarray (BR1921a, US Biomax). The staining intensity in tumor cells was scored as 0 (negative), 1 (weak), 2 (moderate), 3 (strong). (FIG. 10J) Bar graph presentation of (FIG. 10I). (FIG. 10K) Schematic illustration depicting the essential role of MTDH in tumor initiation but not normal gland development. Under stress conditions during tumorigenesis, the MTDH-SND1 interaction protects SND1 from stress-induced degradation and supports the survival and activities of both basal and luminal TICs. Statistics: (FIG. 10A-D, FIG. 10F) Student's t test. (FIG. 10G) Limiting dilution analysis. (FIG. 10H) Mann-Whitney test. (FIG. 10I, FIG. 10J) Chi-square test. Data represent mean±SEM. *p<0.001, p<0.01, *p<0.05.

FIGS. 11A-M shows MTDH and SND1 positively correlate at protein levels in human breast cancers and cooperate in predicting poor prognosis. (FIG. 11A, FIG. 11B) MTDH (FIG. 11A) or SND1 (FIG. 11B) was knocked down in HMLE-Neu cells by 3 independent shRNAs, and the KD efficiency was measured by immunoblotting. (FIG. 11C, FIG. 11D) MTDH (FIG. 11C) or SND1 (FIG. 11D) was knocked down in BCM-4013 patient-derived xenografted (PDX) tumor cells (Zhang et al., 2013) by 2 independent shRNAs and the KD efficiency was measured by q-PCR. Data represent mean±SEM. (FIG. 11E, FIG. 11F) Validation of the specificity of MTDH (FIG. 11E) and SND1 (FIG. 11F) antibodies for immunohistochemical staining. The antibodies are reactive to both human and mouse proteins. (FIG. 11E), Representative immunohistochemical staining of MTDH in PyMT;Mtdh+/+ and PyMT;Mtdh−/− mammary tumors. (FIG. 11F), Representative immunohistochemical staining of SND1 in PyMT;Mtdh+/+ control or SND1-KD tumors. Scale bars: 100 µm. (FIG. 11G) The protein levels of MTDH and SND1 in human breast tumors were determined by immunohistochemistry staining of a breast cancer tissue microarray (YTMA_201, Cancer Institute of New Jersey). The staining intensity in tumor cells was scored as 0 (negative), 1 (weak), 2 (moderate), 3 (strong). (FIG. 11H) Bar graph presentation of (FIG. 11G). (FIG. 11I) Correlation between mRNA levels of MTDH and SND1 in the NKI295 dataset. (FIG. 11J, FIG. 11K) Correlation between MTDH and SND1 mRNA levels with primary tumor size (FIG. 11J) and differentiation (FIG. 11K) of breast tumors. (FIG. 11L) Distant metastasis free survival (DMFS) of breast cancer patients stratified by the mRNA levels of MTDH and SND1. In FIG. 11J-L, NKI295 human breast cancer dataset (van de Vijver et al., 2002) was used and samples were divided into four groups based on MTDH/SND1 mRNA levels using medium cutoff. (FIG. 11M) Correlation between MTDH mRNA levels with prognosis of different subtypes of human breast cancer. Kaplan-Meier plot of relapse-free survival of patients stratified by median MTDH expression in the KM Plotter breast cancer meta-analysis database (Gyorffy et al., 2010). Statistics: (FIG. 11C, FIG. 11D) Student's t-test. (FIG. 11G, FIG. 11H, FIG. 11J, FIG. 11K) Chi-square test. (FIG. 11I) Pearson correlation. (FIG. 11L, FIG. 11M) Log rank test. *p<0.001, p<0.01, *p<0.05.

(FIG. 12A) Two prostate tumor tissue microarrays were stained with an anti-MTDH antibody. MTDH levels were scored as negative (0), low (1), medium (2) or high (3). Representative images of MTDH immunostaining of prostate tissue of different stages and distant metastasis. Scale bar, 40 µm. (FIG. 12C), Left panel, MTDH expression levels in normal tissues (n=62) and BPN (n=10), PIN (n=10), primary tumors (n=72) and distant metastasis (n=10) (left column: MTDH IHC score of 0 or 1; right column: MTDH IHC score of 2 or 3). P<0.001 by Chi-square test. Right panel, MTDH levels in PIN (n=10) and BPH (n=10) (left column: MTDH IHC score of 0; middle column: MTDH IHC score of 1 and right column: MTDH IHC score of 2). P=0.023 by Chi-square test. (FIG. 12B), Correlation of MTDH levels with prostate tumor Gleason scores. Top curve represents average MTDH score (mean±SEM) and bottom curve represents the percentage of samples with medium/ high levels of MTDH within indicated groups. (FIG. 12D), Kaplan-Meier analysis of recurrence-free survival of prostate cancer patients based on MTDH expression in their tumors.

FIGS. 13-A-D shows MTDH genomic gain is associated with MTDH protein levels and clinical progression in prostate cancer.

(FIG. 14A), Cross scheme for the generation of TRAMP mice in C57BL/6 background with different Mtdh status. (FIG. 14B), Genotyping of mice generated in (FIG. 14A). Top, the detected WT (602 bp) and gene-trapped mutant alleles (472 bp) of Mtdh. Bottom, the detected TRAMP transgene (600 bp) and internal genomic control (324 bp). (FIG. 14C), Mtdh mRNA in prostate tissues from mice with indicated genotypes analyzed by qPCR. Mtdh mRNA was undetectable in Mtdh$^{-/-}$ tissues, and elevated in TRAMP-positive prostate tissues as compared to normal glands.  P<0.01, * P<0.001 based on Mann-Whitney test. (FIG. 14D), Western blot analysis of Mtdh in prostates from WT non-transgenic mice and tumors from TRAMP/Mtdh$^{+/+}$ mice. Arbitrary levels of Mtdh protein after normalized to β-actin are shown at the bottom. E-F, Representative immunohistochemical staining of SV40 Tag oncoprotein in prostate glands from 8- (FIG. 14E) and 28-week-old (FIG. 14F) TRAMP/Mtdh$^{+/+}$ and TRAMP/Mtdh$^{-/-}$ mice. Scale bar, 50 μm.

(FIG. 15A-B), Wet weight (FIG. 15A) or relative weight as % of body weight (FIG. 15B) of lower urogenital tracts excised from TRAMP/Mtdh$^{+/+}$ and TRAMP/Mtdh$^{+/-}$ mice (denoted as Mtdh$^{+}$) or TRAMP/Mtdh$^{-/-}$ (denoted as Mtdh$^{-}$). Data represent mean±SEM.  P<0.01 based on Mann-Whitney test. (FIG. 15C), Representative images of lower urogenital tracts (B, bladder; P, prostate; SV, seminal vesicle) excised from 36-week-old male mice with indicated genotypes. Scale bar, 1 cm. (FIG. 15**D), Tumor incidence scored by examining histological sections of prostate glands from cohorts of TRAMP mice with indicated Mtdh genotype at different ages. The numbers on top of each bar graph indicates the number of mice with prostate cancer versus total number of mice examined in a given group. *P<0.05 and  P<0.01 based on Chi-square test. (FIG. 15E), Mortality rate of TRAMP mice with indicated Mtdh genotypes by one year of age. * P<0.001 based on Chi-square test.

(FIG. 16A), H&E-stained histologic sections of prostates dissected from TRAMP/Mtdh$^{+}$ and TRAMP/Mtdh$^{-}$ mice at indicated ages. Scale bar: 200 μm. (FIG. 16B), Each prostate from mice with indicated genotypes and ages was assigned a single highest grade. '+' and '−' indicate TRAMP/Mtdh$^{+}$ and TRAMP/Mtdh$^{-}$ mice, respectively. Grade scores: 1, normal; 2, low grade PIN; 3, high-grade PIN; 4, well differentiated adenocarcinoma and phyllode tumor; 5, moderately differentiated adenocarcinoma; 6, poorly differentiated adenocarcinoma and neuroendocrine tumors. The grading scheme followed standard protocol as previously described (Hurwitz et al., Current protocols in immunology/edited by John E Coligan [et al]. 2001; Chapter 20:Unit 20 5). The numbers at the bottom of each column indicate total number of prostate glands evaluated in each group. P<0.05 by Chi-square test in T36 group. (FIG. 16C), Quantification of Ki67-positive epithelial cells. Data represent mean±SEM. **P<0.01 based on Student's t-test.

(FIG. 17A), Incidence of lung, liver and lymph node metastasis in cohorts of one-year-old TRAMP mice with indicated Mtdh genotypes. P values based on Chi-square test. (FIG. 17B), Bar graph presentation (left column: Mtdh+; right column: Mtdh−) of (FIG. 17A).

(FIG. 18A-B), Mtdh was knocked down by two independent shRNA, as quantified by qPCR (FIG. 18A) and western blot (FIG. 18B). (FIG. 18C), Proliferation rate of control and Mtdh-KD TRAMP-C1 cancer cells after 48 hours. (FIG. 18D), Kinetics of prostate tumor onset in male mice subcutaneously transplanted with control (n=16), Mtdh-KD1 (n=8) and Mtdh-KD2 (n=12) TRAMP-C1 cells. P value based on log-rank test. (FIG. 18E), Tumor volumes 5 weeks post injection in (FIG. 18D). *P<0.001 based on Mann-Whitney test. (FIG. 18F), Images of tumors dissected 5 weeks post transplantation in (FIG. 18D). G, Mtdh mRNA levels in tumors formed in control and KD groups. Note the tumors that eventually grew in the KD groups expressed similar levels of Mtdh as the controls. (FIG. 18A, FIG. 18C, FIG. 18G) Data represent mean±SEM and P values based on Student's t-test.  P<0.01, *** P<0.001, n.s. not significant.

(FIG. 20A) Overlay of the structures of SN1/2 (magenta, in the complex with MTDH), SN3/4 (blue, PDB code: 3BDL) and two models of SNase (yellow, PDB code: 2ENB) in stereo view. The difference in Lβ2-β3 loop is emphasized by a dashed circle. (FIG. 20B) Sequence alignment of SN1/2 with SN3/4 from SND1 and SNase. Secondary structural elements are indicated above the sequences. Conserved residues are colored red. Residues that interact with MTDH are identified by green squares. The residues at the active site of SNase that contribute to the nuclease activity are indicated by red circles.

(FIG. 22A) In vitro pull-down of SND1 (16-339) by GST-tagged MTDH (364-582) harboring WT or mutant sequence. The proteins bound to GS4B were examined on SDS-PAGE and visualized by Coomassie blue staining. (FIG. 22B) In vitro pull-down of WT and mutant SND1 (16-339) by GST-tagged MTDH (364-582). The bound proteins were examined as in (FIG. 22A). For both (FIG. 22A) and (FIG. 22B), experiments were repeated three times; representative results are shown. The normalized percentage of binding was averaged from three experiments; mean±SEM was shown below the data. (FIG. 22C) HEK293T cells were transfected with human HA-SND1, WT Myc-MTDH or Myc-MTDH with indicated single point mutation. Lysates were immunoprecipitated with anti-Myc antibody and immunoblotted with the indicated antibodies. (FIG. 22D) HEK293T cells were transfected with human Myc-MTDH, WT HA-SND1 or mutant HA-SND1 with indicated single point mutations or deletions. Lysates were immunoprecipitated with anti-Myc and immunoblotted with the indicated antibodies.

FIGS. 23A-E shows that mutations in SND1-binding residues impair tumor-promoting function of MTDH. (FIG. 23A) Lysates from PyMT;Mtdh−/− tumor cells reconstituted with vector control, WT or mutant murine MTDH were immunoprecipitated with anti-MTDH antibody and immunoblotted for indicated proteins. Note all amino acid annotations are based on human MTDH. W394 and W401 of human MTDH correspond to W391 and W398 in murine MTDH, respectively. (FIG. 23B) Mammosphere assays were performed with PyMT;Mtdh−/− tumor cells reconstituted with indicated MTDH constructs. (FIG. 23C-E) In vivo tumor formation (FIG. 23C for tumor incidence; FIG. 23D, FIG. 23E for tumor volumes) were performed at limiting numbers using PyMT;Mtdh−/− tumor cells reconstituted with indicated WT or mutant MTDH. Statistics: (FIG. 23B) Student's t-test. Data represent mean±SEM. (FIG. 23C) Limiting dilution analysis. (FIG. 23D, FIG. 23E) Mann-Whitney test. **p<0.01, *p<0.05.

(FIG. 24A) Lysates from SND1-KD PyMT;Mtdh+/+ tumor cells reconstituted with vector control, WT or mutant shRNA-resistant murine SND1 were immunoprecipitated with anti-MTDH antibody and immunoblotted for indicated proteins. (FIG. 24B) Mammosphere assays were performed with SND1-KD PyMT;Mtdh+/+ tumor cells reconstituted with vector control or indicated SND1 constructs. (FIG. 24C, FIG. 24D) Mammary tumor incidence (FIG. 24C) and tumor growth curve (FIG. 24D) after orthotopic transplantations of SND1-KD PyMT;Mtdh+/+ tumor cells reconstituted with indicated constructs. Statistics: (FIG. 24B, FIG. 24D) Student's t-test. Data represent mean±SEM. (FIG. 24C) Chi-square test. ***p<0.01, *p<0.01, *p<0.05.

(FIG. 26A, FIG. 26B) Cell lysate was incubated with anti-HA antibody or IgG overnight followed by 2 hr incubation with Protein A/G beads to pull down HA-SND1 protein. The beads was washed with lysis buffer and split into 5 fractions. Each fraction was eluted with buffer or indicated peptides for 30 min. The elution fractions and beads were collected for WB. (FIG. 26C, FIG. 26D) Cell lyaste was split into 6 fractions, one of them was incubated with IgG and the rest were incubated with anti-HA antibody plus either buffer or indicated peptides. After 24 hr, the lysate was incubated with Protein A/G beads then the beads were washed in wash buffer.

(FIG. 27A) Cell lysate was incubated with anti-SND1 antibody or IgG overnight followed by 2 hr incubation with Protein A/G beads to pull down endogenous SND1 protein. The beads were washed with lysis buffer and split into 5 fractions. Each fraction was eluted with buffer or indicated peptides for 30 min. The elution fractions and beads were collected for WB. (FIG. 27B) Cell lyaste was split into 5 fractions, and incubated with anti-SND1 antibody plus either buffer or indicated peptides. After 24 hr, the lysate was incubated with Protein A/G beads then the beads were washed in wash buffer.

DETAILED DESCRIPTION

Figures 3K, 3L:
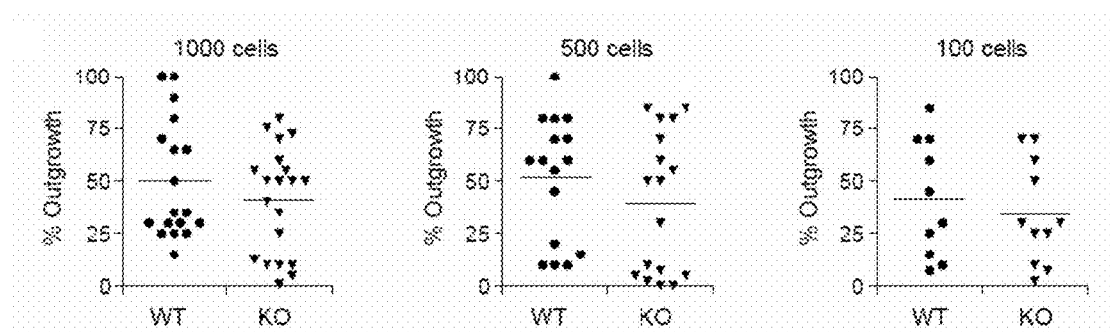

The present disclosure provides methods to reduce cancer growth and cancer metastasis by inhibiting the activity of the MTDH-SND1 complex using peptides or other compounds that inhibit the binding of SND1 with MTDH. The inventors discovered that MTDH deficiency inhibits diverse oncogene- or carcinogen-induced tumorigenesis. Results below show that MTDH is selectively required for TICs and MTDH-mediated stabilization of SND1 confers a survival advantage under stress. This is the first disclosure that MTDH interaction is required for SND1-dependent expression of pro-survival genes.

As used herein and in the appended claims, the singular forms "a," "and," and "the" include plural referents unless the context clearly dictates otherwise. Thus, for example, reference to "a derivative" includes a plurality of such derivatives and reference to "a patient" includes reference to one or more patients and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and products, the exemplary methods, devices and materials are described herein.

The documents discussed above and throughout the text are provided solely for their disclosure prior to the filing date of the present application. Nothing herein is to be construed as an admission that the inventors are not entitled to antedate such disclosure by virtue of prior disclosure. Each document is incorporated by reference in its entirety with particular attention to the disclosure for which it is cited.

The following references provide one of skill with a general definition of many of the terms used in this disclosure: Singleton, et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger, et al. (eds.), Springer Verlag (1991); and Hale and Marham, THE HARPER COLLINS DICTIONARY OF BIOLOGY (1991).

As used herein "an inhibitor of the interaction between metadherin (MTDH) and Staphylococcal nuclease domain-containing 1 (SND1)" or a "MTDH/SND1 inhibitor" refers to a compound or composition that inhibits the interaction of MTDH with SND1 at the binding sites of the two proteins. In one embodiment, the inhibitor inhibits binding between the proteins at residues 393-403 of MTDH (i.e., SEQ ID NO: 1). Additional inhibitors are described in greater detail in the Detailed Description.

As used herein, a "therapeutically effective amount" or "effective amount" refers to that amount of a peptide or other inhibitor product described herein, sufficient to result in amelioration of symptoms, for example, treatment, healing, prevention or amelioration of the relevant medical condition, or an increase in rate of treatment, healing, prevention or amelioration of such conditions, typically providing a statistically significant improvement in the treated patient population. When referencing an individual active ingredient, administered alone, a therapeutically effective dose refers to that ingredient alone. When referring to a combination, a therapeutically effective dose refers to combined amounts of the active ingredients that result in the therapeutic effect, whether administered in combination, including serially or simultaneously. In various embodiments, a therapeutically effective amount of the peptide or other inhibitor product ameliorates symptoms associated with various cancers, including but not limited to, loss of appetite, oral pain, upper abdominal pain, fatigue, abdominal swelling, persistent aches, bone pain, nausea, vomiting, constipation, weight loss, headaches, rectal bleeding, night sweats, digestive discomfort, and painful urination.

"Treatment" refers to prophylactic treatment or therapeutic treatment. In certain embodiments, "treatment" refers to administration of a compound or composition to a subject for therapeutic or prophylactic purposes.

A "therapeutic" treatment is a treatment administered to a subject who exhibits signs or symptoms of pathology for the purpose of diminishing or eliminating those signs or symptoms. The signs or symptoms may be biochemical, cellular, histological, functional or physical, subjective or objective.

A "prophylactic" treatment is a treatment administered to a subject who does not exhibit signs of a disease or exhibits only early signs of the disease, for the purpose of decreasing the risk of developing pathology. The compounds or compositions of the disclosure may be given as a prophylactic treatment to reduce the likelihood of developing a pathology or to minimize the severity of the pathology, if developed.

"Pharmaceutical composition" refers to a composition suitable for pharmaceutical use in a subject animal, including humans and mammals. A pharmaceutical composition comprises a therapeutically effective amount of a peptide or other product described herein, optionally another biologically active agent, and optionally a pharmaceutically acceptable excipient, carrier or diluent. In an embodiment, a pharmaceutical composition encompasses a composition comprising the active ingredient(s), and the inert ingredient(s) that make up the carrier, as well as any product that results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound of the disclosure and a pharmaceutically acceptable excipient, carrier or diluent.

"Pharmaceutically acceptable carrier" refers to any of the standard pharmaceutical carriers, buffers, and the like, such as a phosphate buffered saline solution, 5% aqueous solution of dextrose, and emulsions (e.g., an oil/water or water/oil emulsion). Non-limiting examples of excipients include adjuvants, binders, fillers, diluents, disintegrants, emulsifying agents, wetting agents, lubricants, glidants, sweetening agents, flavoring agents, and coloring agents. Suitable pharmaceutical carriers, excipients and diluents are described in Remington's Pharmaceutical Sciences, 19th Ed. (Mack Publishing Co., Easton, 1995). Preferred pharmaceutical carriers depend upon the intended mode of administration of the active agent. Typical modes of administration include enteral (e.g., oral) or parenteral (e.g., subcutaneous, intramuscular, intravenous or intraperitoneal injection; or topical, transdermal, or transmucosal administration).

As used herein "pharmaceutically acceptable" or "pharmacologically acceptable" salt, ester or other derivative of an active agent comprise, for example, salts, esters or other derivatives refers to a material that is not biologically or otherwise undesirable, i.e., the material may be administered to an individual without causing any undesirable biological effects or without interacting in a deleterious manner with any of the components of the composition in which it is contained or with any components present on or in the body of the individual.

As used herein, the term "unit dosage form" refers to physically discrete units suitable as unitary dosages for human and animal subjects, each unit containing a predetermined quantity of a compound of the disclosure calculated in an amount sufficient to produce the desired effect, optionally in association with a pharmaceutically acceptable excipient, diluent, carrier or vehicle. The specifications for the novel unit dosage forms of the present disclosure depend on the particular compound employed and the effect to be achieved, and the pharmacodynamics associated with each compound in the host.

As used herein, the term "subject" encompasses mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. The term does not denote a particular age or gender. In various embodiments the subject is human.

Metadherin and SND1

Metadherin: Metadherin (MTDH; also known as AEG-1, 3D3/LYRIC) was identified as a pro-metastasis gene that resides in 8q22, a frequently amplified genomic locus linked to poor relapse-free survival of breast cancer (Hu et al., 2009). The amino acid sequence of human metadherin can be found in Genbank Accession No. AAH45642, herein incorporated by reference, and is also provided herein as SEQ ID NO: 1. In recent years, elevated levels of MTDH have been reported in more than 20 cancer types (4), suggesting a potentially crucial and broad functionality of this gene in human cancer. Depending on the cancer type tested, recent studies using mainly cell culture systems have implicated MTDH in many cancer-related processes, including cellular proliferation, stress-induced cell death, invasion, chemoresistance and metastasis (Emdad et al., 2013; Wan and Kang, 2013).

These pleiotropic tumor-promoting roles of MTDH may stem from the complex nature of this protein, as revealed by its initial identification. MTDH was originally reported as an HIV-induced gene in astrocytes (Su et al., 2002), a cell-surface molecule mediating the homing of mammary tumor cells to the lung endothelium (Brown and Ruoslahti et al., 2004), a lysine-rich CEACAM1 co-isolated (LYRIC) protein associated with tight junctions in prostate epithelial cells (Britt et al., 2004), and as a novel transmembrane protein present in the different sub-cellular compartments (Sutherland et al., 2004). At the molecular level, the human MTDH encodes a 582-amino acid protein with no recognizable domains that could indicate its biological function, except for a putative transmembrane domain and three lysine-rich nuclear localization signals (Thirkettle et al., 2009). MTDH has recently been reported to interact with multiple proteins. In the nucleus, MTDH was shown to interact with PLZF (Thirkettle et al., 2009), BCCIPα (Ash et al., 2008) and NFκB subunit p65 (Emdad et al., 2006; Sarkar et al., 2008). In cytoplasm, MTDH was reported to interact with staphylococcal nuclease domain-containing protein 1 (SND1) (Blanco et al, 2011; Yoo et al., 2011; Meng et al., 2012). MTDH has also been linked to multiple classical oncogenic signaling pathways such as PI3K/AKT and Wnt signaling (Emdad et al., 2013) in a cancer cell-type dependent manner. However, whether MTDH exerts its function through interacting with its binding partners, and how MTDH modulates abovementioned oncogenic pathways remain largely unknown.

SND1: SND1 is a multifunctional protein harboring four tandem repeats of Staphylococcal nuclease (SN)-like domains at the N terminus (SN1-4), and a fusion tudor and SN domain (TSNS domain) at the C terminus (Callebaut and Mornon, 1997; Ponting, 1997). It belongs to the oligonucleotide/oligosaccharide binding-fold (OB-fold) superfamily consisting of proteins that primarily participate in DNA/RNA-binding via the typical β-barrel of the OB-fold (Theobald et al., 2003). The amino acid sequence of human SND1 can be found in Genbank Accession no. NP_055205, herein incorporated by reference, and is also provided herein as SEQ ID NO: 2. Consistently, SND1 was suggested to be an essential component of the RNA-induced silencing complex (RISC) and involved in miRNA-mediated silencing (Caudy et al., 2003). It was also shown to have a nuclease activity toward hyper-edited miRNA primary transcripts (Scadden, 2005). Structural and biochemical analysis of SND1 suggested that the N-terminal SN domains, particularly SN3/4, possess RNA-binding and nuclease activity (Li et al., 2008), and the C-terminal TSN domain interacts with methylated Lys/Arg ligands and small nuclear ribonucleoprotein (snRNP) complexes (Shaw et al., 2007). SND1 is among the very few members of the OB-fold superfamily that participate in interaction with diverse proteins. It was initially identified as a cellular component that enhances the transcription of EBNA-2-activated gene (Tong et al., 1995), and later shown to interact with and modulate a broad spectrum of proteins involved in transcription (Leverson, 1998; Paukku et al., 2003; Valineva et al., 2005; Valineva et al., 2006; Yang, 2002), including oncogenic transcription factors STAT5, STAT6, and c-Myb. In recent years, SND1 was identified as a binding partner of MTDH in multiple types of cancer, and has been shown to be important for cancer cell survival under oncogenic or chemotherapeutic stresses (Blanco et al., 2011; Meng et al., 2012; Wan et al., 2014; Yoo et al., 2011).

SND1 is an interacting partner of MTDH that possesses tumor-promoting function similar to that of MTDH (Blanco et al., 2011; Meng et al., 2012; Wang et al., 2012; Yoo et al., 2011). It is shown herein that the biochemically identified MTDH mutants with compromised SND1-binding exhibited a reduced activity in the expansion and survival of tumor-initiating cells in diverse subtypes of breast cancer (Wan et al., 2014). No structural insight has yet been available for understanding the interaction between MTDH and its binding partners and how these interactions affect its role in cancer. Whether the function of SND1 in cancer relies on MTDH-binding remains unclear. The range of identified SND1-interacting proteins suggests that its SN domains have been evolved into protein-protein interaction domains; the mode of interaction, however, has been unclear until the present disclosure.

Metadherin/SND1 Inhibitors

As described herein, the interaction of MTDH with SND1 plays an important role in the progression of tumor growth and metastasis. Administration of an inhibitor of this protein interaction is as a useful therapy for the treatment of cancer. As shown in Example 4, residues 394 and 401 of wild type MTDH set forth in SEQ ID NO: 1 are required for interaction with SND1. In some embodiments, the inhibitor is a peptide of MTDH comprising (a) the consensus sequence XWXXXXXXWXX (SEQ ID NO: 3), wherein X is any amino acid, or (b) XWXXXXXWXX (SEQ ID NO: 4), wherein X is any amino acid. In various embodiments, the inhibitor is a peptide of MTDH comprising the consensus sequence XWXXXXXXWXX (SEQ ID NO: 3) from residues 393-403 of MTDH, wherein X is any amino acid. In some embodiments, the inhibitor is a peptide of MTDH comprising the consensus sequence XWXXXXXWXX (SEQ ID NO: 4), wherein X is any amino acid.

In some embodiments, the MTDH/SND1 inhibitor is a peptide of MTDH, a peptide of SND1, a peptide mimetic having similar structure as a peptide comprising residues 393-403 of SEQ ID NO: 1, a peptide mimetic having a similar structure as a peptide comprising residues 390-403 of SEQ ID NO: 1, a small molecule compound that has similar structure or part of the structure as a peptide comprising residues 393-403 of SEQ ID NO: 1, a small molecule compound that has similar structure or part of the structure as a peptide comprising residues 390-403 of SEQ ID NO: 1, or a nanoparticle conjugate containing a peptide or peptide mimetic described herein.

In various embodiments, the inhibitor is a peptide of MTDH selected from i) a peptide within residues 364-582 of SEQ ID NO: 1, ii) a peptide within residues 364-407 of SEQ ID NO: 1, iii) a peptide comprising residues 386-407 of SEQ ID NO: 1, iv) a peptide comprising residues 393-403 of SEQ ID NO: 1, or v) a peptide comprising residues 390-403 of SEQ ID NO: 1; or vi) a peptide within residues 364-582, residues 364-407, residues 386-407, residues 393-403 or residues 390-403 of SEQ ID NO: 1 comprising the consensus sequence XWXXXXXXWXX (SEQ ID NO: 3) at residues 393-403, wherein X is any amino acid.

In some embodiments, the peptide comprises the sequence of DWNAPAEEWGN (SEQ ID NO: 5), or a variant thereof, wherein the variant peptide comprises at least one (such as any of 2, 3, 4, 5, 6, 7, 8, or 9) mutations at any position except for the W residues. In some embodiments, the peptide is about 11 to about 22 amino acids long (such as about 15 to about 22 amino acids long). In some embodiments, the peptide comprises about any of 1, 2, 3, 4, 5, 6, or 7 amino acids N-terminal to the sequence of DWNAPAEEWGN (SEQ ID NO: 5), or a variant thereof. In some embodiments, the peptide comprises about any of 1, 2, 3, or 4 amino acids C-terminal to the sequence of DWNAPAEEWGN (SEQ ID NO: 5), or a variant thereof.

In some embodiments, the peptide comprises the sequence of DWNAPEEWGN (SEQ ID NO: 20), or a variant thereof, wherein the variant peptide comprises at least one (such as any of 2, 3, 4, 5, 6, 7, 8, or 9) mutations at any position except for the W residues. In some embodiments, the peptide is about 10 to about 21 amino acids long (such as about 14 to about 21 amino acids long). In some embodiments, the peptide comprises about any of 1, 2, 3, 4, 5, 6, or 7 amino acids N-terminal to the sequence of DWNAPEEWGN (SEQ ID NO: 20), or a variant thereof. In some embodiments, the peptide comprises about any of 1, 2, 3, or 4 amino acids C-terminal to the sequence of DWNAPEEWGN (SEQ ID NO: 20), or a variant thereof.

In some embodiments, the peptide competes with a wild type MTDH peptide comprising the sequence of DWNAPAEEWGN (SEQ ID NO: 5) for binding to SND1 (e.g., a wildtype MTDH peptide having the same length). In some embodiments, the peptide binds to SND1 with an affinity that is at least about any of 50%, 60%, 70%, 80%, 90%, 95%, or 100% of the binding affinity of a wild type MTDH peptide comprising the sequence of DWNAPAEEWGN (SEQ ID NO: 5) for SND1 (e.g., a wildtype MTDH peptide having the same length).

In some embodiments, the peptide comprises a mutation at one or more amino acid residues in MTDH selected from the group consisting of D389, A392, D393, N395, E399, E400, W404, D406 and E407, wherein the position corresponds to the wild type MTDH (i.e., SEQ ID NO: 1). In one embodiment, the peptide comprises a mutation at one or more (such as 2, 3, 4, 5, 6, or 7) amino acid residues selected from the group consisting of N395, A396, P397, A398, E399, E400, and N403, wherein the position corresponds to the wild type MTDH (i.e., SEQ ID NO: 1). In some embodiments, the mutation in MTDH is selected from the group consisting of N395K, A396D, PAE(397-399)SQ, and E400D/N403L, wherein the position corresponds to the wild type MTDH (i.e., SEQ ID NO: 1). In various embodiments, the mutation in MTDH (SEQ ID NO: 1) is selected from the group consisting of D389R, D393R, E399R, E400R, W404D, D406R and E407R.

In various embodiments, the inhibitor is a peptide of SND1 within residues 16 to 339 of SND1 (i.e., SEQ ID NO: 2). In one embodiment, the SND1 peptide comprises a mutation at one or more residues selected from the group consisting of F250, R324, R255, R327, R324, P39, P43, E247, L256, H279, I284, L287, R259 and N281, wherein the position corresponds to wild type SND1 (i.e., SEQ ID NO: 2). In various embodiments, the mutation in SND1 (i.e., SEQ ID NO: 2 is selected from the group consisting of F250A R324E and R255E.

In some embodiments, the MTDH or SND1 peptide comprises (e.g., has) an amino acid sequence having 60 amino acids or less, 55 amino acids or less, 40 amino acids or less, 35 amino acids or less, or 30 amino acids or less. Optionally, the peptide comprises (e.g., has) an amino acid sequence having 25 amino acids or less, 20 amino acids or less, 15 amino acids or less, or 10 amino acids or less. In various embodiments, the peptide comprises (e.g., has) 10-35 amino acid residues (e.g., 10, 11, 12, 13, 14, 15, 16, 17, 18, 19, 20, 21, 22, 23, 24, 25, 26, 27, 28, 29, 30, 31, 32, 33, 34, or 35 amino acid residues). In some aspects, amino acids are removed from the peptide described herein from within the amino acid sequence, at the N-terminus, and/or at the C-terminus. Such peptide fragments can comprise 3-14 amino acid residues (e.g., 3, 4, 5, 6, 7, 8, 9, 10, 11, 12, 13, or 14 amino acid residues).

A peptide described herein can be fused or complexed to a second peptide domain that, for example, binds another target or increases the half-life or stability of the peptide.

In one aspect, the peptide further comprises one or more amino acids that facilitate synthesis, handling, or use of the peptide, including, but not limited to, one or two lysines at the N-terminus and/or C-terminus to increase solubility of the peptide. Suitable fusion proteins include, but are not limited to, proteins comprising a peptide described herein linked to one or more polypeptides, polypeptide fragments, or amino acids not generally recognized to be part of the protein sequence. In one aspect, a fusion peptide comprises the entire amino acid sequences of two or more peptides or, alternatively, comprises portions (fragments) of two or more peptides. In some aspects, a peptide described herein is operably linked to, for instance, one or more of the following: a marker protein, a peptide that facilitates purification, a peptide sequence that promotes formation of multimeric proteins, or a fragment of any of the foregoing. Suitable fusion partners include, but are not limited to, a His tag, a FLAG tag, a strep tag, and a myc tag.

Optionally, a peptide described herein is fused to one or more entities that enhance the half life of the peptide. Half life can be increased by, e.g., increasing the molecular weight of the peptide to avoid renal clearance and/or incorporating a ligand for the nFc receptor-mediated recycling pathway. In one embodiment, the peptide is fused to or chemically conjugated to an albumin polypeptide or a fragment thereof (e.g., human serum albumin (HSA) or bovine serum albumin (BSA)). The albumin fragment comprises 10%, 25%, 50%, or 75% of the full length albumin protein. Alternatively or in addition, the peptide is fused to or complexed with an albumin binding domain or fatty acid that binds albumin when administered in vivo. An example of an albumin binding domain is "albu-tag," a moiety derived from on 4-(p-iodophenyl)-butanoic acid (Dumelin et al., *Angew Chem Int Ed Engl* 47:3196-3201 (2008)). Other suitable fusion partners include, but are not limited to, a proline-alanine-serine multimer (PASylation) and an antibody or fragment thereof (e.g., an Fc portion of an antibody).

Derivatives are contemplated and include peptides that have been chemically modified in some manner distinct from addition, deletion, or substitution of amino acids. In this regard, a peptide provided herein is chemically bonded with polymers, lipids, other organic moieties, and/or inorganic moieties. Examples of peptide and protein modifications are given in Hermanson, *Bioconjugate Techniques*, Academic Press, (1996). The peptides described herein optionally comprise a functional group that facilitates conjugation to another moiety (e.g., a peptide moiety). Exemplary functional groups include, but are not limited to, isothiocyanate, isocyanate, acyl azide, NHS ester, sulfonyl chloride, aldehyde, epoxide, oxirane, carbonate, arylating agent, imidoester, carbodiimide, anhydride, alkyl halide derivatives (e.g., haloacetyl derivatives), maleimide, aziridine, acryloyl derivatives, arylating agents, thiol-disulfide exchange reagents (e.g., pyridyl disulfides or TNB thiol), diazoalkane, carboyldiimadazole, N,N'-Disuccinyl carbonate, N-Hydroxysuccinimidyl chloroformate, and hydrazine derivatives. Maleimide is useful, for example, for generating a Protein S-binding peptide that binds with albumin in vivo.

In one aspect, the invention includes peptides described herein covalently modified to include one or more water soluble polymer attachments. A water soluble polymer (or other chemical moiety) is attached to any amino acid residue, although attachment to the N- or C-terminus is preferred in some embodiments. Useful polymers include, but are not limited to, PEG (e.g., PEG approximately 40 kD, 30 kD, 20 kD, 10 kD, 5 kD, or 1 kD in size), polyoxyethylene glycol, polypropylene glycol, monomethoxy-polyethylene glycol, dextran, hydroxyethyl starch, cellulose, poly-(N-vinyl pyrrolidone)-polyethylene glycol, propylene glycol homopolymers, a polypropylene oxide/ethylene oxide co-polymer, polysialic acid (PSA), polyoxyethylated polyols (e.g., glycerol) and polyvinyl alcohol, as well as mixtures of any of the foregoing. In one aspect, the peptide of the invention is a PEGylated peptide. PEG moieties are available in different shapes, e.g., linear or branched. For further discussion of water soluble polymer attachments, see U.S. Pat. Nos. 4,640,835; 4,496,689; 4,301,144; 4,670,417; 4,791,192; and 4,179,337. Other moieties useful for improving peptide half life or stability are described herein and include, for instance, albumin (optionally modified to allow conjugation to the inventive peptide), fatty acid chains (e.g., C12-C18 fatty acid, such as a C14 fatty acid, or dicarboxylic acids, such as octadecane dicarboxylic acid (oddc)), an antibody or fragment thereof (e.g., an Fc portion of an antibody), and proline-alanine-serine multimers.

In another aspect, a peptide derivative includes a targeting moiety specific for a particular cell type, tissue, and/or organ. Alternatively, the peptide is linked to one or more chemical moieties that facilitate purification, detection, multimerization, binding with an interaction partner, and characterization of peptide activity. An exemplary chemical moiety is biotin. Other moieties suitable for conjugation to the peptide of the invention include, but are not limited to, a photosensitizer, a dye, a fluorescence dye, a radionuclide, a radionuclide-containing complex, an enzyme, a toxin, and a cytotoxic agent. Photosensitizers include, e.g., Photofrin, Visudyne, Levulan, Foscan, Metvix, Hexvix®, Cysview™, Laserphyrin, Antrin, Photochlor, Photosens, Photrex, Lumacan, Cevira, Visonac, BF-200 ALA, and Amphinex. If desired, a His tag, a FLAG tag, a strep tag, or a myc tag is conjugated to the peptide.

In addition, in one aspect, the peptides of the invention are acylated at the N-terminal amino acid of the peptide. In another aspect, the peptides of the invention are amidated at the C-terminal amino acid of the peptide. In a still further aspect, the peptides of the invention are acylated at the N-terminal amino acid of the peptide and are amidated at the C-terminal amino acid of the peptide.

Derivatives also include peptides comprising modified or non-proteinogenic amino acids or a modified linker group (see, e.g., Grant, *Synthetic Peptides: A User's Guide*, Oxford University Press (1992)). Modified amino acids include, for example, amino acids wherein the amino and/or carboxyl group is replaced by another group. Non-limiting examples include modified amino acids incorporating thioamides, ureas, thioureas, acylhydrazides, esters, olefines, sulfonamides, phosphoric acid amides, ketones, alcohols, boronic acid amides, benzodiazepines and other aromatic or non-aromatic heterocycles (see Estiarte et al., *Burgers Medicinal Chemistry*, 6$^{th}$ edition, Volume 1, Part 4, John Wiley & Sons, New York (2002)). Non-proteinogenic amino acids include, but are not limited, to β-alanine (Bal), norvaline (Nva), norleucine (Nle), 4-aminobutyric acid (γ-Abu), 2-aminoisobutyric acid (Aib), 6-aminohexanoic acid (ε-Ahx), ornithine (Orn), hydroxyproline (Hyp), taurine, sarcosine, citrulline (Cit), cysteic acid (Coh), cyclohexylalanine (Cha), methioninesulfoxide (Meo), methioninesulfone (Moo), homoserinemethylester (Hsm), propargylglycine (Eag), 5-fluorotryptophan (5Fw), 6-fluorotryptophan (6Fw), 3',4'-dimethoxyphenyl-alanine (Ear), 3',4'-difluorophenylalanine (Dff), 4'-fluorophenyl-alanine (Pff), 1-naphthyl-alanine (1Ni), 2-Naphthylalanine (2Ni), 1-methyltryptophan (1Mw), penicillamine (Pen), homoserine (Hse), t-butylglycine, t-butylalanine, phenylglycine (Phg), benzothienylalanine (Bta), L-homo-cysteine (Hcy), N-methyl-phenylalanine (Nmf), 2-thienylalanine (Thi), 3,3-diphenylalanine (Ebw), L-alpha-t-Butylglycine (Tle), Bpa, homophenylalanine (Hfe), and S-benzyl-L-cysteine (Ece). These and other non-proteinogenic amino acids may exist as D- or L-isomers. Examples of modified linkers include, but are not limited to, the flexible linker 4,7,10-trioxa-1,13-tridecanediamine (Ttds), glycine, 6-aminohexanoic acid, beta-alanine (Bal), pentynoic acid (Pyn), and combinations of Ttds, glycine, 6-aminohexanoic acid and Bal.

Homologs of the amino acids constituting the peptides of the invention may be as set forth in Table 1. In any embodiment, one or more amino acids of the peptide of the invention are substituted with an amino acid or building block set forth in Table 1.

TABLE 1

| Amino Acid | Exemplary homologs/substitutions |
|---|---|
| A | 2-Amino-isobutyric acid (Aib), β-Alanine (Bal), (S)-2-Propargylglycine (Eag), (S)-N-Methylalanine (Nma), 2-Aminobutyric acid (Abu), G, M, (S)-2-Aminopentanoic acid (Nva), (S)-Norleucine (Nle) |
| C | S, A, (S)-Homo-cysteine (Hcy), M, L, I, V, (R)-N-Methylcysteine (Nmc), β-Cysteine |
| D | E, Homoglutamic acid, γ-Hydroxy-glutamic acid, γ-Carboxy-glutamic acid, (S)-N-Methyl-Aspartic acid (Nmd), β-Aspartic acid, N, Q, Cysteic acid, β-Homoaspartic acid (Bhd) |
| E | D, Glu, Homoglutamic acid, γ-Hydroxy-glutamic acid, γ-Carboxy-glutamic acid, α-Aminoadipic acid, (S)-N-Methyl-glutamic acid (Nme), β-glutamic acid, Q, N, Cysteic acid, β-Homoglutamatic acid (Bhe) |
| F | L-Homophenylalanine (Hfe), (S)-N-Methyl-phenylalanine (Nmf), β-Phenylalanine, L-Phenylglycin (Phg), β-Homophenylalanine (Bhf), Thienylalanine, Benzothienylalanine, Bromophenylalanine, Iodophenylalanione, Chlorophenylalanine, Methylphenylalanine, Nitrophenylalanine, Y, W, Naphtylalanine, 1,2,3,4-L-tetrahydroisoquinolinecarboxylic acid (Tic) |
| G | A, a, N-Methyl-glycine (Nmg) |
| H | (S)-N-Methyl-histidine (Nmh), 1-Methylhistidine, 3-Methylhistidine, Thienylalanine |
| I | L, V, (S)-2-Amino-5-methyl-hexanoic acid (Hle), (S)-2-Amino-pentanoic acid (Nva), Nle, β-Isoleucine, (S)-N-Methyl-leucine (Nml), M, N-Methyl-L-isoleucine (Nmi), β-Homoisoleucine (Bhi), (S)-Cyclohexylalanine (Cha), L-Cyclohexylglycine (Chg) |
| K | (S)-N-Methyl-lysine (Nmk), R, (S)-N-Methyl-arginine (Nmr), β-Lysine, (S)-2,4-Diaminobutyric acid (Dab), (S)-Diaminopropionic acid (Dap), β-(1-Piperazinyl)-alanine, 2,6-Diamino-4-hexynoic acid, δ-Hydroxy-lysine, (S)-Homo-arginine (Har), ω-Hydroxy-norarginine, ω-Amino-arginine, ω-Methyl-arginine, β-(2-Pyridyl)-alanine, β-(3-Pyridyl)-alanine, 3-Amino-tyrosine, 4-Aminophenylalanine, (S)-Homo-citrulline (Hci), (S)-Citrullin (Cit), β-Homolysine (Bhk) |
| L | I, V, Hle, Nle, (S)-2-Amino-pentanoic acid (Nva), β-Isoleucine, (S)-N-Methyl-leucine (Nml), M, β-Homovaline(Bhv), β-Homoleucine (Bhl), (S)-Cyclohexylalanine (Cha) |
| M | I, V, Hle, Nva, R, (S)-Homo-arginine (Har), (S)-N-Methyl-methionine (Nmm), Methioninesulfone, Methionine-sulphoxid (Met(O)), Nle |
| N | (S)-N-Methyl-asparagine (Nmn), β-Asparagine, Q, (S)-N-Methyl-glutamine (Nmq), β-Glutamine, Cys(3-propionic acid amide)-OH, Cys(O2-3-propionic acid amide)-OH, β-Homoasparagine (Bhn), β-Homoglutamine (Bhq) |
| P | Azetidine-2-carboxylic acid, 4-Hydroxy-L-proline (Hyp), α-Methyl-methionine, 4-Hydroxy-piperidine-2-carboxylic acid, D-Pipecolic acid (Pip), α-Methyl-Pro, 3-Amino-Pro, 4-Amino-Pro |

TABLE 1-continued

| Amino Acid | Exemplary homologs/substitutions |
|---|---|
| Q | N, Nmn, (S)-N-Methyl-glutamine (Nmq), β-Glutamine, Cys(3-propionic acid amide)-OH, Cys(O2-3-propionic acid amide)-OH, Bhn, Bhq |
| R | (S)-N-Methyl-lysine (Nmk), K, (S)-N-Methyl-arginine (Nmr), β-Lysine, Dab, Dap, (S)-Ornithine (Orn), β-(1-Piperazinyl)-alanine, 2,6-Diamino-4-hexynoic acid, δ-Hydroxy-lysine, Har, ω-Hydroxy-norarginine, ω-Amino-arginine, ω-Methyl-arginine, β-(2-Pyridyl)-alanine, β-(3-Pyridyl)-alanine, 3-Amino-tyrosine, 4-Amino-phenylalanine, (S)-Homo-citrulline (Hci), (S)-Citrullin (Cit), Hle, L, (S)-Norleucine (Nle), M, Bhk, (S)-N-Methyl-lysine (Nmk) |
| S | T, homoserine (Hse), β-Serine, C, β-Cyano-alanine, allo-Threonine, β-Homoserine (Bhs) |
| T | S, Homothreonine, β-Threonine, allo-Threonine |
| V | L, I, Hle, (S)-2-Amino-pentanoic acid (Nva), Nle, β-Valine, (S)-N-Methyl-valine (Nmv), M, Nmi, (S)-N-Methyl-leucine (Nml), (S)-Cyclohexylalanine (Cha), L-Cyclohexylglycine (Chg) |
| W | (S)-N-Methyl-tryptophane (Nmw), β-Tryptophan, F, L-Homophenylalanine (Hfe), (S)-N-Methyl-phenylalanine (Nmf), β-Phenylalanine, L-Phenylglycin (Phg), β-Homophenylalanine (Bhf), Thienylalanine, Benzothienylalanine, Bromophenylalanine, Iodophenylalanine, Chlorophenylalanine, Methylphenylalanine, Nitrophenylalanine, Y, Naphtylalanine, 1,2,3,4-L-tetrahydroisoquinolinecarboxylic acid (Tic), β-Homotyrosine (Bhy) |
| Y | (S)-N-Methyl-tyrosine (Nmy), β-Tyrosine, F, Hfe, Nmf, β-Phenylalanine, Phg, Bhf, Thienylalanine, Benzothienylalanine, Bromophenylalanine, Iodophenylalanine, Chlorophenylalanine, Methylphenylalanine, Nitrophenylalanine, W, Naphtylalanine, Tic, Bhy |

In some embodiments, the peptide (CO—NH) linkages joining amino acids within the peptide of the invention are reversed to create a "retro-modified" peptide, i.e., a peptide comprising amino acid residues assembled in the opposite direction (NH—CO bonds) compared to the reference peptide. The retro-modified peptide comprises the same amino acid chirality as the reference peptide. An "inverso-modified" peptide is a peptide of the invention comprising amino acid residues assembled in the same direction as a reference peptide, but the chirality of the amino acids is inverted. Thus, where the reference peptide comprises L-amino acids, the "inverso-modified" peptide comprises D-amino acids, and vice versa. Inverso-modified peptides comprise CO—NH peptide bonds. A "retro-inverso modified" peptide refers to a peptide comprising amino acid residues assembled in the opposite direction and which have inverted chirality. A retro-inverso analogue has reversed termini and reversed direction of peptide bonds (i.e., NH—CO), while approximately maintaining the side chain topology found in the reference peptide. Retro-inverso peptidomimetics are made using standard methods, including the methods described in Meziere et al, *J. Immunol.*, 159, 3230-3237 (1997), incorporated herein by reference. Partial retro-inverso peptides are peptides in which only part of the amino acid sequence is reversed and replaced with enantiomeric amino acid residues.

In some embodiments, a peptide inhibitor described herein is conjugated to a carrier peptide or protein, such as a cargo protein or peptide, a transport peptide or peptide, or a cell penetrating protein or peptide (CPP) to improve pharmacokinetic behavior. Illustrative improved pharmacokinetic behavior includes, but is not limited to, longer serum and/or circulating half-lives, and/or greater cell permeation. In some embodiments, a peptide inhibitor described herein is conjugated with a transport peptide or cell penetrating peptide selected from the group consisting of the HIV TAT peptide, TATm, PTD, PTR (also referred to as PTD), pVEC, SynB, R9, R9-TAT, MTS, PreS2-TLM, HTLV-II REX, MAP, TP, PEP, and PrP.

In some embodiments, a peptide inhibitor described herein is admixed with a carrier peptide or protein, such as a cargo protein or peptide, a transport peptide or peptide, or a cell penetrating protein or peptide (CPP) to improve pharmacokinetic behavior.

Suitable molar ratio between the peptide inhibitor and the carrier peptide or protein can be, for example, about 1:100 to about 100:1, including for example about 1:50 to about 50:1, about 1:20 to about 20:1, about 1:10 to about 10:1, about 1:5 to about 5:1, or about 1:1. In some embodiments, the molar ratio between the peptide inhibitor and the carrier peptide or protein about any of about 1:1 to about 20:1, about 1:1 to about 10:1, about 1:1 to about 1:5:1, about 1:1 to about 2:1, about 1:1, about 1:1 to about 1:2, about 1:1 to about 1:5, about 1:1 to about 1:10, or about 1:1 to about 1:20.

Intracellular delivery of the peptides described herein for prophylaxis or treatment of a cancer as described herein can be achieved utilizing a "facilitator moiety" for facilitating passage or translocation of the peptide or nucleic acid across the outer cell/plasma membrane into the cytoplasm and/or nucleus of cells, such as a carrier peptide. A facilitator moiety as described herein may facilitate the entry of a peptide, agent or nucleic acid embodied by the invention into a cancer cell in any of a number of ways and the invention is not limited to any particular mechanism (e.g., direct penetration into the cell (e.g., via enhanced cell membrane solubility or formation of a transient pore in the cell membrane), endocytosis-mediated cell entry (e.g., via interaction with cell a surface expressed receptor, or macropinocytosis), and cell entry via formation of a transitory structure on the cell membrane. The facilitator moiety can be a lipid moiety or other non-peptide moiety (e.g., a carbohydrate moiety) which enhances cell membrane solubility of an anti-cancer peptide in accordance with the invention for passage across the outer cell membrane of the target cell or whereby entry of the peptide into the cell is facilitated. The lipid moiety can for instance be selected from triglycerides, including mixed triglycerides. Fatty acids and particularly, $C_{16}$-$C_{20}$ fatty acids can also be used. Typically, the fatty acid will be a saturated fatty acid and most usually, stearic acid.

In still another embodiment, a peptide described herein is conjugated with a conjugation agent for forming a complex with a label, signalling, or other molecule (e.g., a contrast agent, imaging agent, biotin, streptavidin, radioisotope, fluorescent dye, chemiluminescent agent, chemiluminophore, bioluminescent agent, enzyme or binding fragment thereof (e.g., Fab and F(ab)$_2$ fragments), magnetic particle(s), etc) for detection of the peptide. As will be understood, a peptide embodied by the invention can be coupled to a facilitator moiety for facility passage of the peptide into a target cell and a conjugation agent complexed with, or for being complexed to, a label, signaling molecule, radioisotope or the like for detection of the peptide within the cell utilising a suitable imaging technique (e.g., magnetic resonance imaging (MRI)). DOTA (1,4,7,10-tetraazacyclodecane-1,4,7,10-tetraacetic acid) is an example of a conjugation agent that may be used and can be complexed to a range of compounds for use in cancer therapy and diagnosis such as monoclonal antibodies, radioisotopes, and metal cations (e.g., calcium and gadolinium). In some embodiments, a peptide described herein is conjugated to DOTA complexed with gadolinium (Sturzu A et al, 2008) as a contrast agent for imaging of target cells.

In some embodiments, the peptides described herein are formulated into liposomes, microparticles, or nanoparticles, for example for targeted delivery and/or sustained release. Liposomes, microparticles, and nanoparticles suitable for peptide delivery (including targeted delivery and/or sustained release) are known in the art. See, e.g., Tan et al., Recent Developments in Liposomes, Microparticles, and Nanoparticles for protein and peptide drug delivery, Peptides, 31(1), 184-193, 2010.

Nanoparticle conjugates comprising one ore more of the peptides described herein are also contemplated. The term "nanoparticle" as used herein refers to means a particle whose size is measured in the nanometers range (i.e., less than 1 μm). In some embodiments, the nanoparticle has a total diameter in the range of approximately 2-500 nm, including for example about 2 to about 200 nm, about 10 to about 200 nm, about 50 to about 100 nm.

The nanoparticle core material can be a metal or semiconductor and may be formed of more than one type of atom. Preferably, the core material is a metal selected from Au, Fe or Cu. Nanoparticle cores may also be formed from alloys including Au/Fe, Au/Cu, Au/Gd, Au/Fe/Cu, Au/Fe/Gd and Au/Fe/Cu/Gd, and may be used in the present invention. Preferred core materials are Au and Fe, with the most preferred material being Au. The cores of the nanoparticles preferably comprise between about 100 and 500 atoms (e.g. gold atoms) to provide core diameters in the nanometer range. Other particularly useful core materials are doped with one or more atoms that are NMR active, allowing the nanoparticles to be detected using NMR, both in vitro and in vivo. Examples of NMR active atoms include $Mn^{+2}$, $Gd^{+3}$, $Eu^{+2}$, $Cu^{+2}$, $V^{+2}$, $Co^{+2}$, $Ni^{+2}$, $Fe^{+2}$, $Fe^{+3}$ and lanthanides$^{+3}$, or quantum dots.

Nanoparticle cores comprising semiconductor atoms can be detected as nanometre scale semiconductor crystals are capable of acting as quantum dots, that is they can absorb light thereby exciting electrons in the materials to higher energy levels, subsequently releasing photons of light at frequencies characteristic of the material. An example of a semiconductor core material is cadmium selenide, cadmium sulphide, cadmium tellurium. Also included are the zinc compounds such as zinc sulphide.

In some embodiments, the nanoparticle conjugate comprises a detectable label. The label may be an element of the core of the nanoparticle or the ligand. The label may be detectable because of an intrinsic property of that element of the nanoparticle or by being linked, conjugated or associated with a further moiety that is detectable. Preferred examples of labels include a label which is a fluorescent group, a radionuclide, a magnetic label or a dye. Fluorescent groups include fluorescein, rhodamine or tetramethyl rhodamine, Texas-Red, Cy3, Cy5, etc., and may be detected by excitation of the fluorescent label and detection of the emitted light using Raman scattering spectroscopy (Y. C. Cao, R. Jin, C. A. Mirkin, Science 2002, 297: 1536-1539).

In some embodiments, the nanoparticle conjugate comprise a radionuclide for use in detecting the nanoparticle using the radioactivity emitted by the radionuclide, e.g. by using PET, SPECT, or for therapy, i.e. for killing target cells. Examples of radionuclides commonly used in the art that could be readily adapted for use in the present invention include $^{99m}$Tc, which exists in a variety of oxidation states although the most stable is $TcO^{4-}$; $^{32}$P or $^{33}$P; $^{57}$Co; $^{59}$Fe; $^{67}$Cu which is often used as $Cu^{2+}$ salts; $^{67}$Ga which is commonly used a $Ga^{3+}$ salt, e.g. gallium citrate; $^{68}$Ge; $^{82}$Sr; $^{99}$Mo; $^{103}$Pd; $^{111}$In which is generally used as $In^{3+}$ salts; $^{125}$I or $^{131}$I which is generally used as sodium iodide; $^{137}$Cs; $^{158}$Au; $^{186}$Re; $^{201}$Tl generally used as a $Tl^+$ salt such as thallium chloride; $^{39}Y^{3+}$; $^{71}Lu^{3+}$; and $^{24}Cr^{2+}$. The general use of radionuclides as labels and tracers is well known in the art and could readily be adapted by the skilled person for use in the aspects of the present invention. The radionuclides may be employed most easily by doping the cores of the nanoparticles or including them as labels present as part of ligands immobilised on the nanoparticles.

Additionally or alternatively, the nanoparticles conjugates can be detected using a number of techniques well known in the art using a label associated with the nanoparticle as indicated above or by employing a property of them. These methods of detecting nanoparticles can range from detecting the aggregation that results when the nanoparticles bind to another species, e.g. by simple visual inspection or by using light scattering (transmittance of a solution containing the nanoparticles), to using sophisticated techniques such as transmission electron microscopy (TEM) or atomic force microscopy (AFM) to visualize the nanoparticles. A further method of detecting metal particles is to employ plasmon resonance that is the excitation of electrons at the surface of a metal, usually caused by optical radiation. The phenomenon of surface plasmon resonance (SPR) exists at the interface of a metal (such as Ag or Au) and a dielectric material such as air or water. As changes in SPR occur as analytes bind to the ligand immobilised on the surface of a nanoparticle changing the refractive index of the interface. A further advantage of SPR is that it can be used to monitor real time interactions. As mentioned above, if the nanoparticles include or are doped with atoms which are NMR active, then this technique can be used to detect the particles, both in vitro or in vivo, using techniques well known in the art. Nanoparticles can also be detected using a system based on quantitative signal amplification using the nanoparticle-promoted reduction of silver (I). Fluorescence spectroscopy can be used if the nanoparticles include ligands as fluorescent probes. Also, isotopic labelling of the carbohydrate can be used to facilitate their detection.

In some embodiments, a peptide described herein is conjugated to a gold nanoparticle for imaging or for assisted cell death of the target cells through laser irradiation of branched gold particles. Gold nanoparticle transfer across plasma and nuclear membranes has been reported previously (de la Fuente J. M. and Berry C. C., 2005).

The peptides described herein can be useful for many purposes. For example, in some embodiments, there is provided a method of disrupting the interaction between MTDH and SND1 in a subject, comprising administering to the subject any one of the peptide inhibitors (or pharmaceutical compositions comprising such peptide inhibitors) described herein. In some embodiments, there is provided a method of inhibiting SND1-dependent expression of pro-survival genes in a subject, comprising administering to the subject any one of the peptide inhibitors (or pharmaceutical compositions comprising such peptide inhibitors) described herein. In some embodiments, there is provided a method of treating cancer in a subject, comprising administering to the subject any one of the peptide inhibitors (or pharmaceutical compositions comprising such peptide inhibitors) described herein. In some embodiments, there is provided a method of inhibiting tumor metastasis in a subject having cancer, comprising administering to the subject any one of the peptide inhibitors (or pharmaceutical compositions comprising such peptide inhibitors) described herein.

Cancers

It is contemplated that the peptides of MTDH and/or SND1 and other inhibitors of MTDH and SND1 interaction described herein are useful to treat cancers in which MTDH plays a role. Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor. In various embodiments, the cancer is selected from the group consisting of breast cancer, liver cancer, colon cancer, lung cancer and prostate cancer. In some embodiments, the cancer is prostate cancer. In some embodiments, the cancer is breast cancer.

Prostate Cancer: Prostate cancer is the most common type of cancer among men in the United States. It accounts for 28% of the total cancer incidences and 10% of the total cancer deaths of American men (1). Prostate cancer-related mortality is mainly caused by advanced cancers that have disseminated and metastasized to distant organs such as the bone, lung and liver (2). Once cancer cells establish secondary tumors in these vital organs, treatment usually becomes more complicated with worse outcome. Defining and understanding novel molecular targets that drive prostate cancer progression and metastasis is important for developing effective therapeutic approaches for prostate cancer.

MTDH was shown to be overexpressed in prostate tumor tissues and tumorigenic cell lines compared to benign hyperplastic tissues and normal epithelial cells (Thirkettle et al., 2009; Kikuno et al., 2007). Knockdown of MTDH in cultured prostate cancer cells enhanced apoptosis and inhibited Matrigel invasion.

Formulations

The disclosure provides MTDH/SND1 inhibitors useful in the treatment of cancer (e.g., to inhibit or suppress growth of or metastasis of a tumor). To administer inhibitors to patients or test animals, it is preferable to formulate the products in a composition comprising one or more pharmaceutically acceptable carriers. Pharmaceutically or pharmacologically acceptable carriers or vehicles refer to molecular entities and compositions that do not produce allergic, or other adverse reactions when administered using routes well-known in the art, as described below, or are approved by the U.S. Food and Drug Administration or a counterpart foreign regulatory authority as an acceptable additive to orally or parenterally administered pharmaceuticals. Pharmaceutically acceptable carriers include any and all clinically useful solvents, dispersion media, coatings, antibacterial and antifungal agents, isotonic and absorption delaying agents and the like.

Pharmaceutical carriers include pharmaceutically acceptable salts, particularly where a basic or acidic group is present in a compound. For example, when an acidic substituent, such as —COOH, is present, the ammonium, sodium, potassium, calcium and the like salts, are contemplated for administration. Additionally, where an acid group is present, pharmaceutically acceptable esters of the compound (e.g., methyl, tert-butyl, pivaloyloxymethyl, succinyl, and the like) are contemplated as preferred forms of the compounds, such esters being known in the art for modifying solubility and/or hydrolysis characteristics for use as sustained release or prodrug formulations.

When a basic group (such as amino or a basic heteroaryl radical, such as pyridyl) is present, then an acidic salt, such as hydrochloride, hydrobromide, acetate, maleate, pamoate, phosphate, methanesulfonate, p-toluenesulfonate, and the like, is contemplated as a form for administration.

In addition, compounds may form solvates with water or common organic solvents. Such solvates are contemplated as well.

The inhibitors herein may be administered orally, parenterally, transocularly, intranasally, transdermally, transmucosally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramusclar, intramammary, intraperitoneal, intrathecal, retrobulbar, intrapulmonary injection and or surgical implantation at a particular site is contemplated as well. Generally, compositions for administration by any of the above methods are essentially free of pyrogens, as well as other impurities that could be harmful to the recipient. Further, compositions for administration parenterally are sterile.

Dosing and Administration

The MTDH/SND1 inhibitor is administered in a therapeutically effective amount; typically, the composition is in unit dosage form. The amount of inhibitor administered is, of course, dependent on the age, weight, and general condition of the patient, the severity of the condition being treated, and the judgment of the prescribing-physician. Suitable therapeutic amounts will be known to those skilled in the art and/or are described in the pertinent reference texts and literature. In one aspect, the dose is administered either one time per day or multiple times per day. The MTDH/SND1 inhibitor may be administered one, two, three or four times per day. In some embodiments, an effective dosage of inhibitor may be within the range of 0.01 mg to 1000 mg per kg (mg/kg) of body weight per day. In some embodiments, the inhibitor is administered at a daily dose ranging from about 10 mg/kg to about 250 mg/kg, or from about 100 mg/kg to about 250 mg/kg, or from about 60 mg/kg to about 100 mg/kg or from about 50 mg/kg to about 90 mg/kg, or from about 30 mg/kg to about 80 mg/kg, or from about 20 mg/kg to about 60 mg/kg, or from about 10 mg/kg to about 50 mg/kg. Further, the effective dose may be 0.5 mg/kg, 1 mg/kg, 5 mg/kg, 10 mg/kg, 15 mg/kg, 20 mg/kg/25 mg/kg, 30 mg/kg, 35 mg/kg, 40 mg/kg, 45 mg/kg, 50 mg/kg, 55 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, 250 mg/kg, 300 mg/kg, 350 mg/kg, 400 mg/kg, 450 mg/kg, 500 mg/kg, and may increase by 25 mg/kg increments up to 1000 mg/kg, or may range between any two of the foregoing values.

Administration may continue for at least 3 months, 6 months, 9 months, 1 year, 2 years, or more.

Combination Therapy

Therapeutic compositions described herein can be administered in therapeutically effective dosages alone or in combination with adjunct cancer therapy such as surgery, chemotherapy, radiotherapy, immunotherapy, thermotherapy, and laser therapy, and may provide a beneficial effect, e.g. reducing tumor size, slowing rate of tumor growth, inhibiting metastasis, sensitizing tumors to cancer treatments, or otherwise improving overall clinical condition, without necessarily eradicating the cancer. Cytostatic and cytotoxic agents that target the cancer cells are specifically contemplated for combination therapy. Likewise, agents that target angiogenesis or lymphangiogenesis, or immune therapies targeting checkpoint pathways are specifically contemplated for combination therapy.

As used herein, a "chemotherapeutic agent" is a chemical compound useful in the treatment of cancer. Examples of chemotherapeutic agents include: alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and tiimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; *vinca* alkaloids; epipodophyllotoxins; antibiotics such as the enediyne antibiotics (e.g., calicheamicin, especially calicheamicin gammaII and calicheamicin omegaII; L-asparaginase; anthracenedione substituted urea; methyl hydrazine derivatives; dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitiaerine; pentostatin; phenamet; pirarubicin; losoxantione; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2 2"-trichlorotiiethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® docetaxel (Rhone-Poulenc Rorer, Antony, France); chloranbucil; GEMZAR® gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DFMO); retinoids such as retinoic acid; capecitabine; leucovorin (LV); irenotecan; adrenocortical suppressant; adrenocorticosteroids; progestins; estrogens; androgens; gonadotropin-releasing hormone analogs; and pharmaceutically acceptable salts, acids or derivatives of any of the above. Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON-toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASL® exemestane, formestanie, fadrozole, RIVIS OR® vorozole, FEMARA® letrozole, and ARTMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF-A expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rJL-2; LURTOTECAN® topoisomerase 1 inhibitor; ABARELLX® rmRH; and pharmaceutically acceptable salts, acids or derivatives of any of the above.

In some embodiments, the peptides described herein are administered in conjunction with any number of immune checkpoint inhibitors. Immune checkpoint inhibitors include antibodies, or antigen binding fragments thereof, that bind to and block or inhibit the activity of one or more of CTLA-4, PDL1, PDL2, PD1, B7-H3, B7-H4, BTLA, HVEM, TIM3, and GALS. Exemplary immune checkpoint inhibitors include, but are not limited to, Tremelimumab (CTLA-4 blocking antibody), anti-OX40, PD-L1 monoclonal Antibody (Anti-B7-H1; MEDI4736), ipilimumab, MK-3475 (PD-1 blocker) and Nivolumamb (anti-PD1 antibody).

The treatment methods described herein optionally include monitoring the effect of the therapeutic composition on the tumor. For example, the size of the tumor can be determined, as can the presence of metastases. Also contemplated is measurement of the degree of metastasis, e.g., by measuring the number of metastatic modules or by measurement of ascites associated with metastasis.

The MTDH/SND1 inhibitor and other drugs/therapies can be administered in combination either simultaneously in a single composition or in separate compositions. Alternatively, the administration is sequential. Simultaneous administration is achieved by administering a single composition or pharmacological protein formulation that includes both the inhibitor and other therapeutic agent(s). Alternatively, the other therapeutic agent(s) are taken separately at about the same time as a pharmacological formulation (e.g., tablet, injection or drink) of the inhibitor.

Kits

The disclosure also provides kits for carrying out the methods of the disclosure. In various embodiments, the kit contains, e.g., bottles, vials, ampoules, tubes, cartridges and/or syringes that comprise a liquid (e.g., sterile injectable) formulation or a solid (e.g., lyophilized) formulation. The kits can also contain pharmaceutically acceptable vehicles or carriers (e.g., solvents, solutions and/or buffers) for reconstituting a solid (e.g., lyophilized) formulation into a solution or suspension for administration (e.g., by injection), including without limitation reconstituting a lyophilized formulation in a syringe for injection or for diluting concentrate to a lower concentration. Furthermore, extemporaneous injection solutions and suspensions can be prepared from, e.g., sterile powder, granules, or tablets comprising a composition comprising an inhibitor as described herein. The kits can also include dispensing devices, such as aerosol or injection dispensing devices, pen injectors, autoinjectors, needleless injectors, syringes, and/ or needles. In various embodiments, the kit also provides an oral dosage form, e.g., a tablet or capsule or other oral formulation described herein, of the inhibitor for use in the method. The kit also provides instructions for use.

While the disclosure has been described in conjunction with specific embodiments thereof, the foregoing description as well as the examples which follow are intended to illustrate and not limit the scope of the disclosure. Other aspects, advantages and modifications within the scope of the disclosure will be apparent to those skilled in the art.

Example 1—Generation of MTDH Knockout Mice and Effects in Tumor Progression

In order to investigate the effects of metadherin on development, progression and metastasis of breast cancer cells in vivo, metadherin knockout mice were generated.

Experimental Procedures

Mice: All experimental protocols involving mice were approved by Institutional Animal Care and Use Committee (IACUC) of Princeton University. Mtdh-KO mice were generated by injecting ES cell line XB780 (BayGenomics) into the C57BL/6 blastocysts followed by confirmation of germline transmission. KO mice were then backcrossed to FVB background for >6 generations before breeding with MMTV-PyMT, MMTV-ErbB2, MMTV-Wnt transgenic mice (Jackson Laboratory) in FVB background. To create the MMTV-Mtdh construct, mouse Mtdh coding sequence was inserted into pMMTV-SV40 vector, then the expression cassette was linearized and microinjected into the pronuclei of zygotes from FVB mice. For spontaneous tumorigenesis studies, female mice carrying the specific oncogenes were examined weekly for mammary tumors. Tumors were considered established when they became palpable for two consecutive weeks, and tumors were measured by calipers for calculation of tumor volumes (π×length×width$^2$/6). Lung nodules were counted directly after fixation (MMTV-PyMT models) or after sectioning and staining of the lungs (MMTV-ErbB2 model).

Genotyping of Mtdh knockout allele: To determine the precise insertion site of the gene trap cassette in the second intron of Mtdh locus, forward primer 5'-CTG-CAAAACAAGCACCAGAG-3' (located in the second exon of Mtdh) (SEQ ID NO: 6) and reverse primer 5'-GTTTTC-CCAGTCACGACGTT-3' (located in the targeting vector pGT0pfs) ID NO: 7) were used to amplify the fragment covering the insertion site using the Expand 20 kb PUS PCR System (Roche). The PCR product was sequenced, and the insertion site was determined to be at the 3041 bp of the second intron of Mtdh. Based on the insertion site, three genotyping primers were designed to distinguish Mtdh$^{+/+}$, Mtdh$^{+/-}$ and Mtdh$^{-/-}$ mice as indicated below. Wild-type allele corresponds to a 602 bp PCR fragment, whereas gene trap allele corresponds to a 472 bp PCR fragment. The PCR primers for genotyping the wild-type and gene-trapped Mtdh alleles are in Table 1:

TABLE 1

| Mtdh allele | Forward 5'-3' | Reverse 5'-3' |
|---|---|---|
| Wild-type | GAGAGGAGGTTTTGG GGAAG (SEQ ID NO: 8) | CCCATGTCTAAAAAG CCAATC (SEQ ID NO: 9) |
| Gene-trapped | GAGAGGAGGTTTTGG GGAAG (SEQ ID NO: 10) | GTTCATATGGTGCCG TGCAG (SEQ ID NO: 11) |

Genotyping of MMTV-Mtdh transgene: Southern blot genotyping was performed by the Transgenic & Knockout Shared Resource at the Rutgers Cancer Institute of New Jersey to confirm transgenic lines. For PCR genotyping, the primers used to identify MMTV-Mtdh transgenic progeny were designed to amplify the linking region between Mtdh and SV40, while primers targeting other genomic DNA region served as internal control. The PCR primers for genotyping the MMTV-Mtdh transgene are in Table 2.

TABLE 2

| Genotyping | Forward 5'-3' | Reverse 5'-3' |
|---|---|---|
| MMTV-Mtdh | CAAGACTCTTCCTCC TGCTATCT (SEQ ID NO: 12) | CCCATTCATCAGTTC CATAGGTTG (SEQ ID NO: 13) |
| Genomic control | CAAATGTTGCTTGTC TGGTG (SEQ ID NO: 14) | GTCAGTCGAGTGCAC AGTTT (SEQ ID NO: 15) |

Mammary carcinogenesis Mammary carcinogenesis experiments were performed using the protocol previously described. Briefly, 6-week-old female FVB/N mice with indicated Mtdh genotypes were injected subcutaneously with 15 mg MPA (Depo-Provera, NY, Pfizer) one week before receiving 1 mg DMBA (Sigma-Aldrich Chemical Co, St. Louis, Mo.) in 0.1 ml cottonseed oil by gavage weekly for four consecutive weeks. Mice were examined weekly for tumor formations.

Histology and Imunohistochemistry To detect β-galactosidase (lacZ) activity, embryos were fixed in 0.2% glutaraldehyde for 30 min, washed in phosphate-buffered saline, and incubated overnight in X-gal staining solution (1 mg/ml 4-chloro-5-bromo-3-indolyl-□-galactoside (X-gal), 4 mM K4Fe(CN)6.3H2O, 4 mM K3Fe(CN)6, 2 mM MgCl2, 0.01% deoxycholate and 0.02% Nonidet P-40 in 0.1 M sodium phosphate, pH 7.3). After being stained, embryos were further fixed in 10% phosphate-buffered formalin. For whole-mount preparation of mammary glands, the 4th inguinal mammary glands were dissected and fixed in 10% phosphate-buffered formalin overnight, followed by hydration and carmine red staining. The stained glands were then dehydrated in series of alcohol baths, defatted with histoclear reagents and mounted. For histology, formalin-fixed tissues were embedded in paraffin, sectioned, and stained with hematoxylin and eosin (H&E). For immunohistochemistry staining, antigen heat retrieval with citric buffer (pH=6) was used on paraffin-embedded sections and sections were incubated for 1 h with antibodies against PyMT (Novus Biologicals, NB100-2749, 1:200), cleaved Caspase-3 (Cell Signaling, catalogue #9664, 1:200), ERBB2 (Cell Signaling, catalogue #2165, 1:100) and p-ERBB2 (Cell Signaling, catalogue #2243, 1:200). Biotinylated secondary antibodies were incubated for 30 min followed by incubation with ABC reagents (Vector laboratories). HRP was developed in 3, 3-diaminobenzidein according to manufacturer's instructions (Invitrogen). Tissue sections were counterstained with hemotoxylin, dehydrated and mounted. To quantify cleaved-caspase 3-postive cells in FIG. 9A, more than 20 random images (>2000 cells) were taken under microscope and the positive cells were manually counted.

Tissue array immunostaining Two breast cancer tissue microarrays were used and stained with antibodies against MTDH (Invitrogen, catalogue #40-6500) and SND1 (Sigma, HPA002632). One TMA was obtained from Biomax (BR1921a) and composed of 160 primary tumors, 5 normal tissue and 27 normal adjacent tissues. Out of these 192 samples, 154 samples were stained successfully for both MTDH and SND1. A second TMA was obtained from the Cancer Institute of New Jersey (CINJ YMTA_201) and composed of 399 primary tumors. Out of these 399 samples, 270 samples were stained successfully for both MTDH and SND1. Each sample was scored as negative (0), weak (1), moderate (2), or strong (3) according to staining intensities.

Immunoprecipitation and western blot For immunoprecipitation (IP) experiments, cultured cells were washed in cold PBS and lysed in lysis buffer (20 mM Tris pH 7.4, 0.15 M NaCl, 1 mM EDTA, 1 mM EGTA, 1% Tx-100, 0.0025 M Na2P2O7, 1 mM α-glycerolphosphate, 1 mM Na3VO4, and 1 mM NaF) with an EDTA-free protease inhibitor mixture (Roche Applied Science) and PMSF. Cell lysates were then incubated on ice for 10 min, centrifuged, and precleared by incubating with protein A/G beads (Santa Cruz Biotechnology) for 1 h at 4° C. For IP bead preparation, 30 μl of protein A/G beads were incubated with 5 μg of antibodies for 2 h at 4° C. IPs were carried out for overnight at 4° C., and beads were centrifuged, washed and subsequently boiled for 5 min in SDS protein loading buffer to elute bound protein. IP lysates were subjected to western blotting with indicated antibodies.

For western blotting, tissues/tumors were removed from mice and frozen immediately in liquid nitrogen, followed by homogenization with pestle and mortar in RIPA buffer plus PMSF and protease inhibitor. For cultured cells, lysates were collected by directly adding lysis buffer on to the plate. Western blot gel preparation and immunoblotting were performed following standard procedures. Antibodies against MTDH (invitrogen, catalogue #40-6500), SND1

(Santa cruz, catalogue # sc-271590), ERBB2 (Cell Signaling, catalogue #2165), p-ERBB2 (Cell Signaling, catalogue #2243), EGFR (Cell Signaling, catalogue #4267), anti-Myc (Santa Cruz, catalogue # sc-40), and anti-HA (Santa Cruz, catalogue # sc-7392) were diluted 1:1000.

ALDEFLUOR assay and separation of the ALDH-positive population by FACS The ALDEFLUOR kit (StemCell Technologies, Durham, N.C., USA) was used to isolate the population with a high ALDH enzymatic activity according to the manufacturer's instructions. Briefly, tumor cells freshly dissociated from spontaneous or transplanted PyMT tumors were suspended in ALDEFLUOR assay buffer containing ALDH substrate (1 ml buffer containing 1 μmon BAAA per $1 \times 10^6$ cells) and incubated for 45 min at 37° C. For each sample of cells, an aliquot was treated with 50 mM ALDH inhibitor diethylaminoben-zaldehyde (DEAB) right before adding the substrate. The sorting gates were established using the cells stained with PI only (for viability) and the ALDEFLUOR-stained cells treated with DEAB as negative controls.

Human breast cancer TMAs: Two human breast TMAs were used in the study to examine the correlation of MTDH and SND1 protein levels. One TMA was purchased from US Biomax (BR1921a) and a second TMA was obtained from the Cancer Institute of New Jersey (YMTA_201). Both set of TMAs used de-identified tumor samples and were considered exempt by the Institutional Review Boards of Princeton University and the Rutgers New Jersey Medical School.

Harvesting mammary epithelial cells and flow cytometry: Single cell suspensions of mammary glands or tumors were prepared as previously described (Shackleton et al., 2006). Briefly, tissues were dissected, minced into small pieces and digested for 1 h at 37° C. in culture medium (1:1 DMEM: Ham's F-12 medium containing 5% FBS, 10 ng/ml EGF, 500 ng/ml hydrocortisone, 5 μg/ml Insulin, 20 ng/ml cholera toxin and 1% Pen/Strep) supplemented with 300 U/ml type 1A collagenase (Sigma) and 100 U/ml hyaluronidase (Sigma). Organoids were sequentially suspended with 0.25% trypsin-EDTA for 1.5 min, 5 mg/ml Dispase (Invitrogen) and 0.1 mg/ml DNase (Sigma) for 5 min, and 0.64% ammonium chloride for 5 min at 37° C. before filtration through a 40 μm nylon cell strainer and antibody staining. Mammary epithelial cells were incubated with an antibody cocktail containing CD31, CD45, TER119, CD24, CD29 and CD61 for 30 min followed by secondary antibody staining for 20 min before FACS analysis or sorting.

Limiting dilution assays: For mammary gland reconstitution assays, single cell suspensions of MECs from mammary glands of 7 or 8 week-old female mice were sorted and injected into cleared mammary fat pads of 3-week-old recipient mice. The outgrowths were analyzed at 6-8 weeks post transplantation. For tumorigenesis assays, single cell suspensions of primary MECs were transplanted into FVB WT recipient mice unless otherwise indicated.

Mammosphere/tumorsphere assays: Single cells were plated in ultralow attachment plates (Corning, Tewksbury, Mass.) with sphere media (1:1 DMEM: Ham's 12 supplemented with B27 (Invitrogen), 20 ng/mL EGF (Novoprotein), 20 ng/mL bFGF, and 4 μg/mL heparin). Spheres were counted 4-7 days after plating.

Microarray analysis: RNA was extracted from indicated tumor cells under CPT (50 μM) treatment and analyzed with Agilent Whole Mouse Genome 4×44k arrays. RNA samples were labeled with Cy5 using the Agilent Low RNA Input Linear Amplification Kit and hybridized along with the Cy3-labeled Mouse Universal Reference RNA (Stratagene). Arrays were scanned with an Agilent G2565BA scanner and analyzed with the Agilent Feature Extraction v9.5 software. The Cy5/Cy3 ratios were calculated using the feature medium signal and normalized by the array median. Genes with >2 average fold changes and Student's t-test p values<0.05 were included as SND1-regulated genes.

Lentiviral infection: For knockdown studies, pLKO plasmids containing shRNA sequences that target murine Mtdh (KD1, TRCN0000125816; KD2, TRCN0000125818), murine Snd1 (TRCN0000054742), human MTDH (KD1, TRCN0000151467; KD2, TRCN0000322872; KD3, TRCN0000322949) and Human SND1 (KD1, TRCN0000245140; KD2, TRCN0000245141; KD3, TRCN0000245144) were purchased from Sigma-Aldrich (St Louis, Mo., USA). All lentivirus construct plasmids were packaged into virus using HEK293-T cells as packaging cell lines together with helper plasmids VSVG (envelope) and p8.91 (gag-pol, pCMV-dR8.91) following standard protocols. Primary cells were either spin infected with concentrated virus-containing media supplemented with 8 μg/mL Polybrene for 2 hr at 1000 g at 4° C. and then transplanted, or cultured in plates following infections and sorted before being used in experiments.

qRT-PCR analyses: Total RNA was isolated using the RNeasy kit (Qiagen) and reverse transcribed with the Superscript III kit (Invitrogen) in accordance with the manufacturer's instructions. Quantitative PCR was performed using the SYBR Green PCR Master Mix (Applied Biosystems) with the ABI Prism 7900HT thermocycler (Applied Biosystems).

Gene set enrichment analysis (GSEA): Normalized microarray expression data were rank-ordered by expression using the provided ratio of classes (i.e. fold change) metric. Multiple probe matches for the same gene were collapsed into one value, with the highest probe reading being used in each case. SND1_CPT_UP signature contains 504 genes that are specifically upregulated by SND1 by >2 fold (p<0.05) under CPT treatment. SND1_CPT_UP signature was tested for enrichment in rank ordered lists via GSEA using the classic enrichment statistic and compared to enrichment results from 1000 random permutations of the gene set to obtain p values. Raw enrichment scores were converted to normalized enrichment scores using default GSEA parameters. Enrichment cores are defined as the members of the gene set that lie before or at the running sum peak (i.e. the enrichment score) of the ranked gene list.

Statistical analysis: All results wherever necessary were subjected to statistical analysis. A log-rank test, a non-parametric Mann-Whitney test, Chi-square test, and unpaired, two-sided, independent Student's t-test with equal variance assumption were used for most studies as indicated in figure legends. For limiting dilution assay, the frequency of MaSCs or TICs and statistics were calculated using L-calc software (StemCell Technologies). p values were denoted as *p<0.05, p<0.01, *p<0.001 in all figures.

Accession Numbers: All raw microarray data files are available in the GEO database (GSE55522).

Results

Mtdh-Knockout Mice were Viable and Grossly Indistinguishable from WT Mice

To generate Mtdh-knockout (KO) mice, the Bay Genomics gene trap database was screened and an ESC line XB780, which contains an insertion into the second intron of Mtdh that results in premature termination of transcription (FIG. 1A) was selected. Injection of XB780 ES cells into blastocysts generated chimeric mice with subsequent confirmation of germ line transmission. Crosses between Mtdh heterozygous (Mtdh+/−) mice gave rise to offspring at the Mendelian ratio. Mtdh homozygous KO (Mtdh−/−) embryos showed widespread LacZ activity (FIG. 1B), suggesting ubiquitous Mtdh expression in many embryonic organs. In adult mice, MTDH was also detected in a variety of tissues in wild-type (WT, Mtdh+/+) and Mtdh+/− mice, while undetectable in Mtdh−/− mice, confirming that the gene-trapped allele completely abolished Mtdh expression. Mtdh−/− mice were viable, fertile, and displayed no obvious abnormalities when monitored for up to two years.

MTDH was also detected in normal mammary epithelial cells (MECs) and the expression levels correlated with Mtdh genetic status (FIG. 1C). To assess the influence of MTDH deficiency in postnatal mammary gland development, whole mounts of inguinal mammary fat pads from WT and KO virgin mice were examined. Except for a transient delay in ductal outgrowth of mammary glands from 3- and 5-week-old KO mice as compared to WT littermates, significant difference in branching morphogenesis was not observed at later time points or during pregnancy and lactation. The largely comparable mammary epithelium in WT and Mtdh−/− mice starting at puberty therefore allows us to use Mtdh−/− mice to examine the necessity of MTDH for mammary tumor formation.

Mtdh KO inhibits tumor formation and metastasis in luminal mammary tumors: To dissect the roles of MTDH during autochthonous mammary tumor progression, the MMTV-PyMT and MMTV-ErbB2 transgenic models were first used, both of which develop luminal adenocarcinoma with high incidence of lung metastasis. In the aggressive MMTV-PyMT model, mammary tumors occurred as early as 42 days of age, and by day 63, 50% of Mtdh+/+ mice developed tumors (FIG. 1D). In contrast, the first palpable tumor was detected in the Mtdh−/− group at day 50, and 50% of these mice developed tumors only after 80 days. The delay in tumor occurrence was further supported by a greater number of tumor-free mammary glands in Mtdh−/− mice as compared to WT control (FIG. 1E). Consistently, the total tumor burden of PyMT;Mtdh+/− and PyMT;Mtdh−/− mice was reduced to 54% and 10% of that of WT control, respectively (FIG. 1F). Furthermore, PyMT;Mtdh−/− mice had significantly fewer (FIG. 1G) and smaller (p<0.05) metastatic nodules.

The difference in tumor formation was even more prominent in the MMTV-ErbB2 model, in which tumorigenesis occurs after long latency. While almost all ErbB2;Mtdh+/+ mice developed tumors by 300 days of age, more than 60% of ErbB2;Mtdh−/− mice had no tumors (FIGS. 1H and 1I). Even when monitored for up to 18 months, 30% of ErbB2; Mtdh−/− mice (n=68) still remained completely tumor-free, whereas all ErbB2;Mtdh+/+ mice (n=61) had either died or reached the morbidity criteria for euthanization (p<0.0001). Lung metastasis was also severely impaired in ErbB2; Mtdh−/− mice (FIGS. 1J and 1K).

The difference in mammary tumor formation was not due to the differential induction of oncogenes, as the expression of PyMT and ErbB2 was comparable between WT and KO mammary glands or tumors. In addition, the activation of ErbB2, as indicated by its phosphorylation, was not affected. Furthermore, MTDH protein levels were elevated in PyMT and ErbB2-driven tumors as compared to age-matched normal controls, suggesting that high levels of MTDH may confer growth advantage to MECs during tumorigenesis.

Mtdh KO restrains the formation of basal-like and mixed subtypes of mammary tumors: The investigation of MTDH in tumor formation was expanded to the MMTV-Wnt model, which develops tumors that exhibit mammary stem cell (MaSC)-like gene expression profiles and resemble the basal subtype of human breast cancer (Herschkowitz et al., 2007). While virtually all Wnt;Mtdh+/+ mice succumbed to cancer at 300 days of age, no tumors were detected in 35% of Wnt;Mtdh+/− and 62% of Wnt;Mtdh−/− mice (FIG. 1L). The multiplicity of tumors was also highly dependent on the gene dosage of Mtdh (FIG. 1M). These phenotypes markedly resembled what we observed in the luminal tumor models. To broaden our analysis, we induced mammary carcinogenesis using combined treatment of medroxyprogesterone acetate (MPA) and 7, 12-dimethylbenzanthracene (DMBA) (FIG. 1N), which resulted in the formation of mammary tumors with histological characteristics of adenocarcinoma, adenosquamous carcinoma and adenomyoepithelioma carcinoma (Yin et al., 2005). Again, Mtdh−/− females showed markedly attenuated tumor susceptibility after MPA/DMBA treatment (FIGS. 1N and 1O).

Mtdh KO impairs the expansion and activities of oncogene-induced basal and luminal TICs: The dramatic effect of Mtdh deletion on mammary tumor formation prompted investigatation of early events during tumorigenesis. To this end, we examined whole mounts (FIG. 2A, top panels) and haematoxylin/eosin-stained sections (FIG. 2A, bottom panels) of mammary glands from different tumor models at preneoplastic stages were examined. Both the PyMT and Wnt oncogenes induced extensive hyperplasia as early as four weeks in Mtdh+/+ mice; however, Mtdh−/− glands exhibited significantly fewer and smaller hyperplasia foci mingled with normal ductal structures. MMTV-ErbB2 mice have the longest tumor latency, and this corresponds to significantly delayed and the least severe hyperplasia. Whole mount analysis of mammary glands from 6-month-old tumor-free MMTV-ErbB2 females revealed close to 100% incidence of hyperplasia in Mtdh-positive mice, while only 20% of those from ErbB2;Mtdh−/− were mildly hyperplasic (FIGS. 3A and 3B).

These severely impaired preneoplastic changes in Mtdh−/− glands may suggest a defect in the expansion of transformed MECs. To examine oncogene-induced changes in the cellular composition of mammary glands, preneoplastic mammary glands were profiled using CD24, CD29 ((31 integrin) and CD61 (β3 integrin), which have been previously used to resolve luminal and basal mammary epithelial subsets (Asselin-Labat et al., 2007; Shackleton et al., 2006). Compared to normal glands, PyMT preneoplastic tissues displayed a drastic expansion of the Lin−CD24+CD29low luminal subset (CD24+CD29low) (FIGS. 2B and 2C), consistent with previous reports of "luminal-like" gene expression profiles (Herschkowitz et al., 2007). In contrast, the percentage of Lin−CD24+CD29high (CD24+CD29hi) basal population, which enriches for MaSCs, was markedly increased in preneoplastic tissues from Wnt mammary glands (FIGS. 2B and 2D), as previously noted (Shackleton et al., 2006), suggesting that this population represents a key cell target for transformation in this model. Intriguingly, these oncogene-specific perturbations of the epithelial hierarchy were compromised by Mtdh loss, as evidenced by (1) the lack of CD24+CD29low luminal subset expansion in PyMT;Mtdh−/− glands (FIGS. 2B and 2C); (2) a significant decrease in the expansion of CD24+CD29hi basal subset in Wnt;Mtdh−/− glands (FIGS. 2B and 2D) compared to WT counterparts. Of note, PyMT or Wnt-induced hyperplastic glands in Mtdh+/+ mice did not exhibit a selective expansion of CD61+ population as compared to normal glands (FIGS. 3C and 3D, compare orange bars). However, the percentage of CD61+ cells, which were more capable of forming mammospheres than CD61− cells (FIG. 3E), was significantly decreased in Wnt;Mtdh−/− glands as compared to Wnt;Mtdh+/+ glands (FIGS. 3C and 3D, compare WT versus KO).

To test whether Mtdh−/− preneoplastic glands indeed contain fewer TICs, we dissociated primary MECs (pMECs) from Mtdh+/+ and Mtdh−/− preneoplastic glands and performed in vitro mammosphere formation assays. Mtdh−/− pMECs formed a decreased number of spheres across multiple tumor models (FIG. 2E). Moreover, when orthotopically transplanted into WT recipient mice, PyMT;Mtdh−/− pMECs contained substantially fewer tumor-repopulating cells in vivo as revealed by reduced tumor incidence when a series of diluting numbers were tested (FIG. 2F).

It was then analyzed whether PyMT-induced TICs exist in the expanded luminal population. Sorted luminal and basal pMECs from preoplastic glands of PyMT mice were transplanted in vivo. Tumors were detected at high frequency in mice that received luminal but not basal cells (FIG. 2G), suggesting PyMT-induced preneoplastic TICs were co-purified with luminal subset of MECs. Importantly, when the tumorigenic capabilities of luminal cells from PyMT;Mtdh+/+ and PyMT;Mtdh−/− females were examined in vivo, tumor incidence (FIG. 2H) and volumes (FIG. 2I) were substantially decreased in mice transplanted with Mtdh−/− cells. These results suggest that not only the expansion, but also the tumorigenic potential of luminal cells is severely compromised in PyMT;Mtdh−/− mice.

A selective expansion of either luminal or basal subset of MECs was not detected in MMTV-ErbB2 pre-neoplastic glands as compared to normal control, in accordance with a previous report (Shackleton et al., 2006). To identify which subset of MECs serves as TICs, luminal and basal MECs were sorted from ErbB2;Mtdh+/+ hyperplastic glands and orthotopically transplanted these cells. Palpable tumors were detected in 100% of the mice that received either luminal or basal MECs (FIGS. 3F and 3G). Regardless of cell origin, all tumors closely resembled spontaneous tumors from MMTV-ErbB2 mice in histology (FIG. 3H). These results suggest MMTV-ErbB2 tumors may originate from both luminal and basal compartments, and basal cells can give rise to luminal type of tumors, a finding supported by a recent report (Zhang et al., 2013a). To identify the cellular targets that are dependent on MTDH, luminal and basal subsets from ErbB2;Mtdh−/− females were translplanted in vivo. Strikingly, neither luminal nor basal ErbB2;Mtdh−/− cells gave rise to palpable tumors at the time when all the mice receiving ErbB2;Mtdh+/+ cells had developed large tumors (FIGS. 3F and 3G). These results indicate that MTDH is critical for maintaining ErbB2-induced basal and luminal TICs.

In contrast to its essential role in regulating TICs at early tumorigenesis, MTDH is largely dispensable for adult MaSCs activities, as indicated by similar in vivo mammary gland reconstitution (FIG. 3I) efficiency of either unfractionated Lin− MECs (FIG. 3J) or MaSCs-enriched basal cells (FIGS. 3K and 3L) from WT and KO mice.

MEC-intrinsic role of MTDH in promoting mammary tumor-initiating capacities: As MTDH is widely expressed in mice, the tumorigenesis defects in whole-organism KO mice could result from either loss of MTDH in MECs or other cell/tissue types. To distinguish between these two possibilities, mouse MTDH was re-introduced specifically in MECs of Mtdh−/− mice in vivo and it was tested whether this would rescue the tumorigenic defects. To this end, a MMTV-Mtdh transgenic mouse line was created (FIGS. 4A, 5A and 5B) and expression of the Mtdh transgene was observed specifically in the mammary gland, and, to a lesser extent, the salivary gland (FIG. 5C). Next, these MMTV-Mtdh mice were crossed with PyMT;Mtdh−/− mice to generate PyMT;Mtdh−/− mice with or without exogenous Mtdh transgene (FIG. 4A). Notably, transgene (Tg)-rescued PyMT;Mtdh−/− tumors expressed similar levels of MTDH as that of PyMT;Mtdh+/+ tumors (FIG. 4B). A nearly two-fold increase in the expansion of luminal cells from PyMT;Mtdh−/−+Tg preneoplastic glands was observed as compared to PyMT;Mtdh−/− mice (FIG. 4C). In addition, tumor onset was accelerated (FIG. 4D) and tumor burden (FIGS. 4E and 4F) was increased in the PyMT;Mtdh−/−+Tg group. The presence of the Mtdh transgene did not alter the histology of the resulting tumors (FIG. 5D). These results strongly support a tumor-intrinsic role of MTDH in promoting target cell expansion and subsequent mammary tumorigenesis in vivo, although the contribution of the tumor stroma cannot be ruled out.

To complement our spontaneous tumor model studies, it was next investigated whether acute manipulation of MTDH also affects the tumorigeneic potential of preneoplastic MECs. MTDH was knocked down in pMECs freshly dissociated from preneoplastic glands of PyMT;Mtdh+/+ (FIG. 4G) and ErbB2;Mtdh+/+ (FIG. 5E) females. The sphere-forming capability of MTDH-knockdown (KD) cells was significantly reduced in multiple independent samples in both models (FIGS. 4G and 5E). In vivo tumor formation of PyMT;Mtdh+/+ pMECs was also severely impaired by MTDH KD (FIG. 4H). Conversely, when MTDH was restored in PyMT;Mtdh−/− pMECs via lentivirus transduction to a level that was comparable to WT counterparts, both in vitro sphere and in vivo tumor formation were significantly enhanced (FIGS. 4I, 4J and FIGS. 5F-5H).

It was next analyzed whether TICs from established MTDH-positive tumors rely on MTDH for their functionality (FIG. 4K). The fact that established tumors from PyMT, Wnt, and ErbB2-driven tumor models displayed one relatively homogenous population when profiled with CD24 and CD29 (Vaillant et al., 2008) highlights the need for other markers to identify TICs from established tumors. Increased aldehyde dehydrogenase (ALDH) activity has been found in cancer stem-like populations in multiple cancer types including breast cancer (Ginestier et al., 2007), but its use as a TIC marker in mouse models remains less characterized. ALDH+ and ALDH− cells were sorted from PyMT tumors, and it was found that ALDH+ cells exhibited significantly higher in vitro sphere-forming (FIG. 4L) and in vivo tumor-initiating activities compared to ALDH− cells. Consistent with the ALDH+ population having TIC characteristics, tumors generated by this population recapitulated the phenotypic heterogeneity of the initial tumor, with a similar ratio of ALDH+ and ALDH− cells. This indicates that ALDH+ tumor cells are able to self-renew, as well as to differentiate into ALDH− cells. When MTDH was knocked down in freshly isolated ALDH+ cells from PyMT;Mtdh+/+ tumors, the sphere-forming activity was significantly reduced (FIG. 4M). For MMTV-Wnt tumors, the CD61+ population has been demonstrated to possess TIC characteristics and was highly tumorigenic (Vaillant et al., 2008). Consistently, CD61+ tumor cells were capable of generating a greater number of tumor spheres than CD61− cells (FIG. 4N). Importantly, MTDH KD compromised the sphere-forming activities in CD61+ cells from MMTV-Wnt tumors (FIG. 4O). These results suggest that MTDH is continuously required for the full functionality of TICs in MTDH-positive tumors.

Pro-tumorigenic role of MTDH requires its interacting partner SND1: SND1 has been previously identified as the major binding partner of MTDH in human breast cancer cells and it had metastasis-promoting functions similar to MTDH (Blanco et al., 2011). In this study, it was found that the interaction between MTDH and SND1 was well conserved in human and murine breast cancer cells.

To test the necessity of SND1 for the function of MTDH in tumor initiation, SND1 was first knocked down in PyMT; Mtdh−/− tumor cells, and was shown to rescue the expression of mouse MTDH in these cells (FIG. 6A). Reintroduction of MTDH in PyMT;Mtdh−/− tumor cells consistently promoted sphere formation in vitro (FIG. 4B) and tumor formation in vivo (FIG. 6C); however, this effect of MTDH was completely abolished upon SND1 KD (FIGS. 6B and 6C). If MTDH indeed requires SND1 for its pro-tumorigenic function, it was expected that knockdown of SND1 in Mtdh+/+ tumor cells would phenocopy the effect of MTDH deficiency on mammary tumorigenesis. Indeed, SND1 KD in Mtdh+/+ tumor cells impaired sphere-forming activities in vitro (FIG. 6D) and tumor initiation in vivo (FIGS. 6E and 6F), resembling the effect of MTDH ablation on tumor initiating activities. These results together indicate that MTDH's function on TICs requires the presence of SND1.

To further test whether the physical interaction with SND1 is critical for the function of MTDH, detailed analysis on the interaction of the proteins was conducted. SND1 contains four N-terminal Staphylococcal nuclease (SN) repeats and a C-terminal Tudor-SN hybrid domain. An SND1 construct missing the C-terminal sequence following the second SN domain (SND1ΔC, 1-339) bound stoichiometrically with MTDH fragment 364-582, but not with MTDH fragment 1-289 (FIGS. 7A and 7B), resembling the binding behavior of full-length SND1 (Blanco et al., 2011). This allowed us to use the SND1ΔC fragment for the following in vitro binding studies. To map the minimal SND1-binding domain of MTDH, a series of fragments of MTDH within region 364-582 was generated (FIG. 7A), and their interaction with SND1ΔC was tested. This led to the identification of a 22 amino-acid fragment (residues 386-407) sufficient for SND1-binding (FIGS. 7A and 7B), which was further confirmed by the crystal structure of the MTDH-SND1 complex (see Example 3).

Figure 7A:
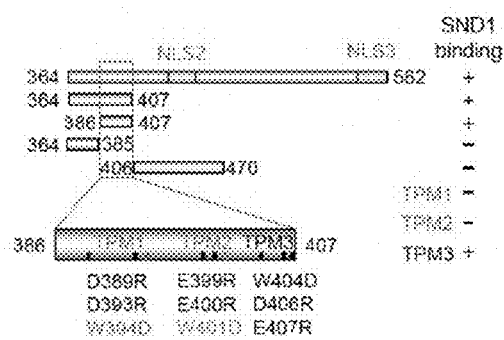
FIGS. 7A-E represents determination of key regions and residues mediating the MTDH-SND1 interaction.
Figure 7B:
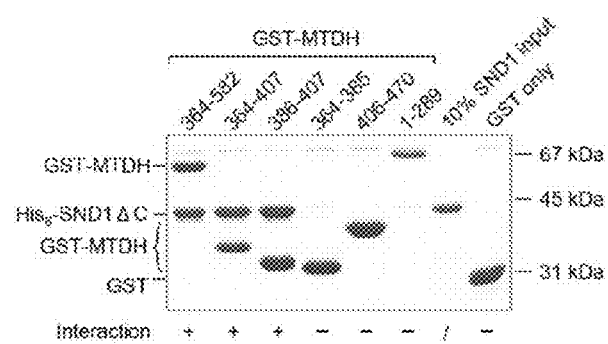
Figure 7C:
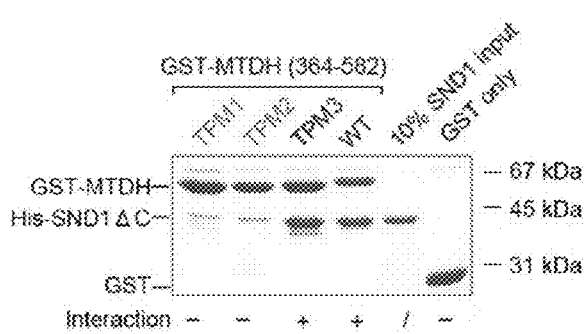

To determine key residues of MTDH that are essential for the interaction, three triple-point mutants (referred to as TPM) were designed, with each harboring 3 amino acid mutations within the 22-aa minimal binding domain in the MTDH (amino acids 364-582 of SEQ ID NO: 1) fragment (FIG. 7A). TPM1 comprises mutations D389R, D393R and W394D. TPM2 comprises mutations E399R, E400R and W401D. TPM3 comprises mutations W404D, D406R and E407R. In vitro binding assays showed that both TPM1 and TPM2 could not bind SND1ΔC whereas TPM3 bound SND1ΔC as effectively as the WT MTDH (FIG. 7C). The mutations are also set out in Table 3.

TABLE 3

Single or triple mutant constructs for human and murine MTDH/Mtdh

| Con-structs | Con-structs | Mutation (human MTDH) | Mutation (mouse Mtdh) |
|---|---|---|---|
| TPM1 | SPM11 | D389R (GAT/CGT) | D386R (GAC/CGT) |
|  | SPM12 | D393R (GAT/CGT) | D390R (GAC/CGT) |
|  | SPM13 | W394D (TGG/GAC) | W391D (TGG/GAC) |
| TPM2 | SPM21 | E399R (GAA/CGT) | E396R (GAG/CGT) |
|  | SPM22 | E400R (GAG/CGT) | E397R (GAG/CGT) |
|  | SPM23 | W401D (TGG/GAT) | W398D (TGG/GAT) |

TABLE 3-continued

Single or triple mutant constructs for human and murine MTDH/Mtdh

| Con-structs | Con-structs | Mutation (human MTDH) | Mutation (mouse Mtdh) |
|---|---|---|---|
| TPM3 | SPM31 | W404D (TGG/GAT) | W401D (TGG/GAT) |
|  | SPM32 | D406R (GAC/CGT) | D403R (GAT/CGT) |
|  | SPM33 | E407R (GAA/CGT) | E404R (GAA/CGT) |

Figure 7D:
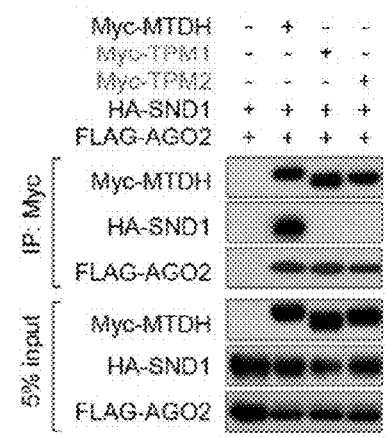
Figure 7E:
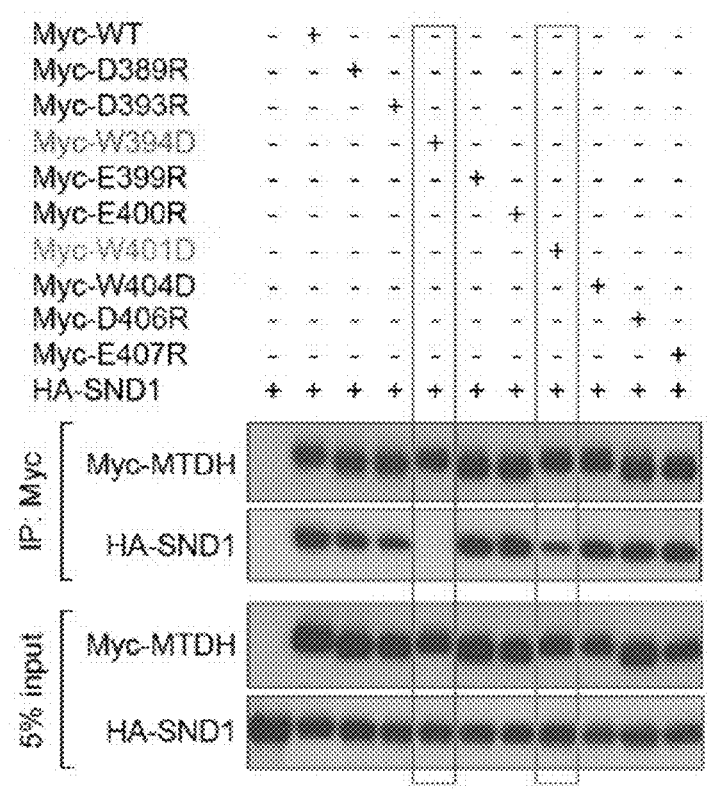

To examine whether TPM1 and TPM2 interact with SND1 in vivo, full-length HA-tagged SND1 and Myc-tagged MTDH were ectopically expressed in HEK293T cells and the cell lysates were subjected to anti-Myc immunoprecipitation. Consistent with the findings from in vitro binding assays (FIG. 7C), HA-SND1 was pulled down with WT but not TPM1 or TPM2 MTDH (FIG. 7D). All 9 individual mutations were further analyzed using similar strategies and it was found that W394D completely and W401D partially abolished the binding, whereas other mutations individually did not affect the interaction (FIG. 7E). It was noted that SND1-binding deficient TPM1 and TPM2 MTDH were still able to interact with AGO2 (FIG. 7D), another known binding partner of MTDH (Yoo et al., 2011), suggesting that these mutations are unlikely to cause gross conformational changes in MTDH, but rather selectively disrupt the interaction with SND1.

It was the tested whether these mutations affect MTDH's function in tumorigenesis. Murine forms of WT MTDH, TPM1 or TPM2 were stably expressed in PyMT;Mtdh−/− tumor cells and it was found that these MTDH mutants lost the ability to interact with SND1 (FIG. 8A). Functionally, WT MTDH was able to increase sphere-forming activities of PyMT;Mtdh−/− cells in vitro and tumor initiation in vivo, whereas TPM1 or TPM2 mutants failed to do so (FIGS. 8B-8D). Similar results were observed when the W391D mutant (corresponding to W394D in human MTDH) was tested (FIGS. 8E-8H). These results strongly suggest that binding residues of MTDH with SND1 are highly conserved in human and mice, and the interaction with SND1 is critical for mediating the functionality of MTDH in regulating TICs activities.

Figure 9A:
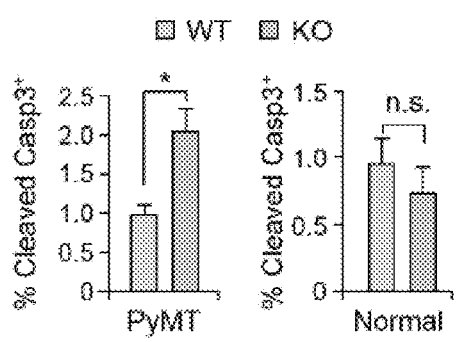
Figure 9B:
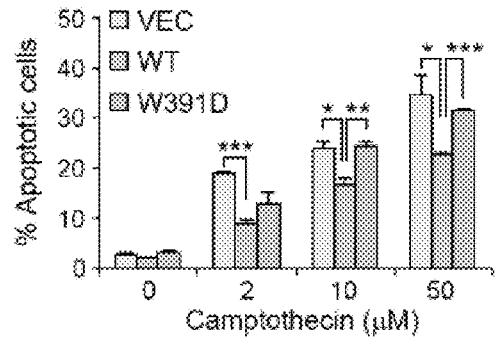

MTDH-mediated stabilization of SND1 confers MECs survival advantage under stress conditions: SND1 has been reported as a survival factor under various stress conditions (Gao et al., 2010; Sundstrom et al., 2009; Weissbach and Scadden, 2012). The more prominent role of MTDH in tumor initiation but not normal physiology of mammary glands led to a hypothesis that MTDH, through its interaction with SND1, confers MECs advantages under stress conditions during tumorigenesis. Supporting this hypothesis, it was detected herein that a significantly higher percentage of apoptotic cells in pre-neoplastic PyMT;Mtdh−/− mammary epithelium than in PyMT;Mtdh+/+ counterparts, which was not seen in glands without PyMT (FIG. 9A). To test the role of MTDH-SND1 interaction under stress conditions in vitro, we treated PyMT;Mtdh−/− pMECs, reconstituted with either WT or mutant mouse MTDH, with camptothecin (CPT) to induce DNA replication stress (FIG. 9B), a common type of stress during tumor development (Halazonetis et al., 2008). CPT treatment induced apoptosis of MECs in a dosage-dependent manner (FIG. 9B). There were a significantly decreased percentage of apoptotic cells in MTDH-rescued group compared to control, and SND1-binding deficient mutations ablated this pro-survival effect of MTDH (FIG. 9B).

Figure 9C:
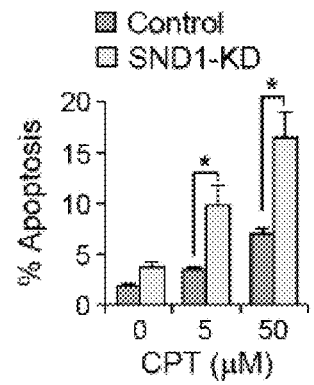
Figure 9D:
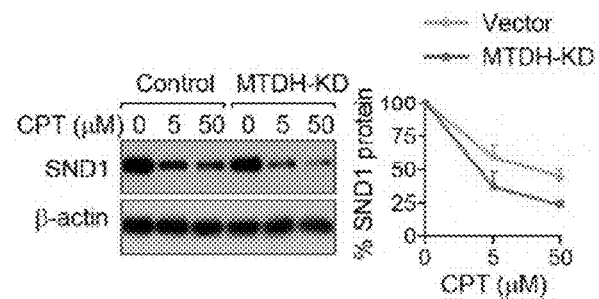
Figure 9E:
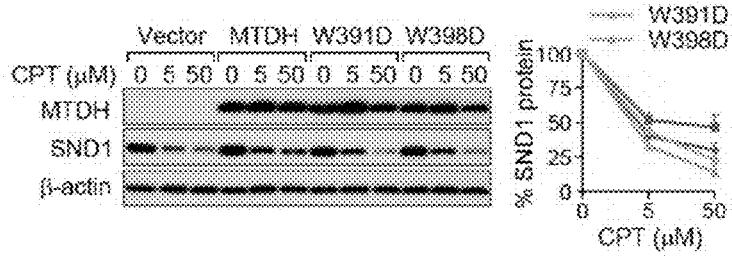

Consistent with previous observation that SND1 levels are critical for cell survival under stress conditions, silencing of SND1 in PyMT;Mtdh+/+ MECs led to a significant increase in apoptosis upon CPT treatment (FIG. 9C). Interestingly, a drug dosage-dependent decrease of SND1 protein levels was observed in MECs treated with CPT (FIG. 9D). This phenomenon was not unique to this type of stress, as heat shock treatment also resulted in rapid decrease of SND1. Notably, silencing of MTDH in PyMT;Mtdh+/+ pMECs accelerated the decrease of SND1 protein (FIG. 9D). Conversely, restoration of WT, but not SND1-binding deficient MTDH, in PyMT;Mtdh−/− MECs stabilized SND1 protein under these stress conditions (FIG. 9E). Thus, these data collectively suggest that MTDH promotes survival under stress conditions by interacting and stabilizing survival factor SND1.

Figure 9F:
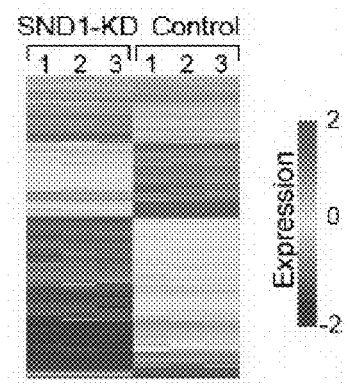

To provide a better understanding of how SND1 exerts its pro-survival function, transcriptomic profiling was performed on control versus SND1-KD PyMT;Mtdh+/+ pMECs under CPT treatment (FIGS. 9F-9H). Ingenuity Pathway Analysis revealed that genes upregulated by SND1 (FIG. 9F, >2 fold change, p<0.05) showed a significant enrichment for molecular and cellular functions including "cell death and survival", "cell cycle" and "DNA repair" (FIG. 9G), processes related to CPT-induced replication stress. Interestingly, a significant portion of SND1-upregulated genes were implicated in the "cell death and survival" category and the expression of these genes collectively was predicted to significantly activate cell viability function (FIG. 9H, top six rows) and compromise cell death and apoptosis (FIG. 9H, bottom two rows). Therefore, the ability of SND1 to globally activate pro-survival genes may underlie its role in protecting cells from stress-induced cell death (FIG. 9C). To substantiate the hypothesis that MTDH regulates survival through interacting and stablizing SND1, PyMT;Mtdh−/− pMECs reconstituted with either WT or SND1-binding deficient mutant mouse MTDH (W391D) were profiled. Gene set enrichment analysis (GSEA) demonstrated that SND1-upregulated gene signature was significantly enriched in PyMT;Mtdh−/− pMECs reconstituted with WT versus mutant MTDH (FIG. 9I).

MTDH and SND1 are important for tumor-initiating activities of human breast cancer cells: To demonstrate the important roles of both MTDH and SND1 in tumor-initiating activities in human breast cancer, MTDH or SND1 were silenced in multiple human breast cancer models, including: (1) HER2/Neu-transformed human breast epithelial cells (HMLE-N) (Mani et al., 2008) (FIGS. 10A, 10B, 11A and 11B), (2) human primary patient-derived xenografts (DeRose et al., 2011; Zhang et al., 2013b) (FIGS. 10C, 10D, 11C and 11D), and (3) the MDA-MB-231 human breast cancer cell line (FIGS. 10E-10H). Knockdown of either MTDH or SND1 significantly reduced in vitro tumorsphere formation of all models tested and tumor initiation of MDA-MB-231 cells in vivo.

Figure 11A:
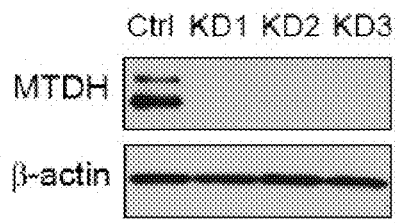
Figure 11B:
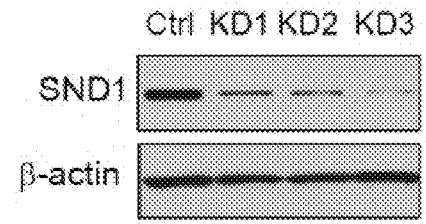
Figure 11C:
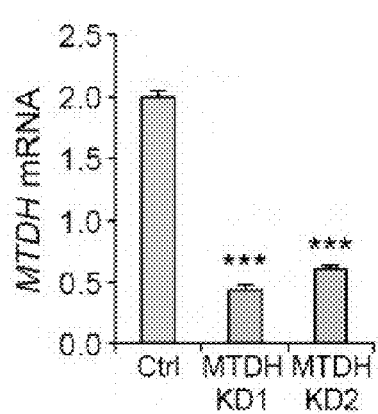
Figure 11D:
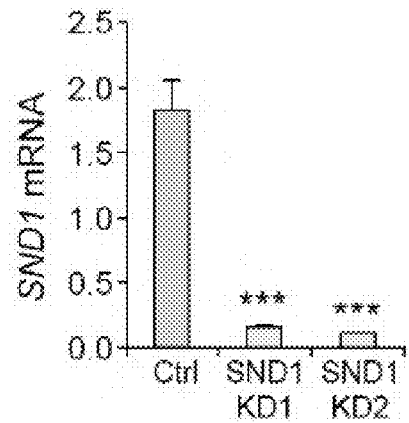
Figure 11E:
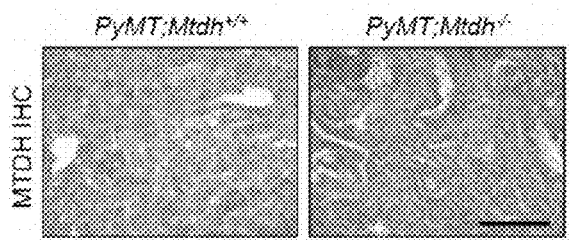
Figure 11F:
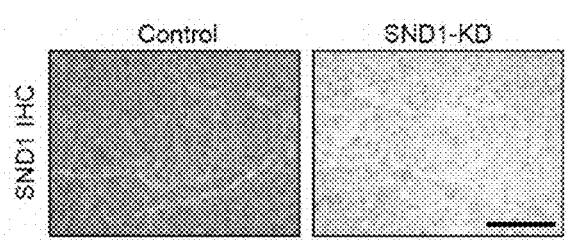

It was further examined whether MTDH-mediated stabilization of SND1 occurs in human breast cancer samples. A human breast cancer tissue microarray (TMA) was stained with antibodies against MTDH and SND1 (FIGS. 10I-10J), after confirming the specificity of the antibodies (FIGS. 11E and 11F). A positive correlation between staining scores of MTDH and SND1 (FIGS. 10I and 10J) was found, which was confirmed using an independent TMA (FIGS. 11G and 11H). Of note, MTDH and SND1 were not correlated at the mRNA levels (FIG. 11I). These data support a key role of MTDH in posttranscriptional regulation of SND1 in breast cancer, consistent with our findings that MTDH interacts and stabilizes SND1 under stress conditions during tumorigenesis.

Figures 11J, 11K, 11L:
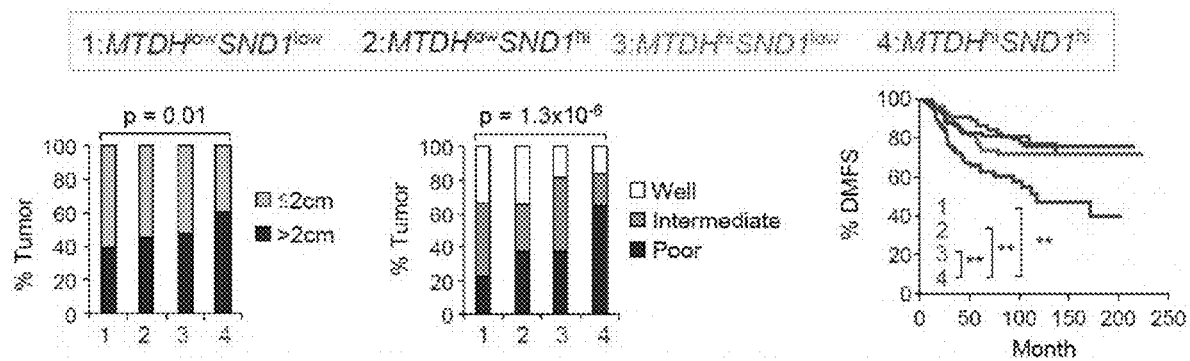
Figure 11M:
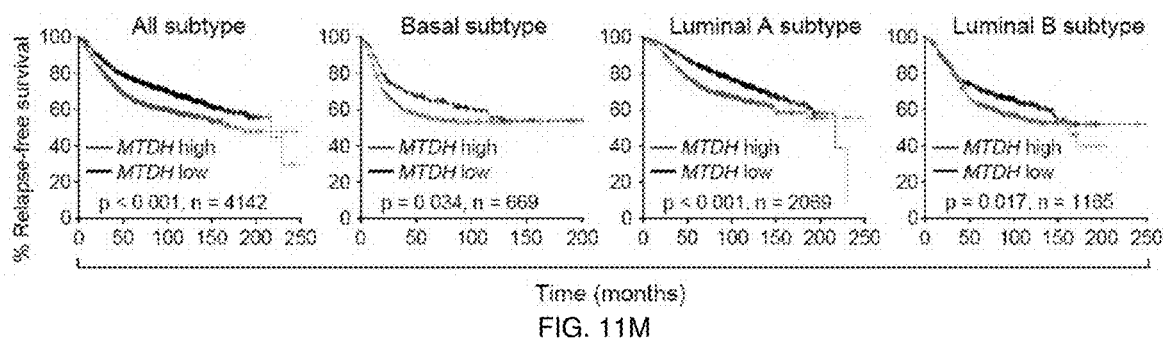

To further explore the clinical importance of the MTDH-SND1 interaction, the NKI295 human breast cancer microarray data set (van de Vijver et al., 2002) was analyzed. Patients were stratified into four different groups based on median expression for both SND1 and MTDH. Primary tumors with high mRNA levels of both MTDH and SND1 were significantly larger (FIG. 11J), less differentiated (FIG. 11K) and correlated with a shorter distant metastasis free survival (FIG. 11L), supporting a functional cooperation between MTDH and SND1 in human breast cancer in tumor development, metastasis and recurrence. Consistent with its tumor-promoting function in diverse mammary tumor models, it was also found that higher levels of MTDH predicted poor prognosis across multiple breast cancer subtypes in the KM-plotter dataset (FIG. 11M). Not to be bound by theory, but it appears that the seemingly stronger prognostic power of MTDH in luminal A subtype is likely due to a significantly larger sample size in this group compared to other subtypes.

Discussion

While the classical clonal evolution theory of tumor progression postulates that metastatic capabilities are endowed by random genetic changes occurring in rare cells within the primary tumor, genomic and clinical studies paradoxically demonstrate that the likelihood to metastasize can be predicted by profiling the bulk of primary tumors (van de Vijver et al., 2002). This suggests metastatic potential may be conferred by oncogenic events that possess additional metastasis-promoting functions (Bernards and Weinberg, 2002), and therefore these genetic changes can occur and be selected early in tumor evolution (Vanharanta and Massague, 2013). Supporting this notion, several metastasis-promoting genes have been shown to promote primary tumor growth in xenograft models (Vanharanta and Massague, 2013; Wan et al., 2013). The recurrent amplification/overexpression of MTDH in human primary breast tumors may therefore implicate MTDH in tumorigenesis in addition to its reported role in promoting breast cancer metastasis. While previous studies using human or murine breast cancer cell lines failed to reveal any effect of MTDH on primary tumor formation in xenograft models (Brown and Ruoslahti, 2004; Hu et al., 2009), genetically engineered mouse models used in current study enable us to uncover a role of MTDH in regulating the expansion and activities of tumor initiating cells at early stages of tumorigenesis, thus establishing another molecular link between primary tumor initiation with the acquisition of metastatic traits. This effect of MTDH on tumor initiation has likely been masked when a large number of highly aggressive and late-stage tumor cells were used in previous xenograft studies. Consistent with this speculation, when late-stage PyMT tumor cells were transplanted in large quantities, no difference was observed in tumor initiation between Mtdh WT and KO cells. Nevertheless, TICs from MTDH-positive established mammary tumors, such as ALDH+ cells and CD61+ cells from PyMT and Wnt-induced tumors, respectively, remain sensitive to MTDH inhibition, suggesting that MTDH-dependent mechanisms are at play in established tumors to maintain the optimal functionality of TICs, and therefore blocking MTDH and its regulated pathways will be beneficial to cancer patients with aberrant expression of MTDH.

It has been suggested that initiating genetic lesions exert a significant influence on the histopathology and molecular features of mammary tumors from both humans and transgenic animals. For example, Wnt signaling induces mammary tumors with features resembling more primitive progenitor cells as compared to PyMT and ErbB2 (Li et al., 2003). Remarkably, it was discovered herein that MTDH is required for the functionality of TICs across these different tumor models. Consistently, MTDH expression does not significantly correlate with specific subtypes of human breast cancer (Hu et al., 2009) and higher levels of MTDH predict poor prognosis across different subtypes. These results together corroborate the idea that MTDH promotes tumor initiation in an oncogene- and lineage-independent manner, in contrast to lineage-specific tumor-promoting genes, such as luminal tumor survival factor PDEF (Buchwalter et al., 2013). The broad function of MTDH in tumorigenesis is also in agreement with its frequent upregulation in a diverse spectrum of cancer types (Emdad et al., 2013; Wan and Kang, 2013).

Tumors formed in the absence of MTDH exhibited similar histological features as MTDH-positive tumors, suggesting that MTDH may not alter the cell of origin or cell fate of TICs, but instead influence their tumorigenic potential. This, together with the observation that Mtdh KO had little effect on the activities of MaSCs, establish MTDH as a critical regulator of TICs that is distinct from other cell fate regulators, such as Wnt signaling (Lento et al., 2013), Slug/Sox9 (Guo et al., 2012) and GATA3 (Kouros-Mehr et al., 2008), which regulate tumorigenesis by virtue of their abilities to mediate the conversion between differentiated cells and more primitive stem/progenitor cells in both normal and malignant contexts.

The inventors and others have identified SND1 as a major binding partner of MTDH (Blanco et al., 2011; Meng et al., 2012; Yoo et al., 2011). However, discrepancy existed regarding the binding domains of MTDH with SND1, as two non-overlapping regions of MTDH, namely amino acid 364-470 (Blanco et al., 2011) and 101-205 (Yoo et al., 2011), were each independently mapped as the only essential domain mediating MTDH's interaction with SND1. Our current study further determines a minimal fragment of MTDH (386-407) sufficient for the interaction and identifies two key residues within this fragment critical for the interaction. These findings enabled the current demonstration that the interaction with SND1 is pivotal for the function of MTDH. These findings also establish SND1 as an important regulator of mammary TICs. Importantly, the interaction between MTDH and SND1 as well as the binding residues are well conserved between human and mice, highlighting the possibility that our findings in mouse models may be highly relevant to human cancer, as suggested by the current functional and clinical analyses.

Tumorigenesis is accompanied by diverse stresses that tumor cells have to overcome, including oncogene-induced DNA replication/damage stress. It was demonstrated herein that SND1 is required for the expression of a cohort of pro-survival genes in cells under stress conditions, and silencing of SND1 sensitizes transformed MECs to replication stress-induced apoptosis. These results are consistent with previous reports that established SND1 as a pro-survival protein under various stress conditions (Gao et al., 2010; Sundstrom et al., 2009; Weissbach and Scadden, 2012). Furthermore, the physical interaction with MTDH is essential to protect SND1 from degradation and sustain SND1-regulated gene signature under stress conditions. It is thus possible that MTDH protects TICs from attritions under stress conditions during tumorigenesis, at least in part, by virtue of its ability to interact with and stabilize SND1. It remains unclear how SND1 regulates downstream pro-survival genes. SND1 is a multifunctional protein that has been reported to be involved in several gene regulatory processes, including transcriptional control, mRNA splicing, RNA stress granule formation, and RNA-induced silencing complex (RISC) machinery (reviewed in Wan and Kang, 2013). Future studies are warranted to investigate how SND1 modulates gene expression in response to stress conditions to promote cellular survival.

In addition to providing a molecular link between tumor initiation and metastatic capabilities, our findings suggest several lines of potential translational applications. First, the functional importance of MTDH and SND1 in sustaining TIC function, validated in patient-derived tumor grafts, may establish these proteins as potential therapeutic targets in cancer treatment. In addition, the results on the MTDH-SND1 interaction may facilitate the screening or design of small molecule inhibitors that can disrupt the interaction of MTDH and SND1. Our results also highlight the tumor-specific requirement of MTDH, and suggest that systemic targeting of the MTDH-SND1 module may be well tolerated by cancer patients, as whole-organism knockout of Mtdh does not cause significant defect in mice.

Example 2—Investigation of MTDH in Prostate Cancer

In order to investigate the effects of MTDH in prostate cancer, MTDH knockout mice were crossed with transgenic adenomcarcnoma of mouse prostate (TRAMP) mice in order to generate animals that have heterogenous expression of MTDH and TRAMP. The TRAMP model results in animals in which the expression of the SV40 T antigen is controlled by the rat Probasin promoter and induced during sex maturity of the mice, leading to prostate cancer development that resembles the clinical progression of human prostate cancer (Greenberg et al., 1995; Gingrich et al., 1999).

Experimental Procedures

Mice. All experimental protocols involving mice were approved by the Institutional Animal Care and Use Committee (IACUC) of Princeton University. Mtdh−/− mice were generated by injecting ES cell line XB780 (Bay Genomics) containing a gene-trapped allele of Mtdh into C57BL/6 blastocysts followed by confirmation of germline transmission by PCR. All Mtdh−/− mice were backcrossed to C57BL/6 background for >6 generations before breeding with C57BL/6 TRAMP transgenic mice (Jackson Laboratory) (Greenberg, 2005). Female TRAMP mice were bred to Mtdh−/− male mice to obtain female TRAMP/Mtdh+/− and male Mtdh+/− founder mice. Subsequently, these founder mice were bred to generate TRAMP/Mtdh+/+, TRAMP/Mtdh+/−, and TRAMP/Mtdh−/− male mice. This breeding strategy ensured that all experimental mice were heterozygous to the SV40 transgene. DNA was extracted from the tail biopsy and PCR was performed for genotypic analysis using the following primers: (1) common forward primer 5'-GAGAGGAGGTTTTGGGGAAG-3' (SEQ ID NO: 8); (2) reverse primer for WT allele 5'-CCCATGTCTAAAAAGCCAATC-3' (SEQ ID NO: 9); (3) reverse primer for mutant allele 5'-GTTCATATGGTGCCGTGCAG-3' (SEQ ID NO: 11). For tumor cell injection, athymic nude male mice were injected subcutaneously with $5 \times 10^5$ TRAMP-C1 cells, and tumors were measured by calipers twice a week for calculation of tumor volumes ($\pi \times length \times width^2/6$).

Cell culture. TRAMP-C1 cell line was obtained from ATCC and authenticated using Short Tandem Repeat (STR) profiling method. The cells were maintained in Dulbecco's modified Eagle's medium supplemented with 0.005 mg/ml bovine insulin, 10 nM dehydroisoandrosterone, 5% fetal bovine serum and 5%; Nu-Serum IV.

Tissue examination and tumor grading. At the time of euthanization, the lower genitourinary tract, including the bladder (emptied), seminal vesicles, and the prostate was removed and weighed. Periaortic lymph nodes, lungs and livers were removed and inspected for evidence of visible metastases. Tissues were fixed in 10% phosphate-buffered formalin, embedded in paraffin, and sectioned at 5 μm thickness. The H&E-stained dorsal-lateral lobe sections were each blindly scored on a scale of 1-6 (with '1' representing normal prostate and '6' representing poorly differentiated prostate adenocarcinomas or neuroendocrine tumors) (Gingrich, 1999; Kaplan-Lefko, 2003; Hurwitz, 2001).

Human samples. Tumor specimens were obtained from the Comprehensive Cancer Center at the University of Michigan with informed consent from all subjects in accordance with the Institutional Review Board of the University of Michigan. Two prostate tissue microarrays composed of 62 normal prostate tissues, 10 benign prostatic hyperplasia (BPH), 10 prostate atrophy or prostate inflammatory atrophy (PIA), 10 prostatic intraepithelial neoplasia (PIN), 72 prostate tumors and 10 distant metastases were used in our clinical study. At the time of surgery, the ages of the patients with available information were 56 to 90 years (median=76 yrs, SD=7.6 yrs). All the patients were not treatment with hormone or radiation therapy.

Statistical analysis. All results wherever necessary were subjected to statistical analysis. A log-rank test, a non-parametric Mann-Whitney test, Chi-square test, and unpaired, two-sided, independent Student's t-test with equal variance assumption were used for most studies as indicated in figure legends. For all statistics test, *$P<0.05$,  $P<0.01$, * $P<0.001$.

Results

Figure 12A:
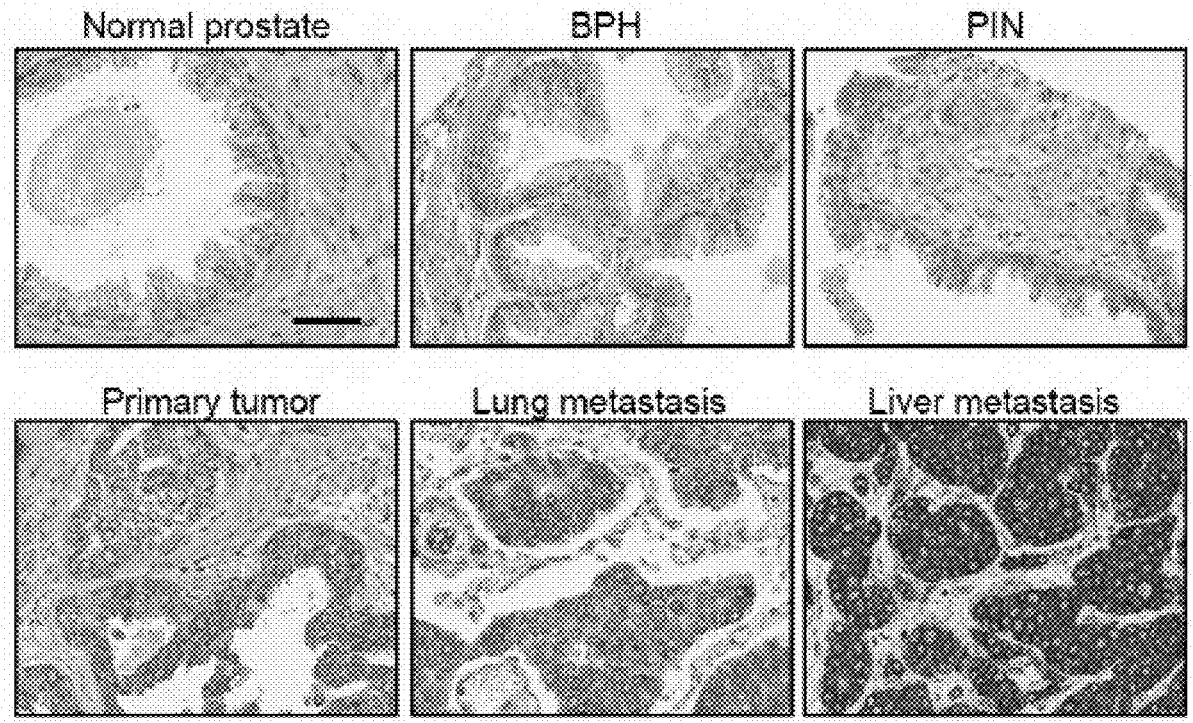
FIGS. 12A-D shows MTDH levels are associated with tumor progression and metastasis in human prostate cancer.
Figure 12B:
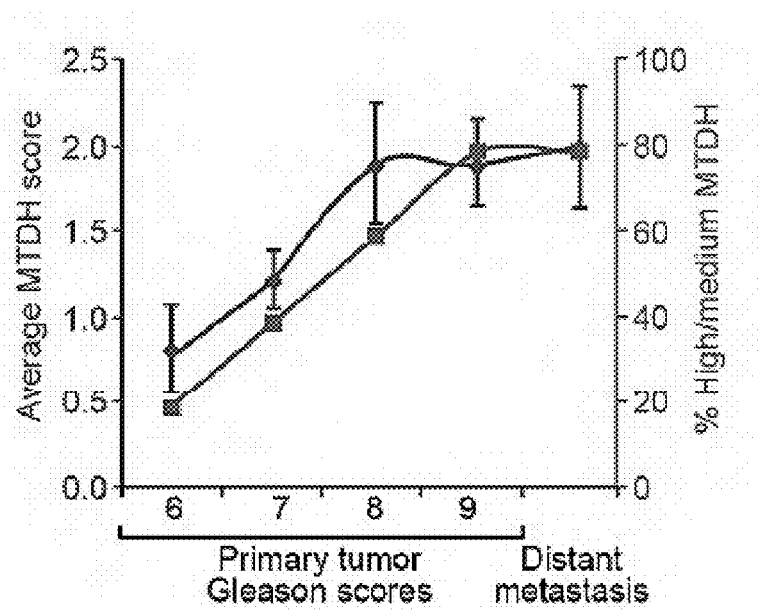
Figure 12C:
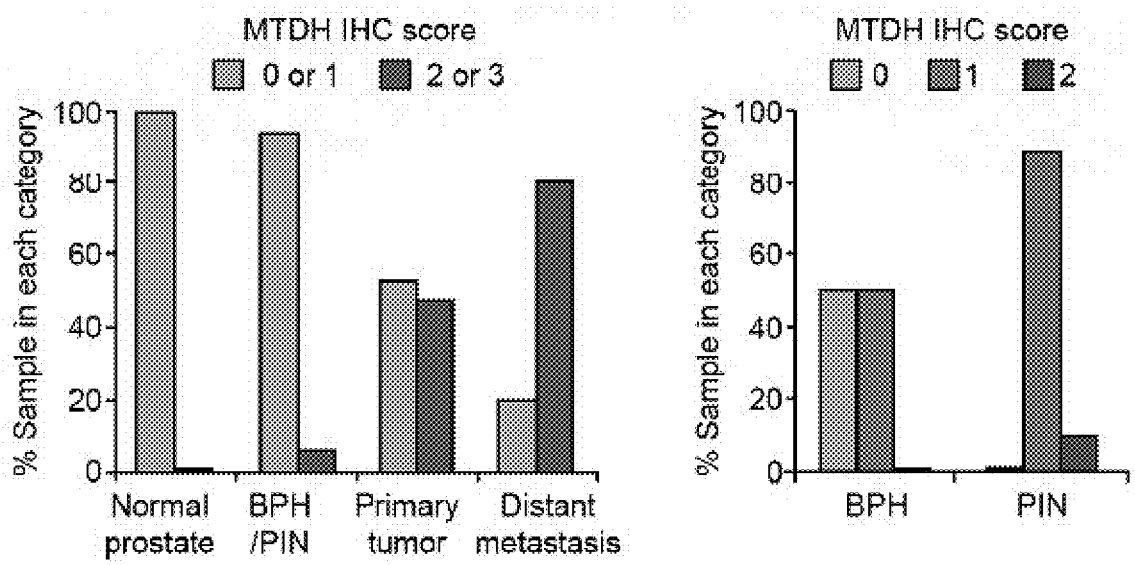
Figure 12D:
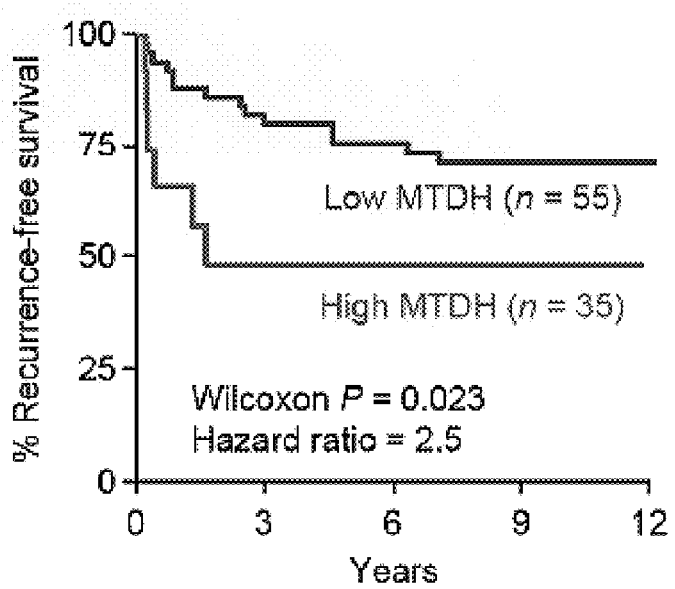

MTDH is associated with tumor progression and metastasis in human prostate cancer: Initially, the clinical relevance of MTDH in human prostate cancer samples was investigated. Two prostate tissue microarrays, consisting samples of normal prostates (NP), benign prostatic hyperplasia (BPH), prostatic intraepithelial neoplasia (PIN), prostate primary tumors and distant metastasis were analyzed by immunohistochemistry, and the MTDH protein levels were compared between samples of different clinical stages (FIG. 12A). MTDH protein was undetectable or expressed at very low levels in all normal or BPH prostate tissues. The protein levels of MTDH gradually increased in premalignant tissues (PIN), primary tumors and metastasis, with the percentages of samples expressing medium or high amount of MTDH as 10%, 47.2% and 80.0%, respectively, revealing a tight correlation of MTDH levels with clinical progression of prostate disease (FIG. 12C, left panel, $X^2$ test $P<0.001$). A difference in MTDH protein levels was already apparent when we compared BPH and PIN, two types of non-cancerous tissues (FIG. 12C, right panel, $X^2$ test $P=0.023$), indicating an increase of MTDH expression during the transition from benign to premalignant stage. MTDH levels were also correlated with Gleason scores of primary tumors, as evidenced by higher average staining intensity of MTDH (FIG. 12B, top curve) or a greater percentage of samples with at least medium levels of MTDH (FIG. 12B, bottom curve) in late-stage tumors. Importantly, the Prostate-Specific Antigen (PSA)-based recurrence rate in patients with medium or high levels of MTDH was significantly higher than that in patients with low levels of MTDH in their prostate tumors (FIG. 12D). Together with the fact that MTDH protein levels in prostate cancer distant metastasis are markedly higher than those in primary tumors (FIGS. 12A and 12B), these data document a strong positive correlation of MTDH levels with prostate cancer recurrence and metastasis.

Figure 13A:
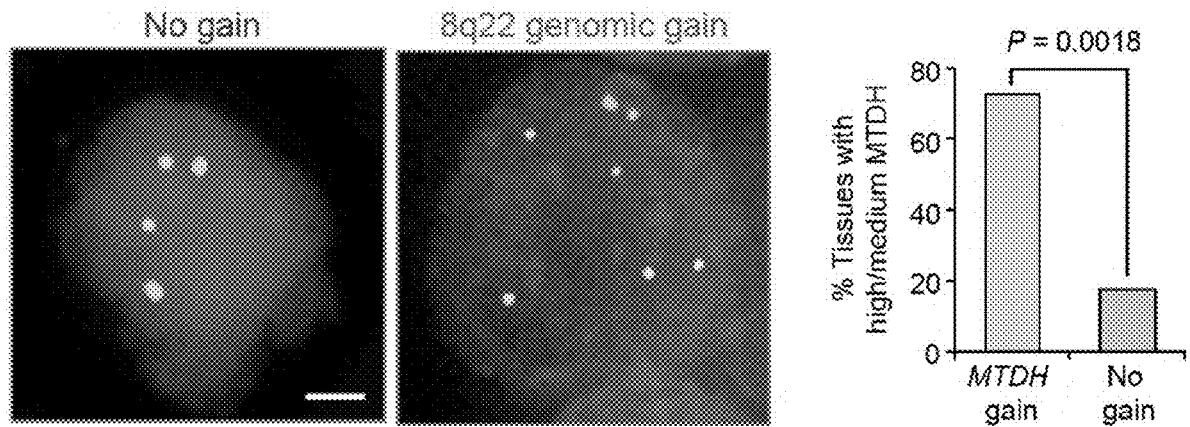
(FIG. 13A), A prostate tumor tissue microarray was analyzed for MTDH genomic copy number by FISH. Shown are examples of tumors without (left) or with (right) MTDH genomic gains. SpectrumGreen (green) and SpectrumOrange (pale orange) probes detect chromosome 8 centromere and the 8q22 region, respectively. Scale bar, 1 µm.
Figure 13B:
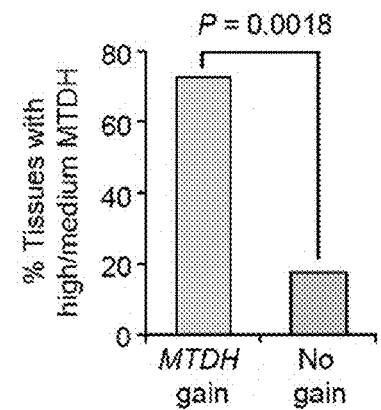
(FIG. 13B), MTDH genomic gain is correlated with MTDH protein levels. Samples with MTDH gain, n=11; samples without MTDH gain, n=64. P=0.0018 by Chi-square test.
Figure 13C:
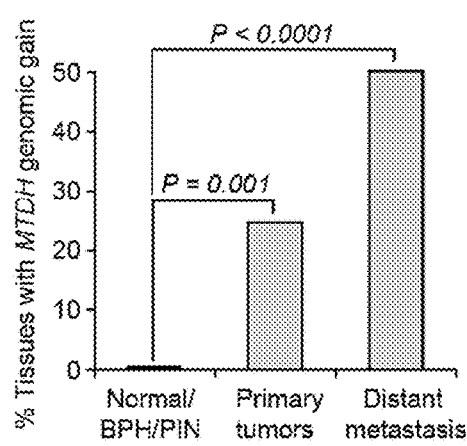
(FIG. 13C), Frequency of MTDH genomic gain in prostate non-cancerous tissues or tumors. normal/benign/ premalignant, n=38; primary tumors, n=29; distant metastasis, n=8. P values by Chi-square test are shown.
Figure 13D:
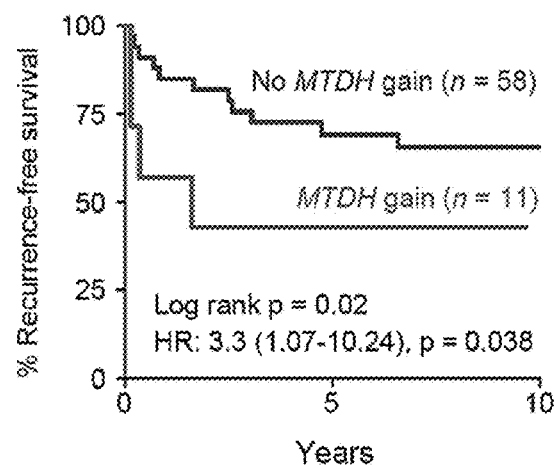
(FIG. 13D), Kaplan-Meier analysis of recurrence-free survival of prostate cancer patients with and without MTDH genomic gain in their tumors. Cox proportional hazard ratio (HR) is shown.

MTDH genomic gain is associated with MTDH overexpression and clinical progression in prostate cancer. To test whether there is also increased genomic copy number of MTDH in prostate tumors, a prostate tissue microarray was analyzed by interphase fluorescent in situ hybridization (FISH) using probes against either the MTDH genomic locus or the chromosome 8 centromere region (as control). FISH analysis revealed a significant portion of prostate cancer samples harbored extra genomic copies of the MTDH gene (FIG. 13A). MTDH DNA gain was significantly associated with higher levels of protein in the cells (FIG. 13B), indicating that DNA gain is a mechanism for MTDH overexpression in prostate cancer. Furthermore, MTDH DNA gain was tightly correlated with clinical stages and prognosis, such that samples before or at the premalignant stages (normal, BPH or PIN), local tumors and distant metastasis, the portions with DNA gain were 0%, 24% and 50%, respectively (FIG. 13C). In addition, patients with increased MTDH copies suffered from earlier recurrence than those without MTDH genomic gain (FIG. 13D). These clinical data demonstrate the prognosis values of DNA and protein status of MTDH, and suggest a potentially important role of MTDH in prostate cancer progression and metastasis.

Generation and characterization of Mtdh-deleted TRAMP mice: To investigate the roles of Mtdh in normal development and cancer, whole-organism Mtdh-knockout (KO) mice were created using ESC line XB780 from Bay Genomics gene trap database (Stryke et al., 2003). The mutant allele contains a LacZ transgene insertion into the second intron of Mtdh, which results in premature termination of transcription. Mtdh-KO (Mtdh-/-) mice were viable and fertile, and no overt abnormality in any organs were seen at autopsy. Specifically, the gross morphology and relative weights of the lower genitourinary tract that includes both the prostate and seminal vesicles were comparable between wild-type (WT, Mtdh+/+), heterozygous (Mtdh+/-) and Mtdh-/- male mice. When examined at microscopic levels, there was no morphological abnormality in the prostate epithelium of Mtdh-/- mice.

Figure 14A:
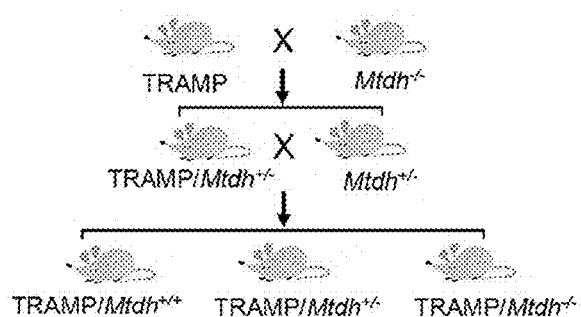
FIGS. 14A-F shows generation and characterization of TRAMP mice with different Mtdh status.
Figure 14B:
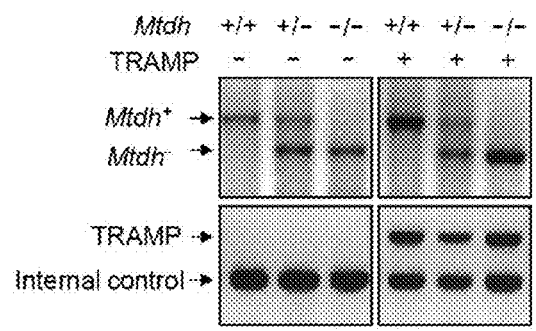
Figure 14C:
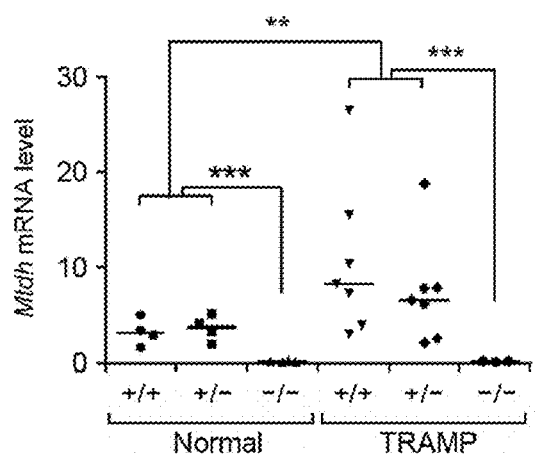
Figure 14D:
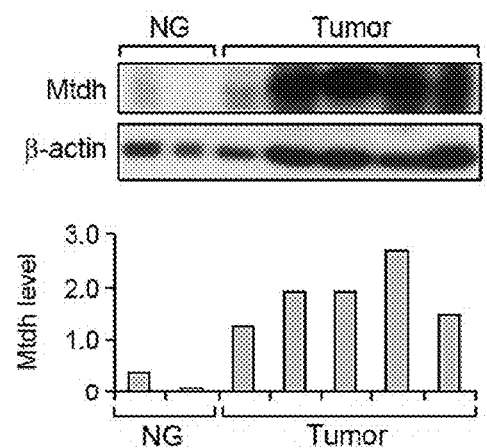

To examine the consequence of Mtdh ablation in prostate tumor formation, the transgenic adenomcarcnoma of mouse prostate (TRAMP) model was used. TRAMP/Mtdh+/+, TRAMP/Mtdh+/-, and TRAMP/Mtdh-/- mice in C57BL/6 background were generated as described in Materials and Methods (FIG. 14A) and the genotypes were confirmed by PCR (FIG. 14B). As an initial step to assess the role of Mtdh in prostate tumorigenesis, we isolated prostate tissues from normal and TRAMP mice and examined the mRNA (FIG. 14C) and protein (FIG. 14D) levels of Mtdh. As expected, no Mtdh mRNA was detected in Mtdh-/- prostate tissues (FIG. 14C), confirming that the gene-trapped method completely abolished Mtdh expression. More abundant Mtdh mRNA was observed in prostate tissues from TRAMP/Mtdh+/+ and TRAMP/Mtdh+/− mice compared to matched control mice that do not express SV40 T antigen (FIG. 14C). Consistently, a significant increase in protein levels of Mtdh was detected in TRAMP/Mtdh+/+ prostates compared to normal controls (FIG. 14D). These data indicate that Mtdh is upregulated during prostate tumorigenesis in mice and suggest that higher levels of Mtdh may confer a competitive advantage for tumor cells.

Figure 14E:
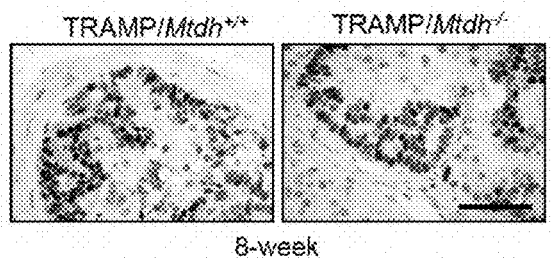
Figure 14F:
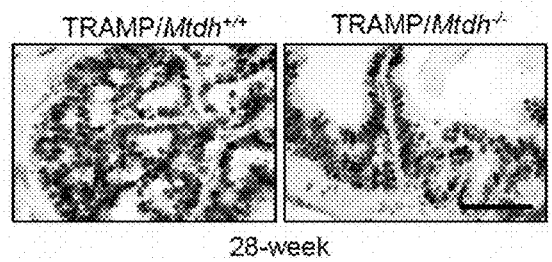

To test whether Mtdh loss affects the expression of the PB-Tag transgene, SV40 T antigen was immunostained in prostates from TRAMP mice. The T antigen was detected in prostatic epithelial cells as early as 8 weeks of age (FIG. 14E) and continuously expressed in the prostatic epithelium and tumor cells at later stages (FIG. 14F). There was no noticeable difference in the T antigen immunoreactivity in individual prostatic epithelial cells between TRAMP/Mtdh+/+ and TRAMP/Mtdh−/− mice at either early or late stages of cancer progression. SV40 t and T mRNA expression were comparable in TRAMP mice with different Mtdh status. As expected for the negative control, SV40 antigens were undetectable in prostates from normal mice. These results demonstrate that Mtdh deletion does not affect the PB-Tag transgene expression in prostate epithelial cells.

Figure 15A:
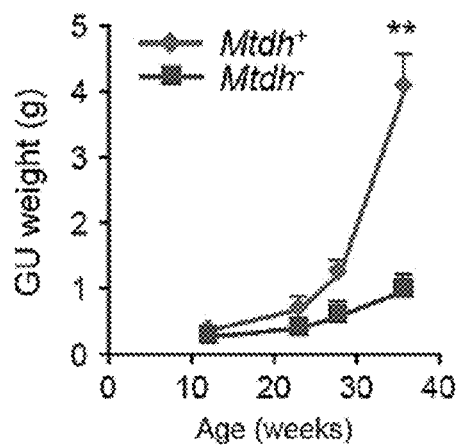
FIGS. 15A-E shows loss of Mtdh in mice inhibits tumor formation, reduces tumor burden and increases survival rate.
Figure 15B:
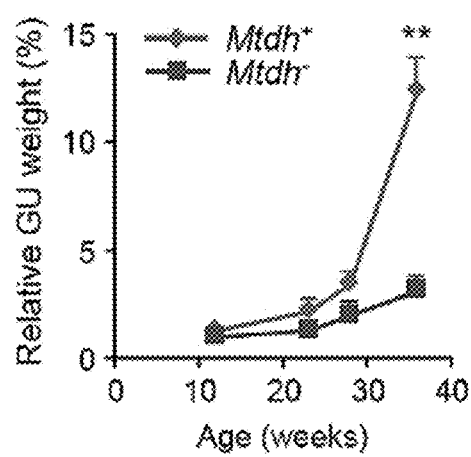
Figure 15C:
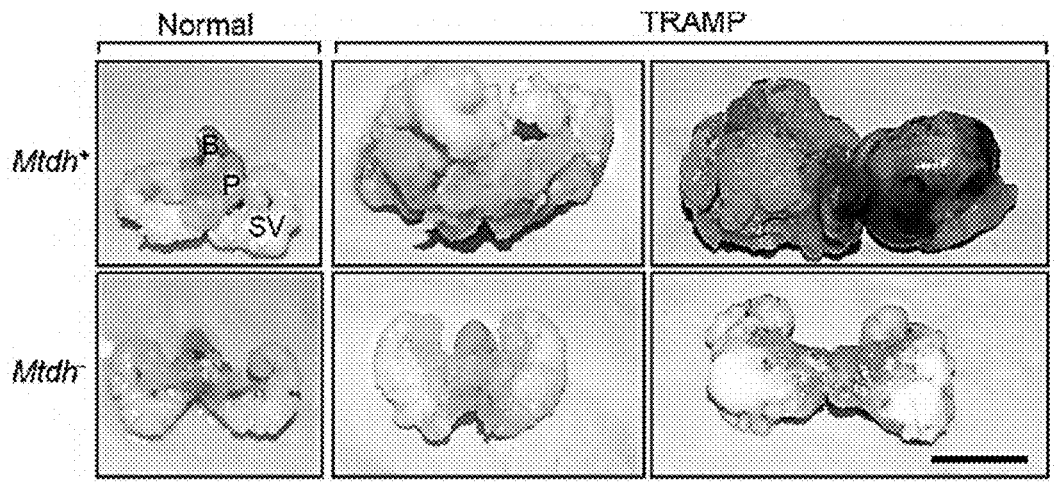

Loss of Mtdh suppresses prostate tumor formation and increases survival rate: To investigate the overall effect of Mtdh on oncogene-induced prostate tumorigenesis, cohorts of TRAMP mice (n>100) with different Mtdh status were studied for their prostate tumor development and cancer-related mortality. First, as genitourinary weight is a reliable indicator of tumor burden in TRAMP mice (Kaplan-Lefko et al., 2003), the urogenital apparatus from TRAMP mice at different ages was dissected and measured to monitor tumor formation at a gross level. Since Mtdh expression was comparable between Mtdh+/+ and Mtdh+/− prostate tissues (FIG. 14C), these mice were grouped as Mtdh-positive group (Mtdh+) versus Mtdh− negative group (Mtdh-). The SV40 T antigens induced a drastic expansion of the urogenital mass in TRAMP/Mtdh+ mice as a function of age (FIG. 15A, diamond), such that many of these mice displayed severely enlarged abdomen at 36 weeks of age. In contrast, the wet weights of genitourinary in TRAMP/Mtdh−/− mice remained relatively constant or increased only at a much slower rate (FIG. 15A, square). Similar results were obtained when the relative genitourinary weight (as % of body weight) was compared (FIG. 15B). Consistently, almost all the urogenital complex dissected from 36-week-old TRAMP/Mtdh+ mice exhibited grossly visible signs of tumor formation (FIG. 15C, top panels), whereas those of TRAMP/Mtdh−/− mice remained similar to normal controls (FIG. 15C, bottom panels).

Figure 15D:
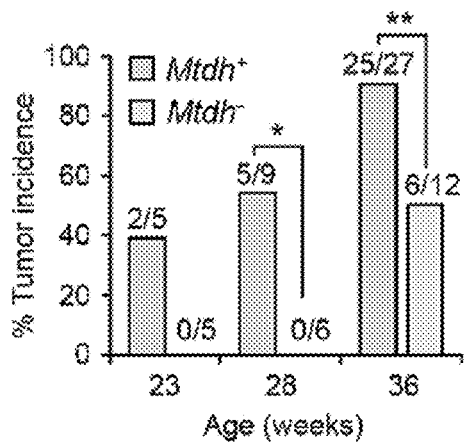

To further assess the occurrence of prostate cancer at histological level, prostate tissues from TRAMP mice were sectioned and hematoxylin and eosin staining was done. About 50% of 23 or 28-week-old TRAMP/Mtdh+ mice developed prostate cancer lesions, and by 36 weeks of age, almost all the mice in this group developed multifocal prostate tumors (FIG. 15D). In contrast, no prostate cancer was detected in 28-week-old TRAMP/Mtdh−/− mice, and prostate cancer lesions were detected in only 50% of 36-week-old TRAMP/Mtdh−/− mice at very limited regions of the prostate epithelium. These histopathologic results are consistent with the morphologic observations showing that most TRAMP/Mtdh−/− mice did not display visible signs for prostate tumor formations by 36 weeks of age (FIG. 15C). Of note, tumors formed in TRAMP mice exhibit diverse histological features that are characteristic of adenocarcinomas, phyllode-like tumors, and neuroendocrine tumors, and it has been suggested that these morphologically distinct tumors may originate from different cell lineages within the prostate or develop independently from common early progenitors (Chiaverotti et al., 2008). Interestingly, TRAMP/Mtdh−/− mice showed a delay in the occurrence of all these different tumor subtypes, often appearing around 28 or 36 weeks, suggesting a possible lineage-independent role of Mtdh in prostate cancer.

Figure 15E:
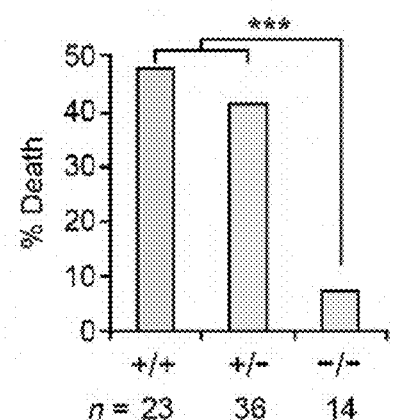

As a consequence of malignant prostate cancer development, a significant percentage (~50%) of TRAMP/Mtdh+ died before reaching one year of age. In contrast, only 1 out of 14 TRAMP/Mtdh−/− examined died from cancer-related disease (FIG. 15E, P<0.001). These data together demonstrate that Mtdh deletion in mice inhibits oncogene-driven formation of prostate cancer and extends the life span of TRAMP mice.

Figure 16A:
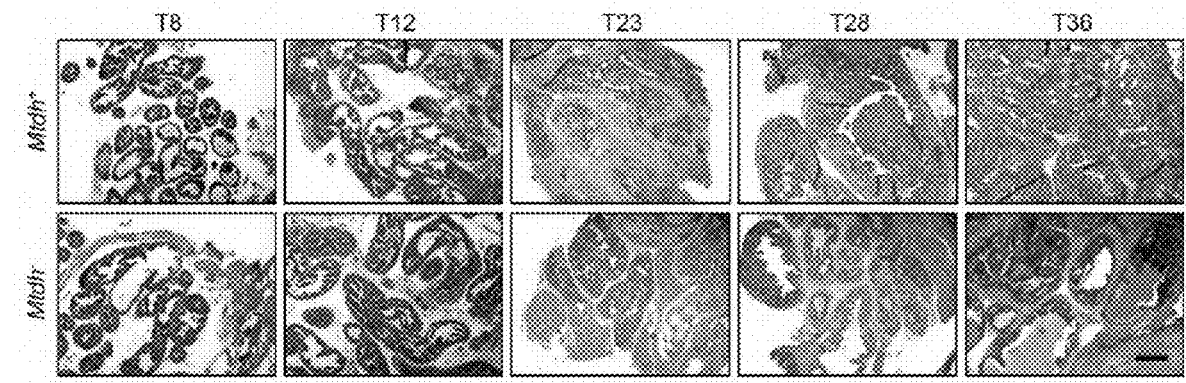
FIGS. 16A-C shows loss of Mtdh inhibits malignant progression of prostate cancer.
Figure 16B:
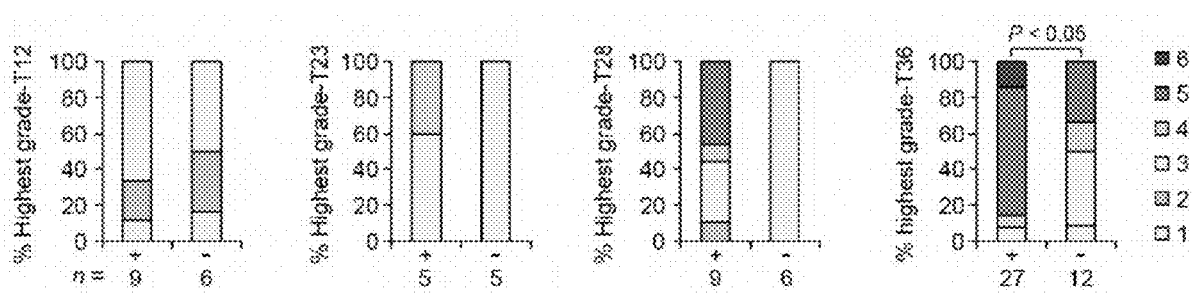
Figure 16C:
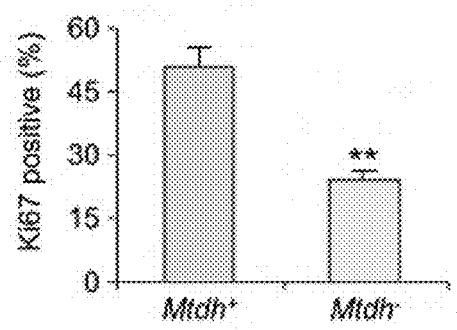

Inactivation of Mtdh impedes prostate cancer progression: Prostate cancer progression consists of multiple stages starting from premalignant lesions such as PIN to well, moderately, and poorly differentiated carcinoma. To investigate how Mtdh loss affects the initiation and progression of prostate cancer, histological examination was performed on dorsal and lateral lobes of each prostate gland, the most frequent and severe sites subjected to tumorigenesis in TRAMP mice (21) (FIG. 16A). Based on previously described grading systems for TRAMP tumors (21, 22), each prostate was assigned a highest score ranging from a score of 1 for normal prostate and 6 for poorly differentiated carcinoma including neuroendocrine tumors. PIN lesions were readily detected in both TRAMP/Mtdh+ and TRAMP/Mtdh− prostates from 8 to 12 weeks of age (FIG. 16B, first panel), as evidenced by epithelial hyperplasia and the presence of an intact basal cell layer (FIG. 16A, T8 and T12). This was consistent with comparable proliferation and apoptosis indices in prostate epithelium from 10-week-old TRAMP/Mtdh+ and TRAMP/Mtdh− mice. A substantial fraction of TRAMP/Mtdh+ mice developed well or moderately differentiated adenocarcinoma with invasive lesions at 23 weeks and 28 weeks, respectively, and by 36 weeks, 84% of TRAMP/Mtdh+ mice displayed moderately to poorly differentiated adenocarcinoma characteristic of analplastic sheets of tumor cells. In comparison, the majority of TRAMP/Mtdh− mice only developed PIN or early-stage, well-differentiated adenocarcinomas or phyllode-like tumors by 36 weeks. Consistently, the expression of E-cadherin was gradually reduced or even became absent as prostate tumors progressed to less-differentiated stages in TRAMP/Mtdh+ mice, whereas abundant E-cadherin was detected in prostate tissues in TRAMP/Mtdh−/− mice across different ages examined. In addition, malignant progression of Mtdh+ tumors was accompanied by a significantly higher percentage of proliferating cells (FIG. 16C, P<0.01), whereas the percentage of apoptotic cells were similar in Mtdh+ and Mtdh− tumors at this stage. Taken together, these findings suggest that inactivation of Mtdh arrests prostate cancer progression at early stages of tumorigenesis and prevents premalignant lesions to expand and progress into advanced stages.

Ablation of Mtdh reduces systemic metastasis of prostate tumor cells: Metastatic disease in cohorts of TRAMP mice were examined at around 50 weeks of age, a time point when most of TRAMP/Mtdh−/− mice have developed prostate cancer lesions. Livers, lungs and periaortic lymph nodes, frequent sites of metastasis in the TRAMP model (Gingrich et al., 1996), were dissected and examined the appearance of metastatic lesions (FIG. 17A-B) at both macroscopic and histology levels. Multiple large metastatic nodules were observed in livers from 34% of TRAMP/Mtdh+ mice, resulting in markedly increased liver size. Conversely, none of TRAMP/Mtdh−/− mice examined developed visible metastases in the liver. Similarly, multiple metastatic deposits in the lung were found in 39% of TRAMP/Mtdh+ mice, but only 2 out of 17 TRAMP/Mtdh−/− mice had one or two metastatic lesions detected in their lungs. Enlargement of lymph node were frequently identified in TRAMP/Mtdh+ mice (9/20) and this incidence decreased to 30% in TRAMP/Mtdh−/− mice. To demonstrate that the metastatic cells were of prostatic origin, immunohistochemical analysis was performed on serial sections of the liver, lung and lymph node to detect the T antigen oncoprotein. A uniform expression of the T antigen oncoprotein was observed confined to the metastatic deposits but not surrounding normal cells, in agreement with the tissue-specific pattern of PB-directed transgene expression (Gingrich et al., 1996). These data together clearly show that Mtdh deletion in mice significantly reduced systematic metastasis in the TRAMP model. Of note, due to the fact that close to 50% of TRAMP/Mtdh+ mice had died from large primary and likely metastatic tumors before reaching one year of age, the observed difference in metastasis between Mtdh+ and Mtdh− groups was very likely to be underestimated.

Figure 18A:
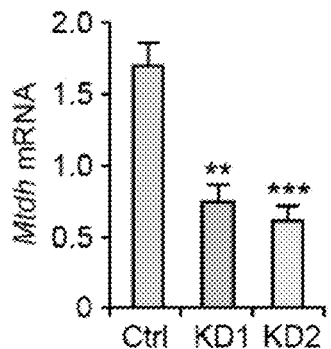
FIGS. 18A-G shows silencing of Mtdh in TRAMP-C1 prostate cancer cells decreases proliferation in vitro and tumor formation in vivo.
Figure 18B:
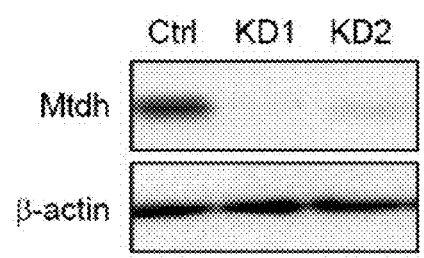
Figure 18C:
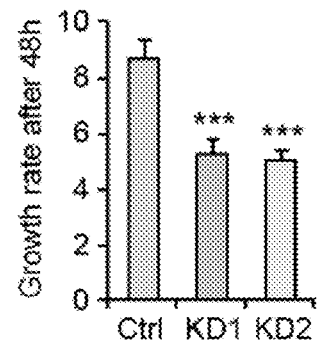
Figure 18D:
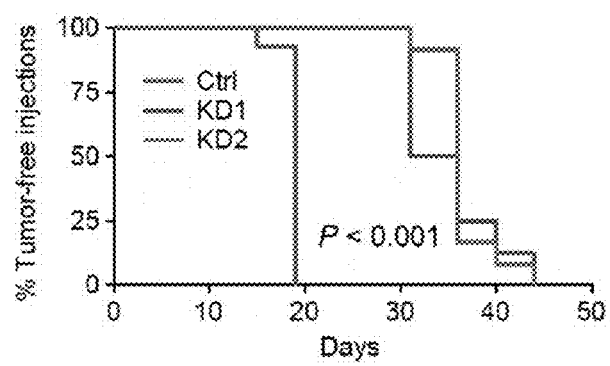
Figure 18E:
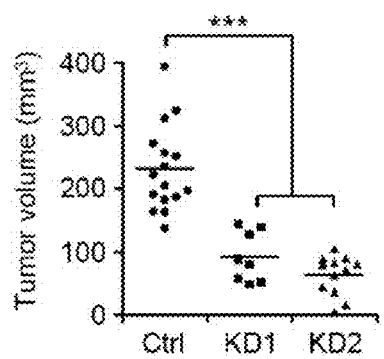
Figure 18F:
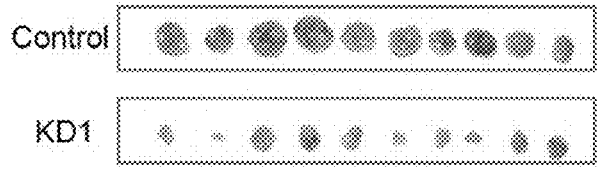
Figure 18G:
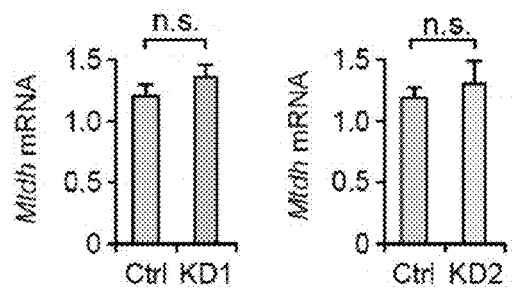

Knockdown of Mtdh in prostate cancer cells reduces proliferation in vitro and tumor formation in vivo: As Mtdh is widely expressed in mice, the tumorigenesis defects in whole-organism Mtdh-KO mice could result from either loss of Mtdh in prostate epithelial cells or other cell/tissue types. To distinguish between these two possibilities, the necessity of Mtdh in tumorigenic ability of TRAMP-C1 cell line was examined, which is characteristic of an advanced prostate tumor in the TRAMP model (Foster, 1997). Mtdh was knocked down (KD) (FIGS. 15A and 9B) and found that Mtdh-KD decreased proliferation of TRAMP-C1 cells in vitro (FIG. 15C). To examine the consequence of Mtdh-KD in tumor formation in vivo, we injected control and Mtdh-KD cells into the flanks of recipient mice and monitored tumor occurrence over time. The occurrence of palpable tumors was significantly delayed in the KD groups (FIG. 18D), and tumors dissected from the KD groups were much smaller than those from the control group (FIGS. 18E and 18F). Similar results were obtained in another two independent of experiments. Interestingly, tumors that eventually formed in the Mtdh-KD groups expressed similar levels of Mtdh as tumors in the control group (FIG. 18G), which could result from either the clonal expansion of the cells without Mtdh inhibition or from re-expression of Mtdh in Mtdh-KD cells.

Discussion

Human prostate cancer is characterized by rampant recurrent amplifications and deletions, suggesting that along with a few well known genetic lesions, such as loss of tumor suppressors PTEN and p53, there remain many uncharacterized genes governing the genesis and progression of this malignancy (Taylor, 2010). In current study, it was demonstrated that MTDH is frequently overexpressed and amplified in human prostate cancers and its expression levels strongly correlate with disease progression and poor survival outcome. In addition, the genetic studies utilizing Mtdh-KO mice provide the first in vivo evidence that Mtdh plays a critical role in spontaneous prostate cancer progression and metastasis without affecting normal development.

The TRAMP model closely resembles human prostate cancer as it spontaneously develops progressive prostate cancer that can metastasize to multiple different organs. Importantly, it was shown here that Mtdh levels are elevated in both human and SV40-driven murine prostate tumors compared to normal prostate tissues. Interestingly, Mtdh was recently shown to be overexpressed through genomic amplification in a p53/Pten-deficient metastatic prostate cancer mouse model in which telomerase activity was reactivated following telomere dysfunction (Ding, 2012), suggesting that Mtdh can be activated in mice through genomic amplification mechanism similar to what we found in human prostate cancer. Future studies are needed to investigate the molecular basis of Mtdh overexpresison in SV40-transformed tumors.

It was shown that Mtdh knockout in the TRAMP mice significantly impaired tumor formation and decreased cancer-related mortality. The findings that silencing of Mtdh in TRAMP-C1 cancer cells prolonged tumor free-survival and reduced tumor growth in vivo lend further support for a prostate tumor cell-intrinsic role of Mtdh in prostate cancer. Of note, tumors eventually formed by TRAMP-C1 cancer cells that presumably carried Mtdh-targeting shRNA regained the expression of Mtdh, reinforcing the notion that Mtdh is essential for prostate cancer formation in vivo. A blockage of prostate cancer progression was observed at benign or well-differentiated stages in TRAMP/Mtdh−/− mice, a notion that is further supported by constitutively high levels of epithelial marker E-cadherin in TRAMP/Mtdh−/− prostate tissues. Consistently, while TRAMP/Mtdh+ mice displayed enlarged prostate glands and obstructed seminal vesicles, a phenomenon often resulted from invasive and malignant growth of prostate tumor cells into the urethra and seminal vesicles, urogenital track from TRAMP/Mtdh−/− mice appeared largely normal. In line with the findings from mouse models, MTDH exhibits a progression-correlated expression pattern in human prostate cancer. These results may suggest the potential use of MTDH as a biomarker for prostate cancer progression and a possible therapeutic target to halt malignant progression of human prostate cancer.

The fact that a small percentage of TRAMP/Mtdh−/− mice still developed invasive prostate cancer after long latency and died from the disease (1 out of 14) suggests that some TRAMP/Mtdh−/− tumors have overcome the deficiency of Mtdh and utilized Mtdh-independent pathways to support their malignant growth and progression. Indeed, the induction of SV40 oncogene occurs uniformly in prostate epithelial cells as early as puberty; however, the development of invasive prostate cancer and metastasis occurs much later and appears to be highly heterogeneous, suggesting that individual tumor may acquire different genetic and epigenetic alterations to fully transform SV40 antigen-positive cells. While inactivation of Mtdh inhibits Mtdh-dependent signaling and prostate cancer progression as observed in the majority of TRAMP/Mtdh−/− mice, it would not block tumor growth that is supported by Mtdh-independent mechanisms. This is also in line with the observation that MTDH is highly expressed in a large percentage but not all human prostate cancer. Nevertheless, cancer cells that have depended on high levels of MTDH for their progression to a malignant stage would be sensitive to MTDH-targeting therapeutics, as supported by the finding that inhibition of Mtdh in Mtdh-positive TRAMP-C1 cells significantly impairs the tumorigenic potential of these cells.

Metastasis to distant organs is responsible for the majority of cancer-related death in patients with solid cancer (Wan, 2013). It was previously demonstrated that MTDH is amplified and/or overexpressed in human breast cancer with a higher risk of metastasis (Hu et al., 2009). In the current study, it was found that a substantial fraction of distant metastases of human prostate cancer exhibited high levels of MTDH and harbored amplification of the 8q22 genomic loci. Functionally, Mtdh ablation significantly decreased the incidence and burden of metastases in distant organs in the TRAMP model. In concordance with these findings, a recent study shows that telomerase reactivation following telomere dysfunction in a prostate-cancer prone mouse model driven by Pten and p53 loss facilitates the selection of copy number alterations at cancer-relevant loci, and Mtdh was found to be at the top of a selective list of genes whose genetic amplification is strongly associated with cancer progression and metastasis in this mouse model (Ding et al., 2012). This suggests a possibly important role of Mtdh in prostate cancer driven by genetic events in addition to SV40 oncogenes. Finally, it should be noted that the metastasis-promoting function of MTDH is likely to exist in other cancer types, beyond breast and prostate cancers. Several recent studies indeed showed abnormal MTDH expression was associated with lymph node metastasis and a worse prognosis in additional cancer types including laryngeal squamous cell carcinoma (Liu et al., 2013), squamous cell carcinoma of the head and neck (Yu et al., 2014), and hepatocellular carcinoma (Zhu et al., 2011), and overexpression of MTDH increases experimental metastasis of hepatocellular carcinoma cells (Yoo et al., 2009).

In summary, the study herein reports that MTDH is overexpressed in both mouse and human prostate cancer and this elevated level of MTDH is critical for spontaneous prostate cancer progression and metastasis in vivo. Given the broad overexpression of MTDH in diverse cancer types, the tumor-promoting roles of MTDH may not be restricted to the models used in the study. Indeed, ongoing studies have also found that deletion of Mtdh drastically inhibits spontaneous mammary tumor formation and metastasis. Future studies are needed to understand the underlying mechanisms and signaling pathways that responsible for the tumor-promoting function of MTDH and to facilitate the development of MTDH-targeting therapeutics to control human cancer.

Example 3—Analysis of the Interactions Between Metadherin and SDN1

Metadherin (MTDH) and Staphylococcal nuclease domain containing 1 (SND1) are overexpressed and interact in diverse cancer types. Both MTDH and SND1 interact with diverse cellular machineries and signaling proteins and are implicated in multiple cancer-related cellular processes and signaling pathways, it is possible that MTDH and SND1 enhance malignant features by coordinating tumor-promoting signaling activities via their multiple interaction domains/motifs. The complete lack of structural information, however, greatly hinders mechanistic understanding of the function of the MTDH/SND1 protein complex despite the significant clinical relevance of both proteins in many types of cancer. Elucidating the structural basis of MTDH-SND1 interaction is also important for developing new ways of targeting MTDH or SND1 as a novel cancer therapeutic strategy. In order to analyze the interaction between the two proteins, the high-resolution crystal structure of MTDH-SND1 complex was determined as set out below, which reveals an 11-residue MTDH peptide motif occupies an extended protein groove between two SN domains (SN1/2), with two MTDH tryptophan residues nestled into two well-defined pockets in SND1.

Experimental Procedures

Protein Preparation: All constructs and point mutations were generated using a standard PCR-based cloning strategy. Briefly, SND1 and MTDH with different boundaries and mutants were cloned in pQlink vector (Addgene) harboring an N-terminal His8-tag and a GST-tag, respectively, with a TEV cleavage site after the affinity tag. The proteins were overexpressed at 23° C. in E. coli strain DH5a. Expression and purification of SND1 and SND1 (16-339)-L21-MTDH (386-407) followed the procedure modified from previous publication (Li et al., 2008).

For SND1 proteins, the soluble fraction of lysate was purified over Ni-NTA resin (Qiagen) with lysis buffer containing 2 mM β-ME, 0.5 M NaCl, 5 mM immidazole and 25 mM Tris PH8. His-SND1 proteins were eluted by buffer containing 0.2 M NaCl, 250 mM immidazole, and 25 mM Tris PH8 without β-ME. After dilute 4-fold by Heparin buffer A (25 mM HEPES, PH7, 10 mM EDTA, 10% glycerol, 2 mM β-ME), proteins were loaded to Heparin column (GE Healthcare) and eluted by 100 ml of 0-0.6 M NaCl gradient. The GST-tagged MTDH proteins were purified over GS4B resin (GE Healthcare) and further fractionated by anion exchange chromatography (Source 15Q, GE Healthcare).

To facilitate crystallization of SND1 and MTDH complex, SND1 (16-339) was fused to the MTDH peptide (386-407) via a flexible linker with 21 residues (L21). For SeMet protein, 12L of His-SND1(16-339)-L21-MTDH (386-407) fusion protein were overexpressed in pQlink vector at 23° C. in E. coli strain (BL21, DE3) for 22 hours at OD600=1.0 with 0.25 mM IPTG. The protein was purified by Ni-NTA and Heparin column as described above before cleaved by TEV protease in the presence of 10 mM DTT. The sample was adjust to 1.4 M (NH4)2SO4 and spun to remove pellet before further purified by Hydrophobic Interaction Chromatography (HiTrap Phenyl HP, GE Healthcare) to remove impurities, including TEV and the dimer of fusion protein at later peak. The monomer of fusion protein was then purified by gel filtration chromatography (Superdex 200, GE Healthcare) at final step to change the buffer to 10 mM Tris PH8, 150 mM NaCl and 10 mM DTT. The sample was concentrated to 15 mg/ml for crystallization.

Crystallization and Data Collection: Crystals of SND1 and MTDH fusion protein were grown at 23° C. by the sitting-drop vapor-diffusion method by mixing 250 nl of 15 mg/ml SeMet-SND1(16-339)-L21-MTDH (386-407) with 250 nl of well buffer (21.6% pEG3350, 0.1M Sodium Citrate, PH8.0, 0.1M CsCl), plus 50 nl of micro seeds. Single crystals grew in 4 days and matured after 7 days. Crystals were gradually changed to well buffer with 0 to 25% glycerol before flash frozen in liquid nitrogen. To reduce the radiation damage to the crystals, two SAD datasets for SND1(16-339)-L21-MTDH (386-407) were collected continuously on the same position with 25% beam energy, 0.6 second/frame at wavelength 0.97849 Å. Data were collected at APS LS-CAT (ID-D) and these two datasets were combined and processed to 3.0 Å using HKL2000 (Otwinowski, 1997). The optimistic cutoff of anomalous scattering signal was measured at 4.3 Å of 0.0833 by phenix.xtriage (Adams et al., 2010). A second SAD dataset was collect by increasing exposure time to 1.5 S, which was processed to 2.7 Å.

Structure Determination: The initial structure of SND1 (16-339)-L21-MTDH (386-407) was determined by phenix.autosol (Adams et al., 2010) using the combined SAD datasets at 3.0 Å. 24 Selenium atoms and 5 asymmetric units were found in the initial model with Rfree/Rwork=0.35/0.30. This model was refined by phenix.refine (Adams et al., 2010) with anomalous group (Se) and served as starting model for the 2.7 Å dataset by molecular replacement using Phaser (McCoy et al., 2007) in the CCP4 package (Winn et al., 2011). The improved model was manually built using Coot (Emsley and Cowtan, 2004) and refined using phenix.refine restraints with TLS and anomalous group (Se) (Adams et al., 2010). The final structure was refined to 2.7 Å (Table 51).

GST-Mediated Pull-Down Assay: ~20 µg of GST-MTDH (different truncation forms and site mutants) was bound to 10 µl of glutathione resin via GST tag. The resin was washed with 200 µl assay buffer (25 mM Tris, PH8.0, 150 mM NaCl, 3 mM DTT) three times to remove the excess unbound protein. 15 µg of His-SND1 (16-339) was added to the resin in a 100 µl volume suspended in the assay buffer with 2 mg/ml of BSA. The mixture was washed with 200 µl assay buffer twice before examined by SDS-PAGE, and visualized by Coomassie blue staining. The experiments were repeated 3 times and the ratio of SND1 associated with GST-MTDH was analyzed by ImageJ.

Immunoprecipitation and western blot: For in vivo immunoprecipitation (IP) experiments, cultured cells were washed in cold PBS and lysed in lysis buffer (20 mM Tris pH 7.4, 0.15 M NaCl, 1 mM EDTA, 1 mM EGTA, 1% Tx-100, 0.0025 M Na2P2O7, 1 mM β-glycerolphosphate, 1 mM Na3VO4, and 1 mM NaF) with an EDTA-free protease inhibitor mixture (Roche Applied Science) and PMSF. Cell lysates were then incubated on ice for 10 min, centrifuged, and precleared by incubating with protein A/G beads (Santa Cruz Biotechnology) for 1 h at 4° C. For IP bead preparation, 30 µl of protein A/G beads were incubated with 5 µg of antibodies for 2 h at 4° C. IPs were carried out for overnight at 4° C., and beads were centrifuged, washed and subsequently boiled for 5 min in SDS protein loading buffer to elute bound protein. IP lysates were subjected to western blotting with indicated antibodies.

For western blotting, lysates from cultured cells were collected by directly adding lysis buffer on to the plate. Western blot gel preparation and immunoblotting were performed following standard procedures. Antibodies against MTDH (Invitrogen, catalogue #40-6500), SND1 (Santa cruz, catalogue # sc-271590), anti-Myc (Santa Cruz, catalogue # sc-40), and anti-HA (Santa Cruz, catalogue # sc-7392) were diluted 1:1000.

Tumorsphere assays: Single cells were plated in ultra low attachment plates (Corning, Tewksbury, Mass.) with sphere media (1:1 DMEM: Ham's 12 supplemented with B27 (Invitrogen), 20 ng/mL EGF, 20 ng/mL bFGF, and 4 µg/mL heparin). Spheres were counted 4-7 days after plating.

Tumorigenesis assays: All procedures involving mice and all experimental protocols were approved by Institutional Animal Care and Use Committee (IACUC) of Princeton University. For tumorigenesis assays, indicated numbers of PyMT tumor cells were transplanted into mammary fat of FVB recipient mice and tumor formations were monitored twice every week. Tumors were considered established when they became palpable for two consecutive weeks, and tumor size was measured by calipers for calculation of tumor volumes (□×length×width 2/6).

FRET Assay: For FRET assay, CFP-MTDH fusion protein and a tetracysteine peptide fused to (TC) SND1 (16-339) were cloned into pQlink vector (Addgene) harboring an N-terminal GST-tag with a TEV cleavage site after the affinity tag. The proteins were overexpressed at 23° C. in *E. coli* strain DH5a. The soluble fraction of the *E. coli* cell lysate was purified over GS4B resin (Qiagen), followed by TEV cleavage to remove the GST-tag. The untagged proteins were further fractionated by anion exchange chromatography (Source 15Q, GE Healthcare) and gel filtration chromatography (Superdex 200, GE Healthcare).

The FlAsH-EDC2 compound (Invitrogen) was added to TC-SND1 (16-339) at 1:1.1 molar ratio to create the highly fluorescent TC-FLASH-SND1 that serves as the acceptor for CFP in the FRET assay. The donor fluorescent signal of CFP of 0.2 µM CFP-MTDH was measured in the presence and absence of increasing concentrations of TC-FLASH-SND1 (0.25, 0.5, 1, 2, 4, 8 µM) using a Victor X5 Multilabel Plate Reader (Perkin Elmer) with excitation at 450 nm and emission at 490 nm. The rate of energy transfer was calculated based on loss of donor fluorescence using the following equation: $E=1-(FDA/FD)$, where FDA and FD are the fluorescence of CFP in the presence and absence of TC-FLASH-SND1, respectively. The TC-FLASH-SND1 concentration-dependent FRET efficiency was fitted in GraphPad Prism (GraphPad Software, Inc.) for estimating the equilibrium dissociation constant (KD) between the MTDH peptide and SND1. The experiments were repeated three times; representative results are shown.

Biolayer interferometry (BLI): BLI sensors immobilized by anti-GST antibody were activated by incubation with 150 nM GST-MTDH (386-407), followed by incubation with 1 mg/ml BSA and wash by binding buffer containing 25 mM Tris pH 8.0, 100 mM NaCl, and 3 mM DTT, with three minutes each step. Seven sensors activated by GST-MTDH were simultaneously dipped into seven wells containing the binding buffer control and increasing concentrations of His8-SND1 (16-339) (0.1, 0.2, 0.4, 0.8, 1.6, 3.2 µM) to measure the on rate of SND1-binding. After three minutes of binding, the sensors were dipped into binding buffer to measure the off rate. Data collection and analysis were performed using ForteBio Octet RED96 (Pall Life Science).

Statistical analysis: All results wherever necessary were subjected to statistical analysis. A log-rank test, a nonparametric Mann-Whitney test, chi-square test, and unpaired, two-sided, independent Student's t-test with equal variance assumption were used for most studies as indicated in figure legends. For limiting dilution assay, the frequency of TICs and statistics were calculated using L-calc software (StemCell Technologies). P values were denoted as *$p<0.05$ $p<0.01$, *$p<0.001$ in all figures.

Accession Number: The atomic coordinates of the MTDH-SND1 complex were deposited in the Protein Data Bank with accession code 4QMG.

Results

Mapping of the minimal regions of MTDH and SND1 required for their interaction: The primary sequence analysis carried out initially of MTDH (residues 1-582) suggested that MTDH is largely unstructured in its entire sequence except a trans-membrane domain near the N-terminus. Thus, MTDH might function as a scaffold protein and recruit diverse signaling molecules via its peptide motifs throughout its sequence. Building on the previous observation that a MTDH fragment (amino acids 364-470 of SEQ ID NO: 1) harbors the essential region required for interaction with SND1 (Blanco et al., 2011), a minimal fragment of MTDH (amino acids 386-407 of SEQ ID NO: 1) was recently mapped within this region that confers SND1 binding (see above). None of the SND1 domains had been mapped for specific interaction with protein molecules. To fill in this gap, a handful of SND1 constructs were made and two gave highly soluble recombinant proteins that harbor the N-terminal SN1/2 and the C-terminal SN3/4-TSN5 domains, respectively. By performing a pull-down experiment using a GST-tagged MTDH (amino acids 364-582 of SEQ ID NO: 1) fragment that harbors the SND1-binding motif, we showed that the SN1/2 domains (amino acids 16-339 of SEQ ID NO: 2) of SND1 bind stoichiometrically with MTDH, while the SN3/4-TSN5 domains (amino acids 340-885 of SEQ ID NO: 2) barely interact with MTDH. Further analysis of this interaction using biolayer interferometry showed that this interaction was readily reversible. The binding affinity between MTDH and SND1 was around 0.9 μM as indicated by the FRET (fluorescence resonance energy transfer) assay.

Overall structure of the MTDH-SND1 complex: After extensive effort, co-crystallization of the SND1 SN1/2 domains and synthetic peptides harboring MTDH residues 386-407 of SEQ ID NO: 1 failed to yield protein crystals, likely due to the relatively weak interaction between the two proteins. To stabilize the complex and facilitate crystallization, the SND1 SN1/2 domains were fused to MTDH (amino acids 386-407 of SEQ ID NO: 1) via a flexible linker with the length ranged from 12-37 residues. A construct with a 21-residue linker eventually gave diffracting crystals. Although the SN1/2 domains are closely related to the SN3/4 domains, structural determination by molecular replacement using the structure of SN3/4 (PDB code: 3BDL) was not successful, likely due to large diversity of the extended loops emanated from the OB-fold. Finally, the structure was determined by Selenium SAD (single-wavelength anomalous dispersion) phasing, and refined to 2.7 Å.

Figures 17A, 17B:
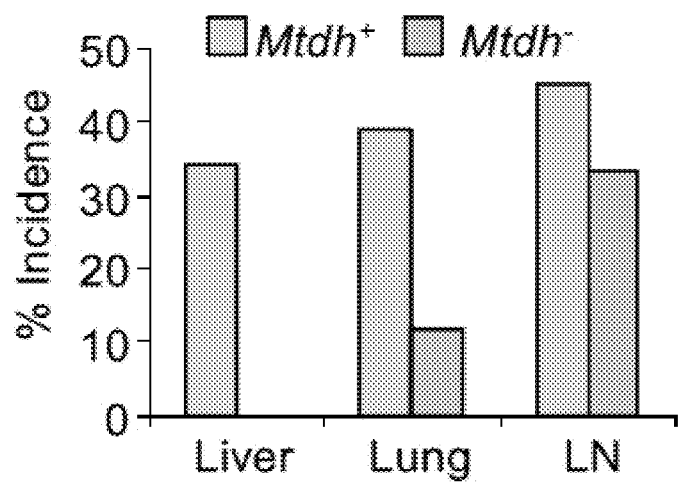
FIGS. 17A-B shows ablation of Mtdh reduces systemic metastasis of prostate cancer.

Five copies of the MTDH-SND1 fusion proteins were found in each asymmetric unit that is almost identical, with the root-mean-square-deviation no more than 0.9 Å over 290 residues. The number of MTDH residues with defined electron density varied slightly in different copies. Nonetheless, residues 393-403 of MTDH were visible in all copies with well-defined electron density map at the interface with SND1. Both SN1 and SN2 exhibit typical OB-fold of Staphylococcal nuclease (SNase) and were arranged in a central symmetry-related fashion (FIG. 16), similar to SN3/4 (FIG. 17A). Each SN domain contains a β-barrel (β1-β2-β3-β7-β5) capped by a three-helix bundle (α1-α2-α3) and a short β-hairpin (β4-β8) (FIG. 16). The MTDH peptide (D393WNAPAEEWGN403 of SEQ ID NO: 1) occupies the shallow groove between SN1 and SN2 domains, with the two tryptophan residues, W394 and W401 of SEQ ID NO: 1, making extensive hydrophobic contacts with two well-defined hydrophobic pockets in SND1.

It is noteworthy that, at the opposite side of the MTDH-SND1 interface, SND1 possesses three extended protruding structural elements (the β6-β7 hairpin in SN1 and the extended Lβ4-α1 loop in both SN1 and SN2), resulting in a spiky surface capable of diverse binding modes. The SN1/2 domains were previously suggested to participate in DNA/RNA-binding, and contribute to the nuclease activity of SND1 (Li et al., 2008). It remains to be determined whether the hilly surface of SND1 opposite to the MTDH-SND1 interface might participate in binding with DNA/RNA or other proteins and contribute to the nuclease activity or signaling mediated by SND1.

Figure 19:
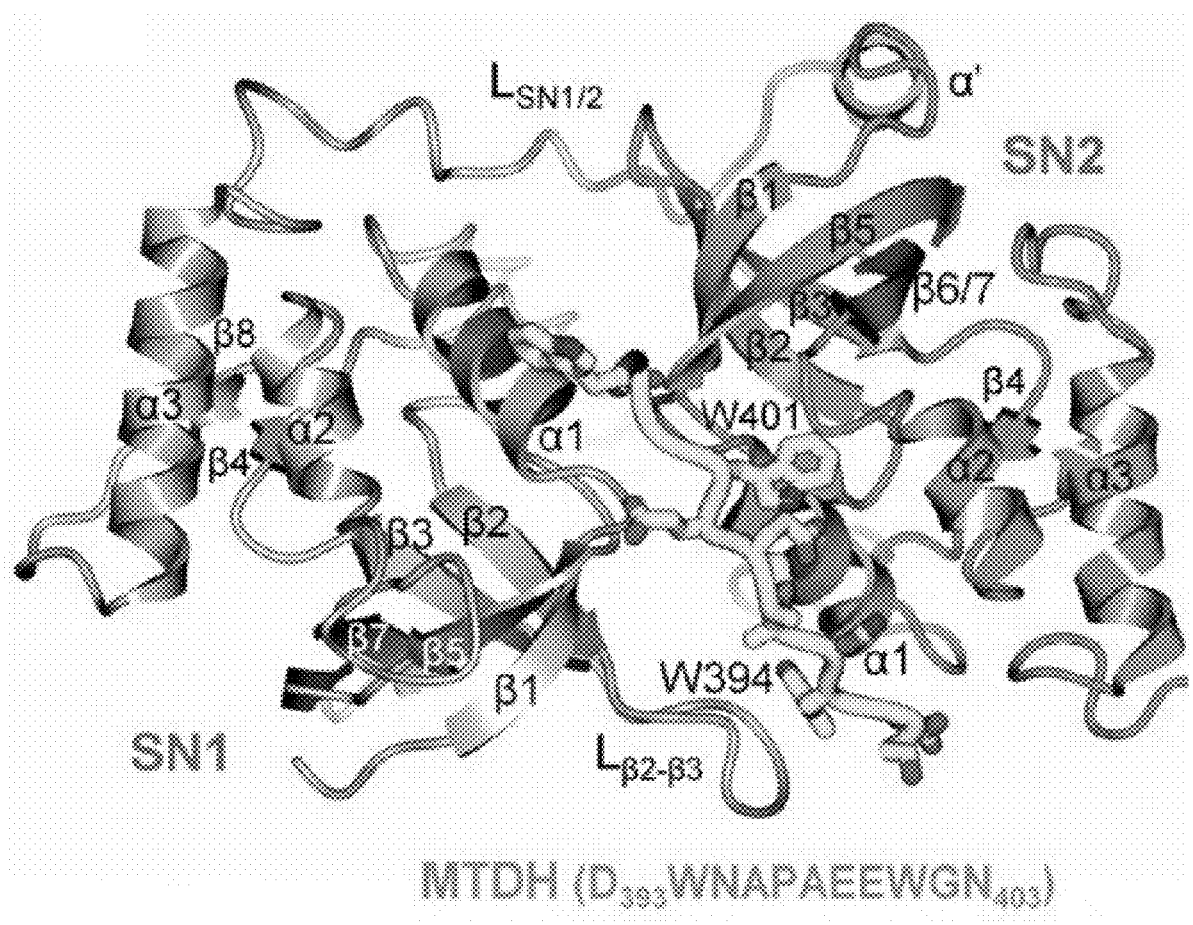
FIG. 19) shows mapping of SND1-MTDH interaction and overall structure of their complex. Overall structure of MTDH-SND1 complex. Two perpendicular views are shown. The SN1 and SN2 domains of SND1 and MTDH are colored cyan, magenta and yellow, respectively. SND1 is shown in ribbon (left) and surface (right). MTDH is shown in worm (backbone) and cylinder (side chain).
Figures 20A, 20B:
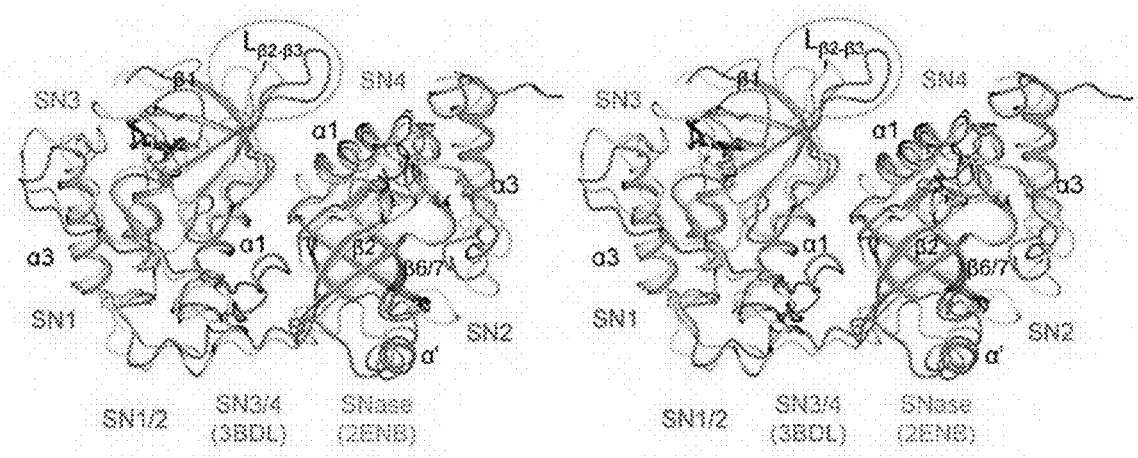
FIGS. 20A-B represents a structural and sequence comparison of SN1/2 with SN3/4 and SNase.

Structural comparison of SN1/2 with SN3/4 and SNase: Superimposition of the structures of SN1/2, SN3/4 (PDB code: 3BDL) and two copies of SNase (PDB code: 2ENB) reveals similar structures in β-sheets and α-helices (FIG. 19), with the root-mean-square-deviation of 2.02 Å over 268 residues between SN1/2 and SN3/4, 1.67 Å over 123 residues between SN1 and SNase, and 1.68 Å over 116 residues between SN2 and SNase. Several loop regions, however, are distinctly different, with varied length and amino acid sequences (FIGS. 20A and 20B). These are likely novel features evolved from OB-fold to confer new functionality. For example, as shown in detail later, the elongated Lβ2-β3 loop in SN1 is crucial for mediating MTDH binding. The Lβ4-α1 loops in SN1 and SN3 are significant longer than that in SNase, and they adopt distinctly different conformations, which likely define different specificity for the two SN domains. Two out of six residues at the SNase active site are retained in SN3, only one of these residues remains the same or similar in SN1 and SN4, but none of them is retained in SN2 (FIG. 20B). This is consistent with the previous observation that SN3/4 exhibit a low nuclease activity, while SN1/2 augment the nuclease activity (Li et al., 2008), presumably by enhancing substrate-binding. These observations suggest that novel functions have been evolved for the SN domains in SND1, but the nuclease activity in these SN folds was reduced (in SN3/4) or diminished (in SN1/2) during evolution.

MTDH-SND1 interaction interface: The fact that MTDH occupies an extended groove between SN1 and SN2 on the back of the hilly surface of SND1 is consistent with the notion that MTDH might serve as a scaffold signaling protein. This architecture may allow MTDH to bridge SND1 and other MTDH-associated signaling complexes without interfering with major binding surfaces of SND1. The MTDH-SND1 interface thus provides an important basis for understanding diverse downstream signaling and their function in cancer.

Figure 21:
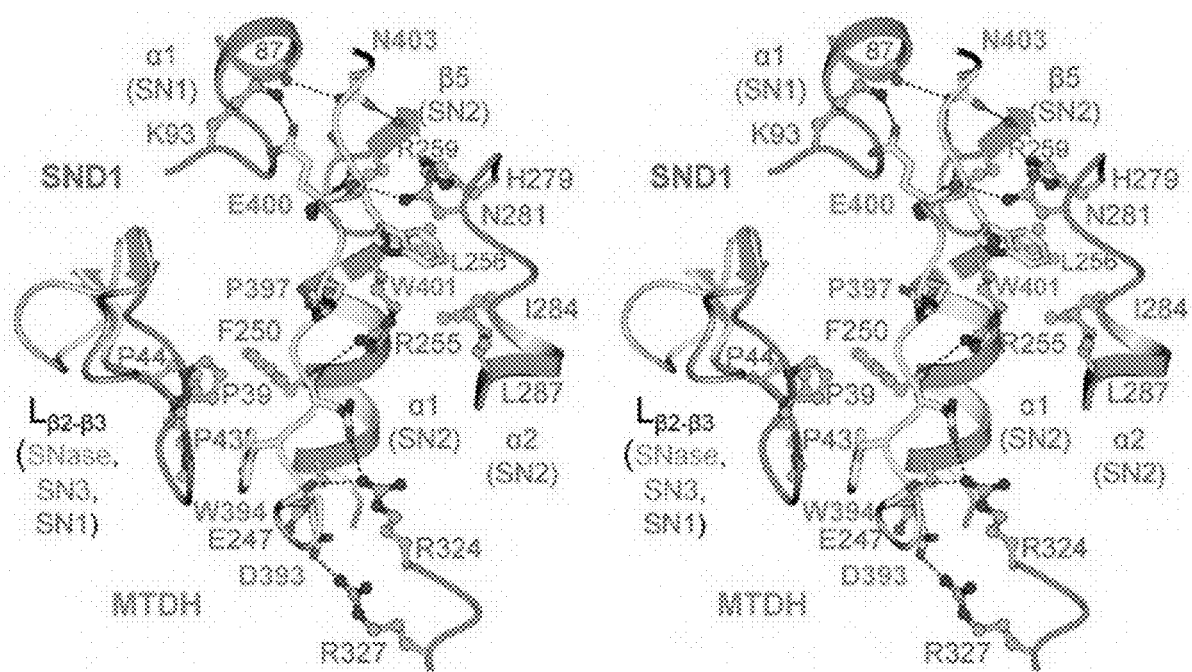
FIG. 21 illustrates the MTDH-SND1 binding interface. A close-up stereo of MTDH-SND1 interface. The Lβ2-β3 loops from SN3 domain (light blue) and SNase (yellow) are shown for highlighting the unique structure of SN1 Lβ2-β3 loop required for MTDH-binding.

The interface is dominated by hydrophobic van der Waals contacts of W394 and W401 in MTDH with two separate, well-defined hydrophobic pockets in SND1, which are buttressed by hydrogen bond (H-bond) and salt bridge interactions at the periphery of the pockets (FIG. 21). The hydrophobic pocket for W394 is formed by residues P39, P43, and P44 in the SN1 Lβ2-β3 loop and the side chains of E247 and F250 on the SN2 α1 helix. The pocket for W401 is about 15 Å away and located between the α1 and α2 helices from SN2, and contoured by hydrophobic residues L256, H279, I284, and L287 and the carbon chain region of residues R255, R259, and N281. At the periphery of the hydrophobic pockets near one end of the interface, R327 and R324 in SND1 form several H-bond and salt bridge interactions with D393 and N395 in MTDH and its backbone carbonyl group at 392 in two of the five complexes in the asymmetric unit; in the middle, R255 in SND1 forms an H-bond interaction with the MTDH backbone at 395; and at the other end, a few H-bond and salt bridge interactions are formed by residues and backbone atoms from SN1 α1 helix and SN2 β5 strand with MTDH residues, E400 and N403.

The interface for MTDH in SND1 is highly unique and present only in SN1/2. The well-defined hydrophobic pockets for W394 and W401 are clearly shown by the surface contour of SN1/2 with electrostatic potential, but are absent in SN3/4. The surface between the two hydrophobic pockets in SN1/2 is basic, which in part favors the electrostatic interaction with E400, but is not ideal for interaction with nonpolar residues (A396PA398) between W394 and W401. This likely explains the relatively weak interaction between SND1 and MTDH and the fast off-rate of this interaction. Unlike SN1/2, the protein groove between SN3 and SN4 is largely basic, underlying another structural feature of SN3/4 that disfavours MTDH-binding. Furthermore, the proline residues in the SN1 Lβ2-β3 loop that are essential for lining the pocket for W394 are all absent in SN3 or SNase (FIG. 20B, FIG. 21), further defining the binding specificity of SN1/2 to MTDH.

Figure 22A:
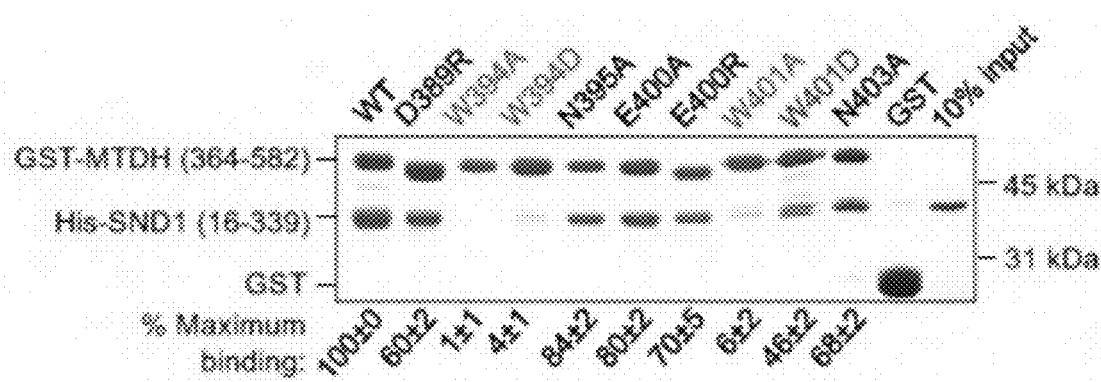
FIGS. 22A-D shows the identification of MTDH and SND1 mutants deficient in binding.

Identification of MTDH and SND1 mutants deficient in binding: To gain insight into how the interface characterized above contributes to MTDH-SND1 interaction, structure-guided mutagenesis studies were performed. The MTDH-SND1 structure suggests that the van der Waals hydrophobic contacts made by MTDH W394 and W401 might play a dominant role in SND1-binding. Consistent with this notion, mutations of either of the two tryptophan residues to a much smaller residue alanine (W394A, W401A) or a negatively-charged residue aspartate (W394D, W401D) abolished or significantly reduced the interaction between SND1 (16-339) and MTDH (364-582) in vitro (FIG. 22A). The W→A mutants exhibited stronger defects than the W→D mutants, and mutations with W394 resulted in more severe defects than mutations with W401, suggesting that the MTDH-SND1 interaction is largely dictated by van der Waals contacts and that W394 makes a higher contribution to SND1-binding than W401. The MTDH mutations at the periphery interface (N395A, E400A, E400R, N403A), which are expected to disrupt H-bond or salt bridge interactions, barely had any effect, resembling the mutation that targets D389 outside the interface (D389R) (FIG. 22A). It is likely that individual H-bond makes minor contributions to the MTDH-SND1 interaction. These results are consistent with the structural observation and support the notion that the interaction between MTDH and SND1 is dominated by van der Waals contacts between MTDH tryptophan residues and the hydrophobic pockets in SND1.

Figure 22B:
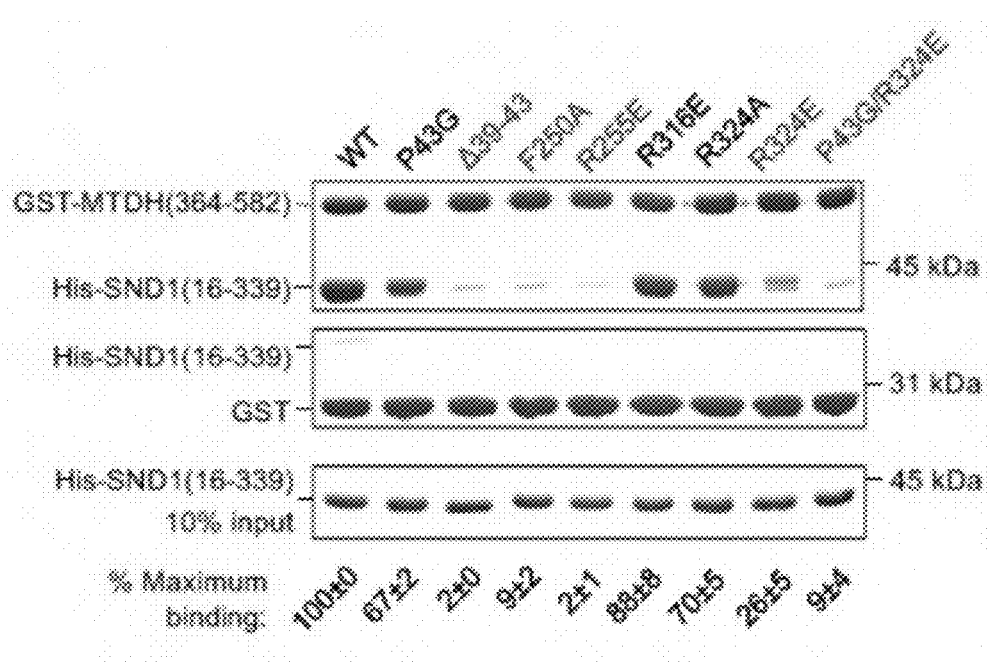

Several SND1 mutations at the interface that disrupt MTDH-binding were also identified. Changes made to the SND1 hydrophobic pockets, including R255E, F250A, and deletion in the SN1 Lβ2-β3 loop (Δ39-43), almost completely abolished MTDH-binding (FIG. 22B). In addition to perturbation of the van der Waals contacts with W401, R255E might also affect its H-bond interaction with the MTDH backbone (FIG. 21). The effect of 439-43 further supports the role of these residues uniquely found in the SN1 Lβ2-β3 loop (FIGS. 20A, 20B and 21) for MTDH-binding. The R324E mutation significantly weakened the MTDH-binding, likely by introducing a repulsive charge-charge contact with D393 in MTDH. A different mutation to this residue, R324A, which was expected to perturb its H-bond interactions, barely affected MTDH-binding, similar to the negative control, R316E, an SND1 mutation located outside the interface.

Figure 22C:
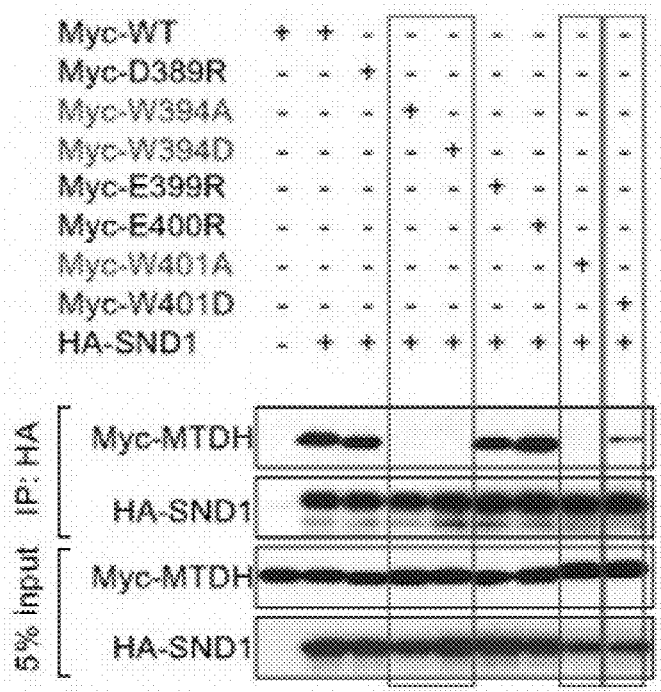
Figure 22D:
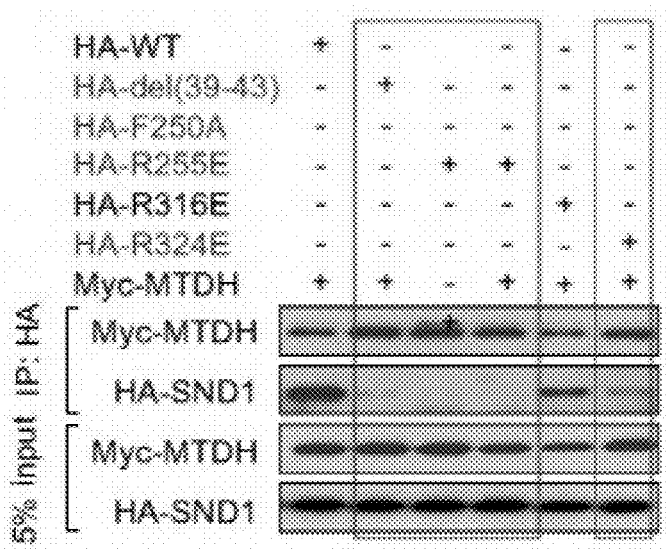

It was further examined how the MTDH and SND1 mutations identified at this interface affected the interaction of full-length proteins in mammalian cells. Full-length HA-tagged SND1 was co-expressed with full-length Myc-tagged wild-type (WT) or mutant MTDH in HEK293T cells and cell lysates were subjected to anti-HA immunoprecipitation for SND1 pull down. Consistent with in vitro observations (FIG. 22A), WT MTDH, but not mutants W394A, W394D, or W401A, was pulled down along with HA-SND1 (FIG. 22C, in red). MTDH mutation W401D significantly reduced the binding (FIG. 22C, in blue), whereas other mutations, including the negative control D389R, a mutation located outside the MTDH-SND1 interface, did not affect the interaction (FIG. 22C). Likewise, the SND1 mutations that affected MTDH-binding in vitro also affected the binding of full-length proteins in vivo to similar levels. Both WT HA-SND1 and the negative control mutant, HA-SND1 R316E, bound readily with Myc-MTDH, whereas other mutations, 439-43, F250A, or R255E, nearly completely abolished MTDH-binding, and R324E significantly reduced the binding (FIG. 22D).

The similar results of in vitro and in vivo studies on MTDH-SND1 interaction strongly suggest that the MTDH-SND1 interface characterized above dictates the interaction of the full-length MTDH and SND1 in mammalian cells. This allowed further definition the role of this interface in controlling the function of MTDH and SND1 in cancer promotion.

MTDH mutants deficient in SND1-binding had reduced pro-tumorigenic activities: As demonstrated above MTDH plays a role in regulating mammary tumorigenesis. In particular, genetic deletion of Mtdh in mice impairs the tumor-initiating potential of mammary epithelial cells transformed by diverse oncogenes (PyMT, Wnt, ErbB2) or carcinogen stimuli, and this defect can be readily rescued by reintroducing MTDH into Mtdh-knockout (Mtdh−/−) tumor cells by lentiviral transduction. To test whether interacting with SND1 is important for the tumor-initiating effect of MTDH, the murine form of WT or mutant MTDH (W394A or W401A, corresponding mutations in mouse are W391A, W398A) was stably expressed in mammary tumor cells from PyMT;Mtdh−/− mice. The MTDH mutants W394A or W401A completely lost the ability to interact with SND1 (FIG. 23A), suggesting that the SND1-interacting residues of MTDH are well conserved between mouse and human. Functionally, in vitro mammosphere formation assays showed that PyMT;Mtdh−/− tumor cells reconstituted with mutant MTDH formed a significantly lower number of spheres compared to those reconstituted with WT MTDH (FIG. 23B). To examine how MTDH mutations affect tumor formation in vivo, PyMT;Mtdh−/− tumor cells were orthotopically transplanted into the mammary fat pads of WT recipient mice. It was found that PyMT;Mtdh−/− tumor cells reconstituted with mutant MTDH contained substantially fewer tumor-initiating cells as revealed by reduced tumor incidence (FIG. 23C) when a limited number of cells were injected. Furthermore, the size of tumors formed by PyMT;Mtdh−/− tumor cells reconstituted with mutant MTDH was much smaller than that with WT MTDH (FIG. 23D-E). These results demonstrate that the interaction between MTDH and SND1 is essential for the pro-tumorigenic activity of MTDH.

Figure 24A:
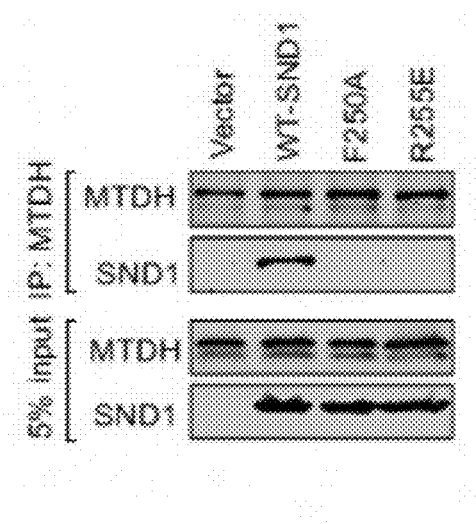
FIGS. 24A-D shows that mutations in MTDH-binding pockets impair tumor-promoting function of SND1.
Figure 24B:
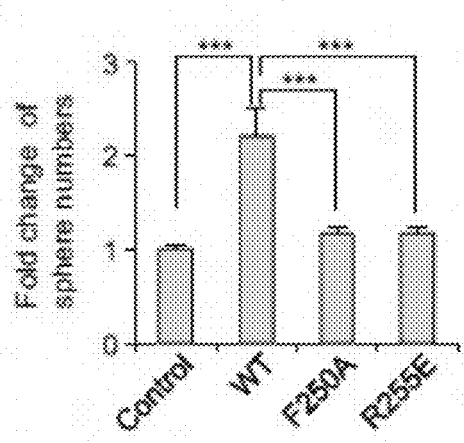
Figure 24C:
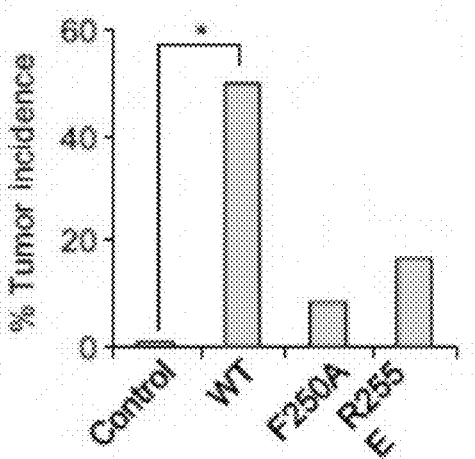
Figure 24D:
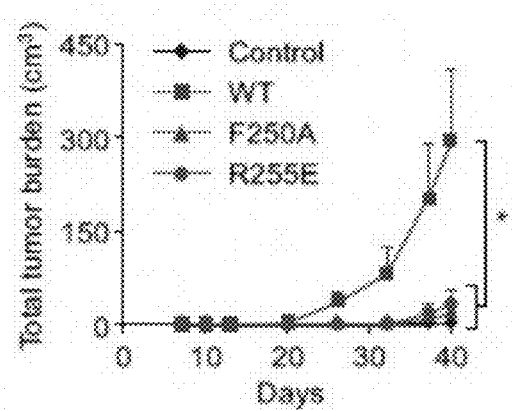

SND1 mutants deficient in MTDH-binding were inactive in tumor promotion: The well-defined pockets in SND1 for MTDH-binding and the role of this interaction in tumor initiation suggests that the protein pockets in SND1 represent a novel therapeutic target for cancer. As demonstrated above, knockdown (KD) of SND1 impairs the tumor initiating activities of PyMT/Mtdh+/+ tumor cells, supporting a tumor-promoting role of SND1 (Wan et al, 2014). In the current study, an shRNA-resistant construct of WT or mutant SND1 (F250A or R255E) was stably expressed in SND1-KD PyMT/Mtdh+/+ tumor cells and their effects on tumor initiating activities were tested in vitro and in vivo. The SND1 mutations nearly completely abolished the interaction with MTDH (FIG. 24A). SND1 mutants barely led to any increase in the number of spheres formed in the in vitro mammosphere assays, whereas WT SND1 increases the sphere numbers by more than 2-fold as compared to controls (FIG. 24B). After transplantation of the cells into mammary fat pads of recipient mice, WT SND1 markedly boosted tumor initiation and tumor growth as reflected by tumor incidence and total tumor burden, whereas SND1 mutants exhibited very minor effects (FIG. 24D). These results further support our conclusion that the interaction between MTDH and SND1 is important for tumor promotion, and that both MTDH-binding pockets in SND1 are crucial for this activity.

Figure 25:
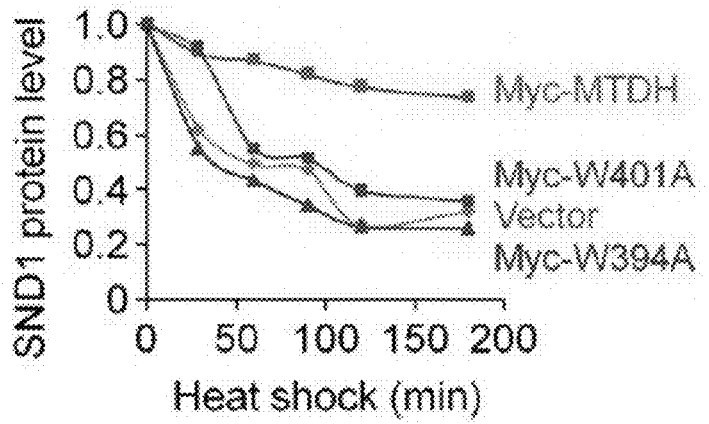
FIG. 25 shows MTDH interaction protects SND1 from heat shock stress-induced degradation. HEK293T cells were transfected with HA-SND1 together with either empty vector control or indicated WT or mutant Myc-MTDH constructs. Two days post infections, cells were treated under heat shock conditions and lysates were immunoblotted for indicated proteins. β-actin was used as loading control. Representative results of three independent experiments are shown.

MTDH mutants deficient in SND1-binding failed to stabilize SND1 under stress: These recent studies suggested that MTDH plays a key role in enhancing the stability of SND1 protein under stress conditions, which may contribute to the pro-survival role of SND1 in cancer cell under oncogenic or other stresses (Gao et al., 2010; Sundstrom et al., 2009; Weissbach and Scadden, 2012). To substantiate this notion, the effects of MTDH mutations on the cellular stability of SND1 under heat shock were examined, a condition under which SND1 has been demonstrated to be important for cellular survival (Gao et al., 2010; Weissbach and Scadden, 2012). When overexpressed alone, the cellular level of HA-SND1 was rapidly reduced at 45° C., with a half-life of around 30 minutes (FIG. 25). Co-expression with WT Myc-MTDH augmented the cellular stability of HA-SND1 at 45° C., with the half-life extended beyond 3 hours, whereas co-expression of either MTDH mutants, W394A and W401A, failed to stabilize HA-SND1 under heat shock. This result supports the role of MTDH-SND1 interaction in promoting the cellular stability of SND1, consistent with our recent observation that the protein levels of MTDH and SND1 are positively correlated in human breast cancers (see above).

Discussion

MTDH has gained increasing interest in recent years given its broad implication in diverse cancer types, and SND1 has been documented as a MTDH-binding protein that possesses tumor-promoting functions similar to MTDH (Emdad et al., 2013; Wan and Kang, 2013). However, the structural basis and functional significance of the interaction remain unclear. Our studies here mapped the minimal interaction motif/domain of MTDH and SND1 and determined the high-resolution crystal structure of their complex. Structural analysis and structure-guided functional studies showed that the MTDH-SND1 interface is essential for MTDH and SND1's activities in mammary tumor initiation, and harbors structural features promising as a novel cancer therapeutic target. In addition, the structure of the MTDH-SND1 complex provides an important platform for future understanding of cancer cell signaling bridged by this interaction.

The MTDH-SND1 interface characterized in this study provides key insights into the molecular basis of their interaction. The essential SND1-binding motif was previously mapped to two different regions of MTDH, residues 364-470 of SEQ ID NO: 1 (Blanco et al., 2011) and residues 101-205 of SEQ ID NO: 1 (Yoo et al., 2011). The study here defined a short 11-residue peptide motif (residues 393-403 of SEQ ID NO: 1) of MTDH as the primary SND1-binding motif, which is located within the fragment identified by Blanco et al (Blanco et al., 2011). Mutations in either MTDH or SND1 at this interface abolished the interaction of the full-length proteins both in HEK293T cells and in breast tumor cells, supporting the notion that this interface is the dominant binding site between MTDH and SND1.

The prominent function of the MTDH-SND1 interface in cancer promotion suggests that targeting this interface might be a useful strategy for cancer therapy. In addition, our results suggest important ways for targeting this interface. The interaction between MTDH and SND1 is dominated by van der Waals contacts between W395 and W401 in MTDH and two well-defined hydrophobic pockets in SND1 that are appealing for binding of small molecule inhibitors. Importantly, mutations in MTDH or SND1 at either binding pocket abolished their activity in promotion of mammary tumor initiation, thus making simultaneously targeting both SND1 pockets an attractive therapeutic approach. Other appealing features of this interface for targeting include the readily reversible binding between MTDH and SND1, suggesting that this interaction could be reversed by specific inhibitors. Furthermore, the MTDH-binding pockets are uniquely evolved in SN1/2 domains but absent in other OB-fold superfamily proteins or other SN domains in SND1, underlying promises of developing compounds highly specific for blocking MTDH-binding.

The structure of the MTDH-SND1 interface provides an important platform for understanding the cellular signaling coordinated by this interaction. Despite the structural similarity between SN1/2 and SN3/4 domains, SN3/4 does not possess the unique pockets and surface feature required for MTDH-binding. Furthermore, the hilly surfaces harboring protruding structures in SN1/2 and SN3/4 are distinctly different and are expected to confer different binding specificity. The domains in SND1 fragment containing SN3/4-TSN5 domains were shown to be arranged in a linear orientation with a crescent shape (Li et al., 2008). FRET analysis indicated that the distance between the termini of the full-length SND1 was farther than that of the SN3/4-TSN5 fragment, suggesting that the multiple SND1 domains are arranged in a linear fashion. This architecture likely allows different binding partners to be orchestrated in a coherent orientation for downstream signaling. Surprisingly, MTDH associates with SND1 via a short peptide to a surface of SND1 that is rather flat and distinctly different from that hilly surface located at the opposite side. This simple mode of binding is in a sharp contrast to the robust function of this interface in cancer promotion, suggesting that downstream signaling mediated by this interface might contribute to the multifaceted roles of MTDH and SND1 in cancer. It is important to note that, besides a single transmembrane domain, the entire sequence of MTDH with almost five hundred residues is largely disordered, suggesting the possibility that MTDH could interact with many signaling proteins. These feature resembles that of signaling scaffold proteins, such as AKAPs (a kinase anchor proteins (Gelman, 2012), suggesting that MTDH might function as a signaling scaffold protein. Together with SND1, MTDH might mediate cellular signaling via diverse signaling molecules orchestrated by the multiple interaction domains/motifs of SND1 and MTDH.

The reliance of SND1 stability on MTDH-binding under stress provides another explanation for the role of MTDH-SND1 interaction in cancer. This result is also consistent with the observation that MTDH and SND1 were simultaneously elevated in tumor tissues (see above and Wang et al., 2012). How the MTDH-SND1 interaction contributes to SND1 stability under stress, however, remains to be determined. The current in vitro study demonstrated that MTDH-binding had a minimal effect on the thermal stability of SN1/2 domains or their sensitivity to protease cleavage, suggesting that MTDH-binding might not directly stabilize SND1. Further studies are needed to decipher whether the cellular stability of SND1 relies on recruitment of other biomolecules.

Example 4—Wild Type MTDH Peptides Significantly Block MTDH-SND1 Interaction

Figure 26A:
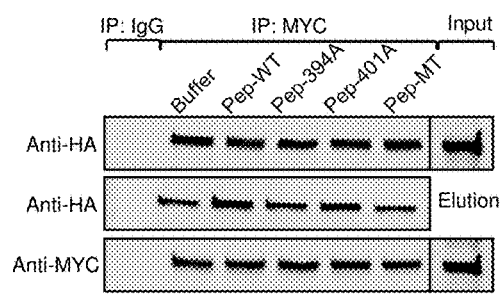
FIGS. 26A-D show wild type MTDH peptide significant block MTDH-SND1 interaction. 293T cells co-transfected with HA-SND1 and MYC-MTDH. After 48 hr cells were collected and subjected to IP assay.
Figure 26C:
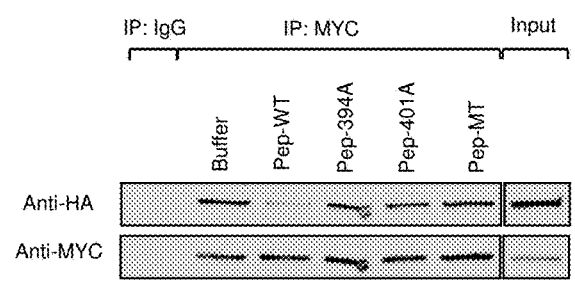
Figure 26B:
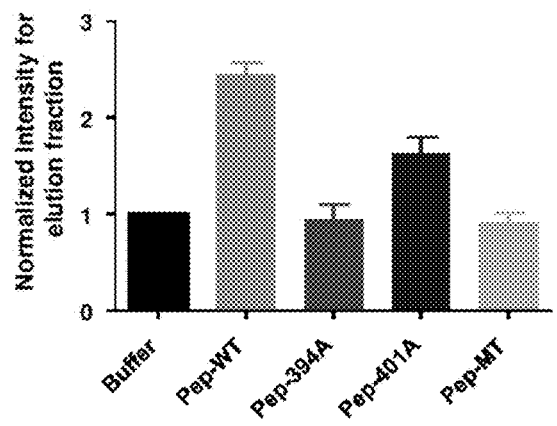

293 T cells were co-transfected with HA-SND1 and MYC-MTDH. After 48 hours, the cells were collected and subject to immunoprecipitation assay. See FIG. 26A and FIG. 26B. Cell lysate was incubated with anti-HA antibody or IgG overnight followed by a two hour incubation with Protein A/G beads to pull down HA-SND1 protein. The beads were washed with lysis buffer and split into five fractions. Each fraction was eluted with buffer or indicated peptides (i.e., Peptide-wt (PNSDWNAPAEEWGNW, SEQ ID NO: 16); Peptide-394A (PNSDANAPAEEWGNW, SEQ ID NO: 17); Peptide-401A (PNSDWNAPAEEAGNW, SEQ ID NO: 18) and Peptide-MT (PNSDANAPAEEAGNW, SEQ ID NO: 19) for 30 minutes.

Figure 26D:
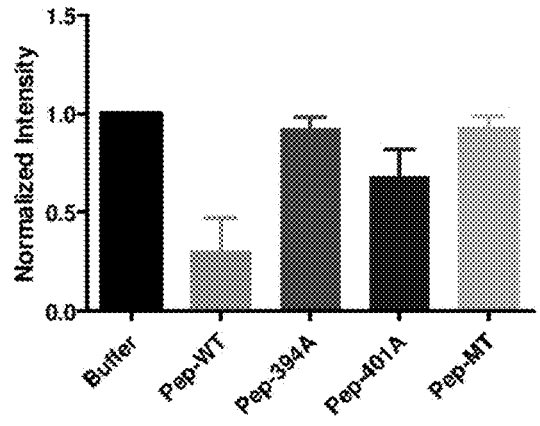

The elution fractions and beads were collected for western blot. (FIGS. 26C and 26D) Cell lyaste was split into 6 fractions. One of the fractions was incubated with IgG and the rest were incubated with anti-HA antibody plus either buffer or indicated peptides. After 24 hours, the lysate was incubated with Protein A/G beads then the beads was washed followed by wash buffer. 50 uM of peptides was used in all the assays.

Figure 27A:
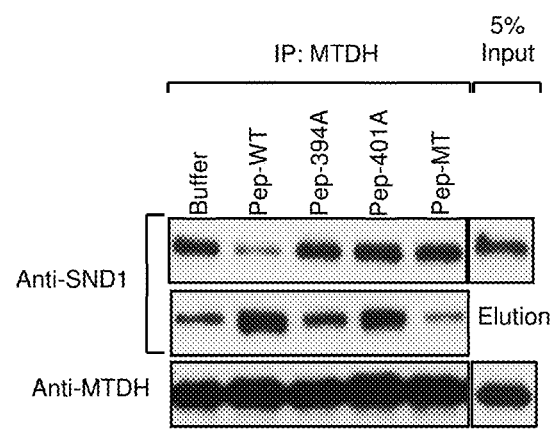
FIGS. 27A-B show that the interaction interrupt effect was confirmed by endogenous immunoprecipitation of a breast cancer cell line. Breast cancer cells MDA-MB231 were collected and subjected to IP assay.
Figure 27B:
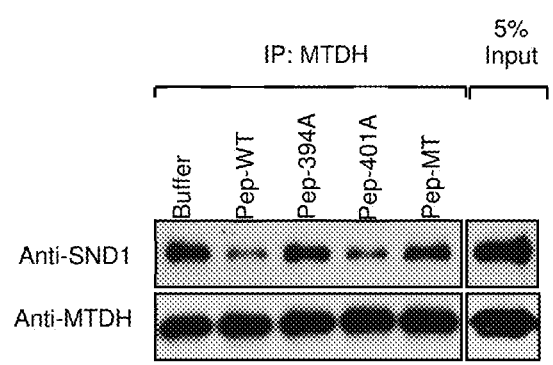

The interaction interruption effects was confirmed by endogenous immunoprecipitation (IP) of a breast cancer cell line. Briefly, cell lysates from the breast cancer cell line MDA-MB-231 were collected and subjected to IP assay. Results are provided in FIG. 27A and FIG. 27B. FIG. 27A—Cell lysate was incubated with anti-SND1 antibody or IgG overnight followed by 2 hr incubation with Protein A/G beads to pull down endogenous SND1 protein. The beads was washed with lysis buffer and split into 5 fractions. Each fraction was eluted with buffer or indicated peptides for 30 min. The elution fractions and beads were collected for WB. FIG. 27B—Cell lyaste was split into 5 fractions, and incubated with anti-SND1 antibody plus either buffer or indicated peptides. After 24 hr, the lysate was incubated with Protein A/G beads then the beads was washed followed by western blot.

The above results indicated that the wild type MTDH peptide can effectively block MTDH-SND1 interaction. A peptide comprising the single point mutation W401A reduced the effectiveness of the wild type peptide by half. It was also observed that inserting the single point mutation W394A or a double point mutation have no effect in interrupting the interaction of MTDH with SND1.

Example 5—Sequence Variations that Retain MTDH-SND1 Interactions

The high-resolution crystal structure of MTDH-SND1 complex revealed an 11-residue peptide motif of Metadherin (MTDH) for binding to an extended protein groove of Staphylococcal nuclease domain containing 1 (SND1). MTDH and SND1 mutants at this interface deficient in binding have reduced activity in cancer promotion, which establishes the significance of this interface as a novel target for developing cancer therapeutics. The peptide motifs at this interface and their derivatives are potential inhibitors for blocking this interaction. To explore the sequence variations of MTDH peptide at the interface with SND1 that retain SND1-binding, structure-guided mutational analysis was performed for residues other than W394 and W401, the two residues that bind to two well-defined pockets in SND1. None of the mutations have an obvious effect on MTDH-SND1 binding. This provides a large flexibility in designing peptide and peptide mimic inhibitors and allow flexible chemistry in making such inhibitors.

Experimental Procedures

Protein Preparation: All constructs and point mutations were generated using a standard PCR-based cloning strategy. Briefly, SND1 and MTDH with different boundaries and mutants were cloned in pQlink vector (Addgene) harboring an N-terminal His8-tag and a GST-tag, respectively, with a TEV cleavage site after the affinity tag. The proteins were overexpressed at 23° C. in *E. coli* strain DH5a. Expression and purification of SND1 and SND1 (16-339)-L21-MTDH (386-407) followed the procedure modified from previous publication (Li et al., 2008).

GST-Mediated Titration Pull-Down Assay: ~20 µg of GST-MTDH (386-407, wild type and different mutants) was bound to 10 µl of glutathione resin via GST tag. The resin was washed with 200 µl assay buffer (25 mM Tris, PH8.0, 150 mM NaCl, 3 mM DTT) three times to remove the excess unbound protein. 15 µg of His-SND1 (16-339) with titrated concentrations (10, 3, 1, 0.5, 0.25, 0.12 µM) was added to the resin in a 500 µl volume suspended in the assay buffer with 2 mg/ml of BSA. The mixture was washed with 500 µl assay buffer twice before examined by SDS-PAGE, and visualized by Coomassie blue staining.

Results

Figure 28:
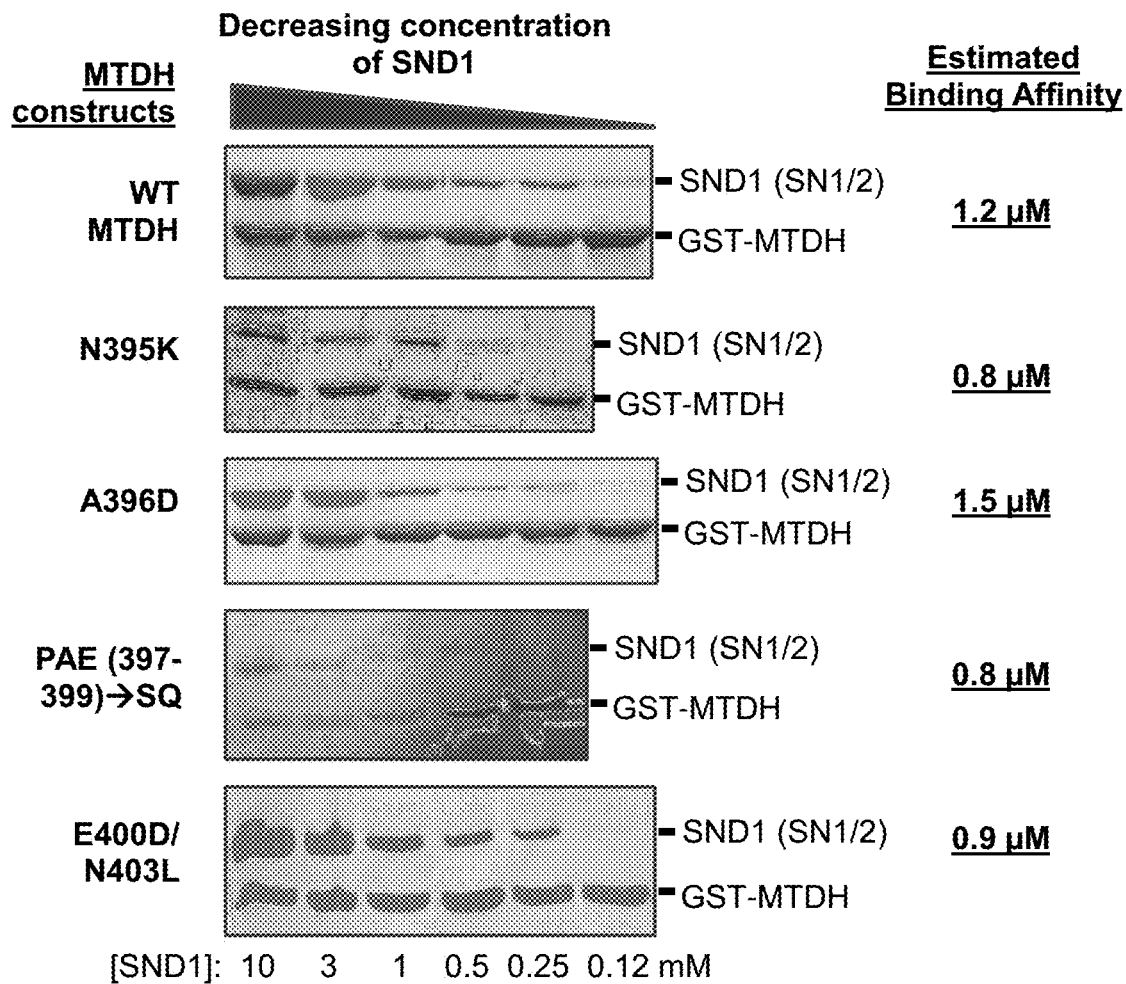
FIG. 28 shows the identification of MTDH mutants bearing mutations in the SND1-binding motif that has no or little effect on SND1-binding. In vitro pull-down of SND1 (amino acids 16-339 of SEQ ID NO: 2) by GST-tagged MTDH (amino acids 386-407 of SEQ ID NO: 1) harboring WT or mutant sequence. The proteins bound to GS4B were examined on SDS-PAGE and visualized by Coomassie blue staining.

Amino acid sequence variations of MTDH that retain SND1-binding: The degree of sequence variations in the peptide motif represents the level of flexibility in the chemistry of developing peptide mimic inhibitors. To explore such possibilities, based on the mode of MTDH-SND1 interactions revealed by the high-resolution structure of the MTDH-SND1 complex, further mutational analysis to MTDH residues at or near the interface with SND1 was performed. Novel mutations to seven residues were made and their binding affinities with $His_6$-SND1 harboring the SN1/2 domains (amino acids 16-339 of SEQ ID NO: 2) were measured by titration pull-down assays (FIG. 28). All MTDH mutants gave a binding affinity within 0.7-1.3 fold of that for wild type MTDH. W394 and W401 were not included in this mutation list because mutation to these two residues were shown earlier to have strong impacts on interaction with SND1. Limited mutations to W394 and W401, such as replacement with Tyr and Phe, are expected to retain a small fraction of the binding affinity to SND1. There is little tolerance of mutations to these two residues for retaining SND1-binding. The collected results here and earlier mutational studies support a generally large tolerance of mutations to other sites of MTDH for retaining SND1-binding. This provides a significant flexibility in designing peptide inhibitors and peptide mimic inhibitors.

REFERENCES

Asselin-Labat, M. L., Sutherland, K. D., Barker, H., Thomas, R., Shackleton, M., Forrest, N. C., Hartley, L., Robb, L., Grosveld, F. G., van der Wees, J., et al. (2007). Gata-3 is an essential regulator of mammary-gland morphogenesis and luminal-cell differentiation. Nature cell biology 9, 201-209.

Bernards, R., and Weinberg, R. A. (2002). A progression puzzle. Nature 418, 823.

Blanco, M. A., Aleckovic, M., Hua, Y., Li, T., Wei, Y., Xu, Z., Cristea, I. M., and Kang, Y. (2011). Identification of staphylococcal nuclease domain-containing 1 (SND1) as a Metadherin-interacting protein with metastasis-promoting functions. J Biol Chem 286, 19982-19992.

Brown, D. M., and Ruoslahti, E. (2004). Metadherin, a cell surface protein in breast tumors that mediates lung metastasis. Cancer Cell 5, 365-374.

Buchwalter, G., Hickey, M. M., Cromer, A., Selfors, L. M., Gunawardane, R. N., Frishman, J., Jeselsohn, R., Lim, E., Chi, D., Fu, X., et al. (2013). PDEF promotes luminal differentiation and acts as a survival factor for ER-positive breast cancer cells. Cancer Cell 23, 753-767.

DeRose, Y. S., Wang, G., Lin, Y. C., Bernard, P. S., Buys, S. S., Ebbert, M. T., Factor, R., Matsen, C., Milash, B. A., Nelson, E., et al. (2011). Tumor grafts derived from women with breast cancer authentically reflect tumor pathology, growth, metastasis and disease outcomes. Nature medicine 17, 1514-1520.

Emdad, L., Das, S. K., Dasgupta, S., Hu, B., Sarkar, D., and Fisher, P. B. (2013). AEG-1/MTDH/LYRIC: signaling pathways, downstream genes, interacting proteins, and regulation of tumor angiogenesis. Advances in cancer research 120, 75-111.

Gao, X., Ge, L., Shao, J., Su, C., Zhao, H., Saarikettu, J., Yao, X., Yao, Z., Silvennoinen, O., and Yang, J. (2010). Tudor-SN interacts with and co-localizes with G3BP in stress granules under stress conditions. FEBS Lett 584, 3525-3532.

Ginestier, C., Hur, M. H., Charafe-Jauffret, E., Monville, F., Dutcher, J., Brown, M., Jacquemier, J., Viens, P., Kleer, C. G., Liu, S., et al. (2007). ALDH1 is a marker of normal and malignant human mammary stem cells and a predictor of poor clinical outcome. Cell Stem Cell 1, 555-567.

Guo, W., Keckesova, Z., Donaher, J. L., Shibue, T., Tischler, V., Reinhardt, F., Itzkovitz, S., Noske, A., Zurrer-Hardi, U., Bell, G., et al. (2012). Slug and Sox9 cooperatively determine the mammary stem cell state. Cell 148, 1015-1028.

Halazonetis, T. D., Gorgoulis, V. G., and Bartek, J. (2008). An oncogene-induced DNA damage model for cancer development. Science 319, 1352-1355.

Herschkowitz, J. I., Simin, K., Weigman, V. J., Mikaelian, I., Usary, J., Hu, Z., Rasmussen, K. E., Jones, L. P., Assefnia, S., Chandrasekharan, S., et al. (2007). Identification of conserved gene expression features between murine mammary carcinoma models and human breast tumors. Genome Biol 8, R76.

Hu, G., Chong, R. A., Yang, Q., Wei, Y., Blanco, M. A., Li, F., Reiss, M., Au, J. L., Haffty, B. G., and Kang, Y. (2009). MTDH activation by 8q22 genomic gain promotes chemoresistance and metastasis of poor-prognosis breast cancer. Cancer Cell 15, 9-20.

Kouros-Mehr, H., Bechis, S. K., Slorach, E. M., Littlepage, L. E., Egeblad, M., Ewald, A. J., Pai, S. Y., Ho, I. C., and Werb, Z. (2008). GATA-3 links tumor differentiation and dissemination in a luminal breast cancer model. Cancer Cell 13, 141-152.

Lento, W., Congdon, K., Voermans, C., Kritzik, M., and Reya, T. (2013). Wnt signaling in normal and malignant hematopoiesis. Cold Spring Harbor perspectives in biology 5.

Li, Y., Welm, B., Podsypanina, K., Huang, S., Chamorro, M., Zhang, X., Rowlands, T., Egeblad, M., Cowin, P., Werb, Z., et al. (2003). Evidence that transgenes encoding components of the Wnt signaling pathway preferentially induce mammary cancers from progenitor cells. Proc Natl Acad Sci USA 100, 15853-15858.

Mani, S. A., Guo, W., Liao, M. J., Eaton, E. N., Ayyanan, A., Zhou, A. Y., Brooks, M., Reinhard, F., Zhang, C. C., Shipitsin, M., et al. (2008). The epithelial-mesenchymal transition generates cells with properties of stem cells. Cell 133, 704-715.

Meng, X., Zhu, D., Yang, S., Wang, X., Xiong, Z., Zhang, Y., Brachova, P., and Leslie, K. K. (2012). Cytoplasmic Metadherin (MTDH) provides survival advantage under conditions of stress by acting as RNA-binding protein. J Biol Chem 287, 4485-4491.

Perou, C. M., Sorlie, T., Eisen, M. B., van de Rijn, M., Jeffrey, S. S., Rees, C. A., Pollack, J. R., Ross, D. T., Johnsen, H., Akslen, L. A., et al. (2000). Molecular portraits of human breast tumours. Nature 406, 747-752.

Shackleton, M., Vaillant, F., Simpson, K. J., Stingl, J., Smyth, G. K., Asselin-Labat, M. L., Wu, L., Lindeman, G. J., and Visvader, J. E. (2006). Generation of a functional mammary gland from a single stem cell. Nature 439, 84-88.

Sundstrom, J. F., Vaculova, A., Smertenko, A. P., Savenkov, E. I., Golovko, A., Minina, E., Tiwari, B. S., Rodriguez-Nieto, S., Zamyatnin, A. A., Jr., Valineva, T., et al. (2009). Tudor staphylococcal nuclease is an evolutionarily conserved component of the programmed cell death degradome. Nature cell biology 11, 1347-1354.

Vaillant, F., Asselin-Labat, M. L., Shackleton, M., Forrest, N. C., Lindeman, G. J., and Visvader, J. E. (2008). The mammary progenitor marker CD61/beta3 integrin identifies cancer stem cells in mouse models of mammary tumorigenesis. Cancer research 68, 7711-7717.

van de Vijver, M. J., He, Y. D., van't Veer, L. J., Dai, H., Hart, A. A., Voskuil, D. W., Schreiber, G. J., Peterse, J. L., Roberts, C., Marton, M. J., et al. (2002). A gene-expression signature as a predictor of survival in breast cancer. The New England journal of medicine 347, 1999-2009.

Vanharanta, S., and Massague, J. (2013). Origins of metastatic traits. Cancer Cell 24, 410-421.

Wan, L., and Kang, Y. (2013). Pleiotropic roles of AEG-1/MTDH/LYRIC in breast cancer. Advances in cancer research 120, 113-134.

Wan, L., Pantel, K., and Kang, Y. (2013). Tumor metastasis: moving new biological insights into the clinic. Nature medicine 19, 1450-1464.

Weissbach, R., and Scadden, A. D. (2012). Tudor-SN and ADAR1 are components of cytoplasmic stress granules. Rna 18, 462-471.

Yin, Y., Bai, R., Russell, R. G., Beildeck, M. E., Xie, Z., Kopelovich, L., and Glazer, R. I. (2005). Characterization of medroxyprogesterone and DMBA-induced multilineage mammary tumors by gene expression profiling. Molecular carcinogenesis 44, 42-50.

Yoo, B. K., Santhekadur, P. K., Gredler, R., Chen, D., Emdad, L., Bhutia, S., Pannell, L., Fisher, P. B., and Sarkar, D. (2011). Increased RNA-induced silencing complex (RISC) activity contributes to hepatocellular carcinoma. Hepatology 53, 1538-1548.

Zhang, W., Tan, W., Wu, X., Poustovoitov, M., Strasner, A., Li, W., Borcherding, N., Ghassemian, M., and Karin, M. (2013a). A NIK-IKKalpha module expands ErbB2-induced tumor-initiating cells by stimulating nuclear export of p27/Kipl. Cancer Cell 23, 647-659.

Zhang, X., Claerhout, S., Prat, A., Dobrolecki, L. E., Petrovic, I., Lai, Q., Landis, M. D., Wiechmann, L., Schiff, R., Giuliano, M., et al. (2013b). A renewable tissue resource of phenotypically stable, biologically and ethnically diverse, patient-derived human breast cancer xenograft models. Cancer research 73, 4885-4897.

Greenberg N M, DeMayo F, Finegold M J, Medina D, Tilley W D, Aspinall J O, et al. Prostate cancer in a transgenic mouse. Proceedings of the National Academy of Sciences of the United States of America. 1995; 92:3439-43.

Gingrich J R, Barrios R J, Foster B A, Greenberg N M. Pathologic progression of autochthonous prostate cancer in the TRAMP model. Prostate cancer and prostatic diseases. 1999; 2:70-5.

Kaplan-Lefko P J, Chen T M, Ittmann M M, Barrios R J, Ayala G E, Huss W J, et al. Pathobiology of autochthonous prostate cancer in a pre-clinical transgenic mouse model. The Prostate. 2003; 55:219-37.

Hurwitz A A, Foster B A, Allison J P, Greenberg N M, Kwon E D. The TRAMP mouse as a model for prostate cancer. Current protocols in immunology/edited by John E Coligan [et al]. 2001; Chapter 20:Unit 20 5.

Chiaverotti T, Couto S S, Donjacour A, Mao J H, Nagase H, Cardiff R D, et al. Dissociation of epithelial and neuroendocrine carcinoma lineages in the transgenic adenocarcinoma of mouse prostate model of prostate cancer. Am J Pathol. 2008; 172:236-46.

Gingrich J R, Barrios R J, Morton R A, Boyce B F, DeMayo F J, Finegold M J, et al. Metastatic prostate cancer in a transgenic mouse. Cancer research. 1996; 56:4096-102.

Foster B A, Gingrich J R, Kwon E D, Madias C, Greenberg N M. Characterization of prostatic epithelial cell lines derived from transgenic adenocarcinoma of the mouse prostate (TRAMP) model. Cancer research. 1997; 57:3325-30.

Taylor B S, Schultz N, Hieronymus H, Gopalan A, Xiao Y, Carver B S, et al. Integrative genomic profiling of human prostate cancer. Cancer cell. 2010; 18:11-22.

Ding Z H, Wu C J, Jaskelioff M, Ivanova E, Kost-Alimova M, Protopopov A, et al. Telomerase Reactivation following Telomere Dysfunction Yields Murine Prostate Tumors with Bone Metastases. Cell. 2012; 148:896-907.

Liu Y, Su Z W, Li G, Yu C Y, Ren S L, Huang D H, et al. Increased expression of metadherin protein predicts worse disease-free and overall survival in laryngeal squamous cell carcinoma. Int J Cancer. 2013; 133:671-9.

Yu C, Liu Y, Tan H, Li G, Su Z, Ren S, et al. Metadherin regulates metastasis of squamous cell carcinoma of the head and neck via AKT signalling pathway-mediated epithelial-mesenchymal transition. Cancer letters. 2014; 343:258-67.

Zhu K, Dai Z, Pan Q, Wang Z, Yang G H, Yu L, et al. Metadherin Promotes Hepatocellular Carcinoma Metastasis through Induction of Epithelial-Mesenchymal Transition. Clinical Cancer Research. 2011; 17:7294-302.

Yoo B K, Emdad L, Su Z Z, Villanueva A, Chiang D Y, Mukhopadhyay N D, et al. Astrocyte elevated gene-1 regulates hepatocellular carcinoma development and progression. J Clin Invest. 2009; 119:465-77.

Otwinowski, Z., Minor, W. (1997). Processing of X-ray diffraction data collected in oscillation mode. Methods Enzymol 276, 307-326.

Adams, P. D., Afonine, P. V., Bunkoczi, G., Chen, V. B., Davis, I. W., Echols, N., Headd, J. J., Hung, L. W., Kapral, G. J., Grosse-Kunstleve, R. W., et al. (2010). PHENIX: a comprehensive Python-based system for macromolecular structure solution. Acta Crystallogr D Biol Crystallogr 66, 213-221.

McCoy, A. J., Grosse-Kunstleve, R. W., Adams, P. D., Winn, M. D., Storoni, L. C., and Read, R. J. (2007). Phaser crystallographic software. J Appl Crystallogr 40, 658-674.

Winn, M. D., Ballard, C. C., Cowtan, K. D., Dodson, E. J., Emsley, P., Evans, P. R., Keegan, R. M., Krissinel, E. B., Leslie, A. G., McCoy, A., et al. (2011). Overview of the CCP4 suite and current developments. Acta Crystallogr D Biol Crystallogr 67, 235-242.

Emsley, P., and Cowtan, K. (2004). Coot: model-building tools for molecular graphics. Acta Crystallogr D Biol Crystallogr 60, 2126-2132.

Weissbach, R., and Scadden, A. D. (2012). Tudor-SN and ADAR1 are components of cytoplasmic stress granules. Rna 18, 462-471.

Gao, X., Ge, L., Shao, J., Su, C., Zhao, H., Saarikettu, J., Yao, X., Yao, Z., Silvennoinen, O., and Yang, J. (2010). Tudor-SN interacts with and co-localizes with G3BP in stress granules under stress conditions. FEBS Lett 584, 3525-3532.

Emdad, L., Das, S. K., Dasgupta, S., Hu, B., Sarkar, D., and Fisher, P. B. (2013). AEG-1/MTDH/LYRIC: signaling pathways, downstream genes, interacting proteins, and regulation of tumor angiogenesis. Advances in cancer research 120, 75-111.

Li, C. L., Yang, W. Z., Chen, Y. P., and Yuan, H. S. (2008). Structural and functional insights into human Tudor-SN, a key component linking RNA interference and editing. Nucleic acids research 36, 3579-3589.

Gelman, I. H. (2012). Suppression of tumor and metastasis progression through the scaffolding functions of SSeCKS/Gravin/AKAP12. Cancer metastasis reviews 31, 493-500.

Thirkettle H J, Girling J, Warren A Y, Mills I G, Sahadevan K, Leung H, et al. LYRIC/AEG-1 is targeted to different subcellular compartments by ubiquitinylation and intrinsic nuclear localization signals. Clin Cancer Res. 2009; 15:3003-13.

Kikuno N, Shiina H, Urakami S, Kawamoto K, Hirata H, Tanaka Y, et al. Knockdown of astrocyte-elevated gene-1 inhibits prostate cancer progression through upregulation of FOXO3a activity. Oncogene. 2007; 26:7647-55.

Stryke D, Kawamoto M, Huang C C, Johns S J, King L A, Harper C A, et al. BayGenomics: a resource of insertional mutations in mouse embryonic stem cells. Nucleic Acids Res. 2003; 31:278-81.

Su Z Z, Kang D C, Chen Y, Pekarskaya O, Chao W, Volsky D J, et al. Identification and cloning of human astrocyte genes displaying elevated expression after infection with HIV-1 or exposure to HIV-1 envelope glycoprotein by rapid subtraction hybridization, RaSH. Oncogene. 2002; 21:3592-602.

Britt D E, Yang D F, Yang D Q, Flanagan D, Callanan H, Lim Y P, et al. Identification of a novel protein, LYRIC, localized to tight junctions of polarized epithelial cells. Experimental cell research. 2004; 300:134-48.

Sutherland H G, Lam Y W, Briers S, Lamond A I, Bickmore W A. 3D3/lyric: a novel transmembrane protein of the endoplasmic reticulum and nuclear envelope, which is also present in the nucleolus. Experimental cell research. 2004; 294:94-105.

Ash S C, Yang D Q, Britt D E. LYRIC/AEG-1 overexpression modulates BCCIPα lpha protein levels in prostate tumor cells. Biochem Biophys Res Commun. 2008; 371:333-8.

Emdad L, Sarkar D, Su Z Z, Randolph A, Boukerche H, Valerie K, et al. Activation of the nuclear factor kappaB pathway by astrocyte elevated gene-1: implications for tumor progression and metastasis. Cancer research. 2006; 66:1509-16.

Sarkar D, Park E S, Emdad L, Lee S G, Su Z Z, Fisher P B. Molecular basis of nuclear factor-kappaB activation by astrocyte elevated gene-1. Cancer research. 2008; 68:1478-84.

What is claimed:

1. A pharmaceutical composition comprising an inhibitor that disrupts the interaction between metadherin (MTDH) and Staphylococcal nuclease domain containing 1 (SND1) and a pharmaceutically acceptable carrier, excipient or diluent, wherein the inhibitor is a peptide or a fusion protein comprising the peptide linked to one or more polypeptides not generally recognized to be part of the sequence of MTDH, wherein the peptide comprises the amino acid sequence of DWNAPAEEWGN (SEQ ID NO: 5) or a variant thereof, wherein the variant has one or two mutations at positions selected from the group consisting of D393, N395, A396, PAE397-399, E399, E400, and N403, wherein the amino acid positions are based on SEQ ID NO: 1, and wherein the peptide is about 11 to about 22 amino acids long.

2. The pharmaceutical composition of claim 1, wherein the inhibitor is a peptide.

3. The pharmaceutical composition of claim 2, wherein the inhibitor is an MTDH peptide selected from the group consisting of i) a peptide within residues 364-582 of SEQ ID NO: 1, ii) a peptide within residues 364-407 of SEQ ID NO: 1, iii) a peptide comprising residues 386-407 of SEQ ID NO: 1, iv) a peptide comprising residues 393-403 of SEQ ID NO: 1 and v) a peptide comprising residues 390-403 of SEQ ID NO: 1.

4. The pharmaceutical composition of claim 2, wherein the peptide is part of a fusion protein.

5. The pharmaceutical composition of claim 4, where the peptide is fused to an Fc domain.

6. The pharmaceutical composition of claim 2, wherein the peptide is conjugated to or in admixture with a cell penetrating peptide.

7. The pharmaceutical composition of claim 1, wherein the peptide is conjugated to or in admixture with a cell penetrating peptide.

8. The pharmaceutical composition of claim 1, wherein the inhibitor is a peptide of about 11 to about 22 amino acids long, and wherein the peptide comprises residues 386-407 of SEQ ID NO: 1 or a variant thereof.

9. The pharmaceutical composition of claim 8, wherein the peptide comprises a variant of residues 386-407 of SEQ ID NO:1, wherein the variant comprises one or more mutations in residues 386-407 of SEQ ID NO: 1, wherein the one or more mutations are selected from the group consisting of D389, A392, D393, N395, E399, E400, W404, D406 and E407, and wherein the amino acid positions are based on SEQ ID NO: 1.

10. The pharmaceutical composition of claim 9, wherein the one or more mutations are selected from the group consisting of D389R, D393R, E399R, E400R, W404D, D406R and E407R.

11. The pharmaceutical composition of claim 1, wherein the peptide comprises a variant of SEQ ID NO: 5, and wherein the variant has a mutation selected from the group consisting of D393R, N395K, A396D, deletion of P (397) and substitution of AE(398-399) with SQ, E399R, E400R, and E400D/N403L.

12. The pharmaceutical composition of claim 3, wherein the inhibitor is an MTDH peptide within residues 364-582 of SEQ ID NO: 1.

13. The pharmaceutical composition of claim 3, wherein the inhibitor is a peptide within residues 364-407 of SEQ ID NO: 1.

14. The pharmaceutical composition of claim 3, wherein the inhibitor is a peptide comprising residues 386-407 of SEQ ID NO: 1.

15. The pharmaceutical composition of claim 3, wherein the inhibitor is a peptide comprising residues 393-403 of SEQ ID NO: 1.

16. The pharmaceutical composition of claim 3, wherein the inhibitor is a peptide comprising residues 390-403 of SEQ ID NO: 1.

17. The pharmaceutical composition of claim 3, wherein the peptide is conjugated to or in admixture with a cell penetrating peptide.

18. The pharmaceutical composition of claim 8, wherein the peptide is conjugated to or in admixture with a cell penetrating peptide.

19. The pharmaceutical composition of claim 11, wherein the peptide is conjugated to or in admixture with a cell penetrating peptide.

* * * * *

SEQUENCE LISTING

<160> NUMBER OF SEQ ID NOS: 20

<210> SEQ ID NO 1
<211> LENGTH: 582
<212> TYPE: PRT
<213> ORGANISM: Homo sapiens

<400> SEQUENCE: 1

```
Met Ala Ala Arg Ser Trp Gln Asp Glu Leu Ala Gln Gln Ala Glu Glu
1               5                   10                  15

Gly Ser Ala Arg Leu Arg Glu Met Leu Ser Val Gly Leu Gly Phe Leu
            20                  25                  30

Arg Thr Glu Leu Gly Leu Asp Leu Gly Leu Glu Pro Lys Arg Tyr Pro
        35                  40                  45

Gly Trp Val Ile Leu Val Gly Thr Gly Ala Leu Gly Leu Leu Leu Leu
    50                  55                  60

Phe Leu Leu Gly Tyr Gly Trp Ala Ala Ala Cys Ala Gly Ser Arg Lys
65                  70                  75                  80

Lys Arg Arg Ser Pro Pro Arg Lys Arg Glu Glu Ala Ala Ala Val Pro
                85                  90                  95

Ala Ala Ala Pro Asp Asp Leu Ala Leu Leu Lys Asn Leu Arg Ser Glu
            100                 105                 110

Glu Gln Lys Lys Lys Asn Arg Lys Lys Leu Ser Glu Lys Pro Lys Pro
        115                 120                 125

Asn Gly Arg Thr Val Glu Val Ala Glu Gly Glu Ala Val Arg Thr Pro
    130                 135                 140

Gln Ser Val Thr Ala Lys Gln Pro Pro Glu Ile Asp Lys Lys Asn Glu
145                 150                 155                 160

Lys Ser Lys Lys Asn Lys Lys Lys Ser Lys Ser Asp Ala Lys Ala Val
                165                 170                 175

Gln Asn Ser Ser Arg His Asp Gly Lys Glu Val Asp Glu Gly Ala Trp
            180                 185                 190

Glu Thr Lys Ile Ser His Arg Glu Lys Arg Gln Gln Arg Lys Arg Asp
        195                 200                 205

Lys Val Leu Thr Asp Ser Gly Ser Leu Asp Ser Thr Ile Pro Gly Ile
    210                 215                 220

Glu Asn Thr Ile Thr Val Thr Thr Glu Gln Leu Thr Thr Ala Ser Phe
225                 230                 235                 240

Pro Val Gly Ser Lys Lys Asn Lys Gly Asp Ser His Leu Asn Val Gln
                245                 250                 255

Val Ser Asn Phe Lys Ser Gly Lys Gly Asp Ser Thr Leu Gln Val Ser
            260                 265                 270

Ser Gly Leu Asn Glu Asn Leu Thr Val Asn Gly Gly Trp Asn Glu
        275                 280                 285

Lys Ser Val Lys Leu Ser Ser Gln Ile Ser Ala Gly Glu Glu Lys Trp
    290                 295                 300

Asn Ser Val Ser Pro Ala Ser Ala Gly Lys Arg Lys Ala Glu Pro Ser
305                 310                 315                 320

Ala Trp Ser Gln Asp Thr Gly Asp Ala Asn Thr Asn Gly Lys Asp Trp
                325                 330                 335

Gly Arg Ser Trp Ser Asp Arg Ser Ile Phe Ser Gly Ile Gly Ser Thr
            340                 345                 350

Ala Glu Pro Val Ser Gln Ser Thr Ser Asp Tyr Gln Trp Asp Val
        355                 360                 365
```

```
Ser Arg Asn Gln Pro Tyr Ile Asp Asp Glu Trp Ser Gly Leu Asn Gly
    370                 375                 380

Leu Ser Ser Ala Asp Pro Asn Ser Asp Trp Asn Ala Pro Ala Glu Glu
385                 390                 395                 400

Trp Gly Asn Trp Val Asp Glu Arg Ala Ser Leu Leu Lys Ser Gln
                405                 410                 415

Glu Pro Ile Pro Asp Gln Lys Val Ser Asp Asp Lys Glu Lys
            420                 425                 430

Gly Glu Gly Ala Leu Pro Thr Gly Lys Ser Lys Lys Lys Lys
            435                 440                 445

Lys Lys Lys Gln Gly Glu Asp Asn Ser Thr Ala Gln Asp Thr Glu Glu
450                 455                 460

Leu Glu Lys Glu Ile Arg Glu Asp Leu Pro Val Asn Thr Ser Lys Thr
465                 470                 475                 480

Arg Pro Lys Gln Glu Lys Ala Phe Ser Leu Lys Thr Ile Ser Thr Ser
                485                 490                 495

Asp Pro Ala Glu Val Leu Val Lys Asn Ser Gln Pro Ile Lys Thr Leu
            500                 505                 510

Pro Pro Ala Thr Ser Thr Glu Pro Ser Val Ile Leu Ser Lys Ser Asp
            515                 520                 525

Ser Asp Lys Ser Ser Gln Val Pro Pro Ile Leu Gln Glu Thr Asp
530                 535                 540

Lys Ser Lys Ser Asn Thr Lys Gln Asn Ser Val Pro Pro Ser Gln Thr
545                 550                 555                 560

Lys Ser Glu Thr Ser Trp Glu Ser Pro Lys Gln Ile Lys Lys Lys Lys
                565                 570                 575

Lys Ala Arg Arg Glu Thr
            580

<210> SEQ ID NO 2
<211> LENGTH: 910
<212> TYPE: PRT
<213> ORGANISM: Homo sapiens

<400> SEQUENCE: 2

Met Ala Ser Ser Ala Gln Ser Gly Gly Ser Gly Gly Pro Ala Val
1               5                   10                  15

Pro Thr Val Gln Arg Gly Ile Ile Lys Met Val Leu Ser Gly Cys Ala
                20                  25                  30

Ile Ile Val Arg Gly Gln Pro Arg Gly Pro Pro Glu Arg Gln
            35                  40                  45

Ile Asn Leu Ser Asn Ile Arg Ala Gly Asn Leu Ala Arg Arg Ala Ala
50                  55                  60

Ala Thr Gln Pro Asp Ala Lys Asp Thr Pro Glu Pro Trp Ala Phe
65                  70                  75                  80

Pro Ala Arg Glu Phe Leu Arg Lys Lys Leu Ile Gly Lys Glu Val Cys
                85                  90                  95

Phe Thr Ile Glu Asn Lys Thr Pro Gln Gly Arg Glu Tyr Gly Met Ile
                100                 105                 110

Tyr Leu Gly Lys Asp Thr Asn Gly Glu Asn Ile Ala Glu Ser Leu Val
                115                 120                 125

Ala Glu Gly Leu Ala Thr Arg Arg Glu Gly Met Arg Ala Asn Asn Pro
130                 135                 140

Glu Gln Asn Arg Leu Ser Glu Cys Glu Glu Gln Ala Lys Ala Ala Lys
145                 150                 155                 160
```

-continued

```
Lys Gly Met Trp Ser Glu Gly Asn Gly Ser His Thr Ile Arg Asp Leu
            165                 170                 175
Lys Tyr Thr Ile Glu Asn Pro Arg His Phe Val Asp Ser His His Gln
            180                 185                 190
Lys Pro Val Asn Ala Ile Ile Glu His Val Arg Asp Gly Ser Val Val
            195                 200                 205
Arg Ala Leu Leu Leu Pro Asp Tyr Tyr Leu Val Thr Val Met Leu Ser
210                 215                 220
Gly Ile Lys Cys Pro Thr Phe Arg Arg Glu Ala Asp Gly Ser Glu Thr
225                 230                 235                 240
Pro Glu Pro Phe Ala Ala Glu Ala Lys Phe Phe Thr Glu Ser Arg Leu
            245                 250                 255
Leu Gln Arg Asp Val Gln Ile Ile Leu Glu Ser Cys His Asn Gln Asn
            260                 265                 270
Ile Leu Gly Thr Ile Leu His Pro Asn Gly Asn Ile Thr Glu Leu Leu
            275                 280                 285
Leu Lys Glu Gly Phe Ala Arg Cys Val Asp Trp Ser Ile Ala Val Tyr
            290                 295                 300
Thr Arg Gly Ala Glu Lys Leu Arg Ala Ala Glu Arg Phe Ala Lys Glu
305                 310                 315                 320
Arg Arg Leu Arg Ile Trp Arg Asp Tyr Val Ala Pro Thr Ala Asn Leu
            325                 330                 335
Asp Gln Lys Asp Lys Gln Phe Val Ala Lys Val Met Gln Val Leu Asn
            340                 345                 350
Ala Asp Ala Ile Val Val Lys Leu Asn Ser Gly Asp Tyr Lys Thr Ile
            355                 360                 365
His Leu Ser Ser Ile Arg Pro Pro Arg Leu Glu Gly Glu Asn Thr Gln
            370                 375                 380
Asp Lys Asn Lys Lys Leu Arg Pro Leu Tyr Asp Ile Pro Tyr Met Phe
385                 390                 395                 400
Glu Ala Arg Glu Phe Leu Arg Lys Lys Leu Ile Gly Lys Lys Val Asn
            405                 410                 415
Val Thr Val Asp Tyr Ile Arg Pro Ala Ser Pro Ala Thr Glu Thr Val
            420                 425                 430
Pro Ala Phe Ser Glu Arg Thr Cys Ala Thr Val Thr Ile Gly Gly Ile
            435                 440                 445
Asn Ile Ala Glu Ala Leu Val Ser Lys Gly Leu Ala Thr Val Ile Arg
            450                 455                 460
Tyr Arg Gln Asp Asp Asp Gln Arg Ser Ser His Tyr Asp Glu Leu Leu
465                 470                 475                 480
Ala Ala Glu Ala Arg Ala Ile Lys Asn Gly Lys Gly Leu His Ser Lys
            485                 490                 495
Lys Glu Val Pro Ile His Arg Val Ala Asp Ile Ser Gly Asp Thr Gln
            500                 505                 510
Lys Ala Lys Gln Phe Leu Pro Phe Leu Gln Arg Ala Gly Arg Ser Glu
            515                 520                 525
Ala Val Val Glu Tyr Val Phe Ser Gly Ser Arg Leu Lys Leu Tyr Leu
            530                 535                 540
Pro Lys Glu Thr Cys Leu Ile Thr Phe Leu Leu Ala Gly Ile Glu Cys
545                 550                 555                 560
Pro Arg Gly Ala Arg Asn Leu Pro Gly Leu Val Gln Glu Gly Glu Pro
            565                 570                 575
```

```
Phe Ser Glu Glu Ala Thr Leu Phe Thr Lys Glu Leu Val Leu Gln Arg
                580                 585                 590

Glu Val Glu Val Glu Val Glu Ser Met Asp Lys Ala Gly Asn Phe Ile
            595                 600                 605

Gly Trp Leu His Ile Asp Gly Ala Asn Leu Ser Val Leu Leu Val Glu
        610                 615                 620

His Ala Leu Ser Lys Val His Phe Thr Ala Glu Arg Ser Ser Tyr Tyr
625                 630                 635                 640

Lys Ser Leu Leu Ser Ala Glu Ala Ala Lys Gln Lys Lys Glu Lys
                645                 650                 655

Val Trp Ala His Tyr Glu Glu Gln Pro Val Glu Glu Val Met Pro Val
                660                 665                 670

Leu Glu Glu Lys Glu Arg Ser Ala Ser Tyr Lys Pro Val Phe Val Thr
                675                 680                 685

Glu Ile Thr Asp Asp Leu His Phe Tyr Val Gln Asp Val Glu Thr Gly
            690                 695                 700

Thr Gln Leu Glu Lys Leu Met Glu Asn Met Arg Asn Asp Ile Ala Ser
705                 710                 715                 720

His Pro Pro Val Glu Gly Ser Tyr Ala Pro Arg Arg Gly Glu Phe Cys
                725                 730                 735

Ile Ala Lys Phe Val Asp Gly Glu Trp Tyr Arg Ala Arg Val Glu Lys
                740                 745                 750

Val Glu Ser Pro Ala Lys Ile His Val Phe Tyr Ile Asp Tyr Gly Asn
                755                 760                 765

Arg Glu Val Leu Pro Ser Thr Arg Leu Gly Thr Leu Ser Pro Ala Phe
770                 775                 780

Ser Thr Arg Val Leu Pro Ala Gln Ala Thr Glu Tyr Ala Phe Ala Phe
785                 790                 795                 800

Ile Gln Val Pro Gln Asp Asp Ala Arg Thr Asp Ala Val Asp Ser
                805                 810                 815

Val Val Arg Asp Ile Gln Asn Thr Gln Cys Leu Leu Asn Val Glu His
                820                 825                 830

Leu Ser Ala Gly Cys Pro His Val Thr Leu Gln Phe Ala Asp Ser Lys
                835                 840                 845

Gly Asp Val Gly Leu Gly Leu Val Lys Glu Gly Leu Val Met Val Glu
850                 855                 860

Val Arg Lys Glu Lys Gln Phe Gln Lys Val Ile Thr Glu Tyr Leu Asn
865                 870                 875                 880

Ala Gln Glu Ser Ala Lys Ser Ala Arg Leu Asn Leu Trp Arg Tyr Gly
                885                 890                 895

Asp Phe Arg Ala Asp Asp Ala Asp Glu Phe Gly Tyr Ser Arg
                900                 905                 910

<210> SEQ ID NO 3
<211> LENGTH: 11
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid
<220> FEATURE:
<221> NAME/KEY: misc_feature
<222> LOCATION: (10)..(11)
```

```
<223> OTHER INFORMATION: Xaa can be any naturally occurring amino acid

<400> SEQUENCE: 3

Xaa Trp Xaa Xaa Xaa Xaa Xaa Xaa Trp Xaa Xaa
1               5                   10

<210> SEQ ID NO 4
<211> LENGTH: 10
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 4

Xaa Trp Xaa Xaa Xaa Xaa Xaa Trp Xaa Xaa
1               5                   10

<210> SEQ ID NO 5
<211> LENGTH: 11
<212> TYPE: PRT
<213> ORGANISM: Homo sapiens

<400> SEQUENCE: 5

Asp Trp Asn Ala Pro Ala Glu Glu Trp Gly Asn
1               5                   10

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
ctgcaaaaca agcaccagag                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
gttttcccag tcacgacgtt                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
gagaggaggt tttggggaag                                              20

<210> SEQ ID NO 9
```

<211> LENGTH: 21
<212> TYPE: DNA
<213> ORGANISM: Artificial Sequence
<220> FEATURE:
<223> OTHER INFORMATION: Synthetic primer

<400> SEQUENCE: 9
cccatgtcta aaaagccaat c        21

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
gagaggaggt tttggggaag        20

<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11
gttcatatgg tgccgtgcag        20

<210> SEQ ID NO 12
<211> LENGTH: 24
<212> TYPE: DNA
<213> ORGANISM: Artificial Sequence
<220> FEATURE:
<223> OTHER INFORMATION: Synthetic primer

<400> SEQUENCE: 12
caagactctt cctcctgcta tctc        24

<210> SEQ ID NO 13
<211> LENGTH: 24
<212> TYPE: DNA
<213> ORGANISM: Artificial Sequence
<220> FEATURE:
<223> OTHER INFORMATION: Synthetic primer

<400> SEQUENCE: 13
cccattcatc agttccatag gttg        24

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
caaatgttgc ttgtctggtg        20

<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15

```
gtcagtcgag tgcacagttt                                              20

<210> SEQ ID NO 16
<211> LENGTH: 15
<212> TYPE: PRT
<213> ORGANISM: Homo sapiens

<400> SEQUENCE: 16

Pro Asn Ser Asp Trp Asn Ala Pro Ala Glu Glu Trp Gly Asn Trp
1               5                   10                  15

<210> SEQ ID NO 17
<211> LENGTH: 15
<212> TYPE: PRT
<213> ORGANISM: Homo sapiens

<400> SEQUENCE: 17

Pro Asn Ser Asp Ala Asn Ala Pro Ala Glu Glu Trp Gly Asn Trp
1               5                   10                  15

<210> SEQ ID NO 18
<211> LENGTH: 15
<212> TYPE: PRT
<213> ORGANISM: Homo sapiens

<400> SEQUENCE: 18

Pro Asn Ser Asp Trp Asn Ala Pro Ala Glu Glu Ala Gly Asn Trp
1               5                   10                  15

<210> SEQ ID NO 19
<211> LENGTH: 15
<212> TYPE: PRT
<213> ORGANISM: Homo sapiens

<400> SEQUENCE: 19

Pro Asn Ser Asp Ala Asn Ala Pro Ala Glu Glu Ala Gly Asn Trp
1               5                   10                  15

<210> SEQ ID NO 20
<211> LENGTH: 10
<212> TYPE: PRT
<213> ORGANISM: Homo sapiens

<400> SEQUENCE: 20

Asp Trp Asn Ala Pro Glu Glu Trp Gly Asn
1               5                   10
```